United States Patent
Encell et al.

(10) Patent No.: US 10,633,690 B2
(45) Date of Patent: *Apr. 28, 2020

(54) SYNTHETIC OPLOPHORUS LUCIFERASES WITH ENHANCED LIGHT OUTPUT

(71) Applicant: Promega Corporation, Madison, WI (US)

(72) Inventors: Lance P. Encell, Fitchburg, WI (US); Mary Hall, Waunakee, WI (US); Paul Otto, Madison, WI (US); Gediminas Vidugiris, Fitchburg, WI (US); Keith V. Wood, Mt. Horeb, WI (US); Monika G. Wood, Mt. Horeb, WI (US); Kristopher Zimmerman, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,464

(22) Filed: Mar. 6, 2019

(65) Prior Publication Data

US 2019/0185908 A1    Jun. 20, 2019

Related U.S. Application Data

(63) Continuation of application No. 15/714,210, filed on Sep. 25, 2017, now Pat. No. 10,233,485, which is a continuation of application No. 14/053,252, filed on Oct. 14, 2013, now Pat. No. 9,777,311, which is a continuation of application No. 12/773,002, filed on May 3, 2010, now Pat. No. 8,557,970.

(60) Provisional application No. 61/174,838, filed on May 1, 2009.

(51) Int. Cl.
   *C12Q 1/66* (2006.01)
   *C12N 9/00* (2006.01)
   *C12N 9/02* (2006.01)

(52) U.S. Cl.
   CPC ............ *C12Q 1/66* (2013.01); *C12N 9/0004* (2013.01)

(58) Field of Classification Search
   None
   See application file for complete search history.

(56) References Cited

U.S. PATENT DOCUMENTS

| | | |
|---|---|---|
| 6,544,754 B2 | 4/2003 | Inoye |
| 7,118,878 B1 | 10/2006 | Hawkins |
| 7,125,697 B2 | 10/2006 | Inoye |
| 8,557,970 B2 | 10/2013 | Encell et al. |
| 2004/0002127 A1 | 1/2004 | Inouye |
| 2008/0248511 A1 | 10/2008 | Daily |
| 2009/0253131 A1 | 10/2009 | Wigdal |
| 2009/0305353 A1 | 12/2009 | Fujii et al. |
| 2011/0039257 A1 | 2/2011 | Binkowski et al. |
| 2012/0034672 A1 | 2/2012 | Kim et al. |
| 2014/0120548 A1 | 5/2014 | Encell et al. |

FOREIGN PATENT DOCUMENTS

| | | |
|---|---|---|
| EP | 1148139 | 10/2001 |
| JP | 2002320482 A | 11/2002 |
| JP | 2005245457 A | 9/2005 |
| WO | 1995018853 | 7/1995 |
| WO | 9014336 | 3/1999 |
| WO | 01031028 A2 | 5/2001 |
| WO | 2003040100 | 5/2003 |
| WO | 2007120522 | 10/2007 |
| WO | 2010127368 | 11/2010 |
| WO | 2012061530 | 5/2012 |

OTHER PUBLICATIONS

Wada, K. et al., "Codon usage tabulated from the GenBank genetic sequence data," Nucl. Acids Res. (1990) 18 (Supp):2367-2411.
Wells, J.A. "Additivity of Mutational Effects in Proteins." Perspectives in Biotechnology, American Chemical Society Sep. 18, 1990, 29(37): 5809-5817.
European Search Report for EP 15186652, dated Jan. 5, 2016, 5 pages.
Angelucci, F. et al., "Schistosoma mansoni fatty acid binding protein: specificity and functional control as revealed by crystallographic structure," Biochem. (2004) 43:13000-13011.
Arnold, K. et al., "The Swiss-Model workspace: a web-based environment for protein structure homology modelling," Bioinformatics (2006) 22(2):195-201.
Becker, M.M. et al., "Gene cloning, overproduction and purification of a functionally active cytoplasmic fatty acid-binding protein (Sj-FABPc) from the human blood fluke *Schistosoma japonicum*," Gene (1994) 148:321-325.
Chakravarty et al., "Accuracy of structure-derived properties in simple comparative models of protein structures." Nucleic Acids Research 2009, 33(1): 244-259.
Cowan, S.W. et al., "Crystallographic studies on a family of cellular lipophillic transport proteins," J. Mol. Biol. (1993) 230;1225-1246.

(Continued)

*Primary Examiner* — Suzanne M Noakes
(74) *Attorney, Agent, or Firm* — Casimir Jones SC; David W. Staple

(57) ABSTRACT

A polynucleotide encoding a modified luciferase polypeptide. The modified luciferase polypeptide has at least 60% amino acid sequence identity to a wild-type *Oplophorus* luciferase and includes at least one amino acid substitution at a position corresponding to an amino acid in a wild-type *Oplophorus* luciferase of SEQ ID NO:1. The modified luciferase polypeptide has at least one of enhanced luminescence, enhanced signal stability, and enhanced protein stability relative to the wild-type *Oplophorus* luciferase.

30 Claims, 61 Drawing Sheets

Specification includes a Sequence Listing.

(56) References Cited

OTHER PUBLICATIONS

Daughtery, P.S. et al., "Quantitative analysis of the effect of the mutation frequency on the affinity maturation of single chain Fv antibodies," Proc. Natl. Acad. Sci. USA (2000) 97(5):2029-2034.
Dennell, R. et al., "Observations on the luminescence of bathypelagic crustacea decapoda of the Bermuda area," J. linnean. Soc. London (1955) XLII:393-406.
Flower, D.R. et al., "A structural signature characteristic of the calycin protein superfamily," Protein Pept. Lett. (1995) 2(2)341-350.
Flower, D.R. et al., "Structure and sequence relationships in the lipocalins and related proteins," Protein Sci. (1993) 2:753-761.
Flower, D.R. et al., "The lipocalin protein family—structure and function," Biochem. J. (1996) 318:1-14.
Flower, D.R. et al., "The lipocalin protein family-structural and sequence overview," Biochimica et Biophysica Acta (2000) 1482:9-24.
Fujii, H. et al., "Increase in bioluminescence intensity of firefly luciferase using genetic modification," Anal. Biochem. (2007) 366:131-136.
Head, J.F. et al., "The crystal structure of the photoprotein aequorin at 2.3A resolution," Nature (2000) 405:372-376.
Herring, P.J. et al., "Bioluminescence in crustacea," J. Crust. Biol. (1985) 5(4):557-573.
Herring, P.J. et al., "The spectral characteristics of luminous marine organisms," Proc. Royal Society London Series B. Biological Sciences (1983) 220(1219):183-217.
Herring, P.J., "Bioluminescence in decapod crustacea," J. Mar. Biol. Assoc. UK (1976) 156:1029-1047.
Inoue, S. et al., "Complete structure of renilla luciferin and luciferyl sulfate," Tetra. Lett (1977) 31:2685-2688.
Inouye, S. et al., "Overexpression, purification and characterization of the catalytic component of oplophorus luciferase in the deep sea shrimp," Protein Exp. Purification (2007) 56(2):261-268.
Inouye, S. et al., "Secretional luciferase of the luminous shrimp *Oplophorus gracilirostris*: cDNA cloning of a novel midazopyrazinone luciferase," FEBS Letts. (2000) 481:19-25.
International Search Report and Written Opinion for Application No. PCT/US2010/033449 dated Aug. 18, 2010 (12 pages).
International Search Report and Written Opinion for Application No. PCT/US2011/058924 dated Jan. 24, 2012 (8 pages).
International Search Report and Written Opinion for Application No. PCT/US2011/059017 dated Jan. 18, 2012 (8 pages).
Johnson, F.H. et al., "Introduction to the cypridina system," Meth. Enzym. (1978) 57:331-364.
Kabsch, W. et al., "Dictionary of protein secondary structure: pattern recognition of hydrogen-bonded and geometrical features," Biopolymers (1983) 22:2577-2637.
Karplus, K. et al., "Hidden Markov models for detecting remote protein homologies," Bioinformatics (1998) 14 (10):846-856.
King, R.D. et al., "Identification and application of the concepts important for accurate and reliable protein secondary structure prediction," Protein Sci. (1996) 5:2298-2310.
Kunkel, T.A., "Rapid and efficient site-specific mutagenesis without phenotypic selection," Proc. Natl. Acad. Sci. USA (1985) 82(2):488-492.
Kurowski, M.A. et al., "GeneSilico protein structure prediction meta-server," Nucl. Acids. Res. (2003) 31 (13)3305-3307.
Loening, A.M. et al., "Consensus guided mutagenesis of renilla luciferase yeilds enhanced stability and light output," Protein Eng. Des. Sel. (2006) 19(9):391-400.
Lorenz, W.W. et al.,"Isolation and expression of a cDNA encoding renilla reinformis luciferase," Proc. Natl. Acad. Sci. USA (1991) 88:4438-4442.
McGuffin, L.J. et al., "The PSIPRED protein structure prediction server," Bioinformatics (2000) 16(4):404-405.
Murray, E.E. et al., "Codon usage in plant genes," Nucl. Acids. Res. (1989) 17(2):477-498.
Nakamura, H. et al., "Efficient bioluminescence of bisdeoxycoelenterazine with the luciferase of a deep-sea shrimp oplophorus," Tetra. Lett. (1997) 38(36):6405-6406.
Needleman, S.B. et al., "A general method applicable to the search for similarities in the amino acid sequence of two proteins," J. Mol. Biol. (1970) 48:443-453.
Nowel, M.S. et al., "Cuticular photophores of two decapod crustaceans, *Oplophorus spinosus* and *Systellaspis debilis*," Biol. Bull. (1998) 195:290-307.
Parsons, M.R. et al., "Crystal structure of a quinoenzyme: copper amine oxidase of *Escherichia coli* at 2 A resolution," Structure (1995) 3:1171-1184.
Pearson, W.R. et al., "Improved tools for biological sequence comparison," Proc. Natl. Acad. Sci. USA (1988) 85:2444-2448.
Pichler et al., "Imaging reversal of multidrug resistance in living mice with bioluminescence: MDR1 P-glycoprotein transports coelenterazine." Proc. Natl. Acaa. Sci. USA 2004, 101(6): 1702-1707.
Pollastri, G. et al., "Porter: a new, accurate server for protein secondary structure prediction," Bioinformatics (2005) 21(8):1719-1720.
Poupin, J., "Plancton marin bioluminescent," Rapport Scientifique du Leon (Sep. 1999) 1-83.
Schagat, T. et al., "KRX autoinduction protocol: a convenient method for protein expression," Promega Notes (2008) 98:16-18.
Schultz, L.W. et al., "Crystal structure of a pH-regulated luciferase catalyzing the bioluminescent oxidation of an open tetrapyrrole," Proc. Natl. Acad. Sci. USA (2005) 102(5):1378-1383.
Shimomura et al., "Sem-synthetic aequorins with improved sensitivity to CA2+ ions." Biochem. J. 1989, 261:913-920.
Shimomura, O. et al., "Properties and reaction mechanism of the bioluminescence system of the deep-sea shrimp *Oplophorus gracilorostris*," Biochem. (1978) 17:994-998.
Skerra, A., "Lipocalins as a scaffold," Biochem et Biophys. Acta (2000) 1482:337-350.
Skolnick & Fetrow, "From genes to protein structure and function: novel applications of computational approaches in the genomic era." Tibtech Jan. 2000, 18:34-39.
Smith, T.F. et al., "Identification of common molecular subsequences," J. Mol. Biol. (1981) 147:195-197.
Thompson, E.M. et al., "Cloning and expression of cDNA for the luciferase from the marine ostracod *Vargula hilgendorfii*," Proc. Natl. Acad. Sci. USA (1989) 86:6567-6571.
Todd et al., "Evolution of Function in Protein Superfamilies, from a Structural Perspective." J. Mol. Biol 2001, 307:1113-1143.

FIG. 3

T=0 (injector) 0.5% tergitol assay buffer

| Sample | Average | Stdev | CV |
|---|---|---|---|
| WT | 116,132 | 13,032 | 11.2% |
| N166R | 160,334 | 18,014 | 11.2% |
| T2T | 259,374 | 17,488 | 6.7% |
| T2T+N166R | 367,468 | 30,406 | 8.3% |
| A4E | 193,837 | 10,272 | 5.3% |
| Q11R | 172,425 | 16,389 | 9.5% |
| V44I | 2,155,303 | 231,323 | 10.7% |
| A54F | 1,559,763 | 121,554 | 7.8% |
| A54F+N166R | 8,052,686 | 981,637 | 12.2% |
| A54I | 15,676,789 | 2,266,808 | 14.5% |
| P115E | 406,670 | 18,160 | 4.5% |
| P115E+N166R | 489,722 | 26,228 | 5.4% |
| Y138I | 1,119,166 | 128,394 | 11.5% |
| Q124K | 322,475 | 30,313 | 9.4% |
| Y138C+N166R | 590,665 | 40,138 | 6.8% |
| I90V | 387,765 | 29,162 | 7.5% |

FIG. 5A

T=0 RLAB with injector

| Sample | Average | Stdev | CV |
|---|---|---|---|
| WT | 2,266,822 | 222,850 | 9.8% |
| N166R | 5,582,331 | 514,426 | 9.2% |
| T2T | 3,599,341 | 244,441 | 6.8% |
| T2T+N166R | 9,823,129 | 457,592 | 4.7% |
| A4E | 2,888,005 | 231,055 | 8.0% |
| Q11R | 4,043,391 | 179,037 | 4.4% |
| V44I | 12,935,691 | 546,014 | 4.2% |
| A54F | 8,572,288 | 464,442 | 5.4% |
| A54F+N166R | 79,773,644 | 3,157,533 | 4.0% |
| A54I | 32,309,914 | 2,594,059 | 8.0% |
| P115E | 7,400,192 | 416,225 | 5.6% |
| P115E+N166R | 16,167,230 | 481,714 | 3.0% |
| Y138I | 14,573,569 | 619,909 | 4.3% |
| Q124K | 5,473,417 | 517,799 | 9.5% |
| Y138C+N166R | 15,516,040 | 1,147,103 | 7.4% |
| I90V | 4,474,794 | 297,720 | 6.7% |

FIG. 7A

T=0 RLAB with injector

Figure 7B

Signal ½ life (minutes) RLAB

| Sample | Signal 1/2 life (minutes) RLAB |
|---|---|
| WT | 9.03 |
| N166R | 8.17 |
| T2T | 9.79 |
| T2T + N166R | 8.74 |
| A4E | 11.48 |
| Q11R | 8.69 |
| V44I | 8.54 |
| A54F | 6.80 |
| A54F + N166R | 7.30 |
| A54I | 10.88 |
| P115E | 8.31 |
| P115E + N166R | 8.16 |
| Y138I | 8.36 |
| Q124K | 8.77 |
| Y138C + N166R | 4.97 |
| I90V | 8.83 |

FIG. 11A

Stability at 22°C (1/2 life in minutes)

| Sample | stability (1/2 life at 22C) |
|---|---|
| WT | 38.1 |
| N166R | 61.3 |
| T2T | 43.1 |
| T2T+N166R | 68.0 |
| A4E | 38.5 |
| Q11R | 45.9 |
| V44I | 49.5 |
| A54F | 56.8 |
| A54F+N166R | 177.7 |
| A54I | 63.0 |
| P115E | 49.9 |
| P115E+N166R | 119.5 |
| Y138I | 55.9 |
| Q124K | 43.9 |
| Y138C+N166R | 35.5 |
| I90V | 41.3 |

FIG. 12A

Signal stability 0.5% tergitol assay buffer

| Sample | Signal 1/2 life (0.5% tertitol assay buffer) |
|---|---|
| WT | 6.5 |
| N166R | 9.6 |
| WTA33K | 7.4 |
| WTF68Y | 6.3 |
| N166R A33K | 6.3 |
| N166R F68Y | 6.2 |

FIG. 15B

Signal stability RLAB

| Sample | signal 1/2 life minutes |
|---|---|
| WT | 7.64 |
| N166R | 6.73 |
| A33K | 9.22 |
| F68Y | 8.13 |
| N166RA33K | 6.58 |
| N166R/F68Y | 6.60 |

FIG. 16B

Stability ½ life at 22°C

| Sample | 1/2 life (min) 22C |
|---|---|
| WT | 54.6 |
| N166R | 67.3 |
| A33K | 58.2 |
| F68Y | 57.3 |
| N166R, A33K | 72.2 |
| N166R, F68Y | 77.9 |

FIG. 17

0.5% tergitol assay buffer

| time(min) | N166R | C1+A4E | C1+A4E+F54T | C1+C2+A4E | C1+C3+A4E | C1+C3+A4E+F54T | Renilla |
|---|---|---|---|---|---|---|---|
| 0.0 | 1,110 | 7,910,000 | 3,583,750 | 43,371 | 4,217,500 | 3,322,500 | 3,542,500 |
| 0.6 | 970 | 7,876,250 | 3,587,500 | 43,902 | 4,217,500 | 3,326,250 | 3,543,750 |
| 1.2 | 1,277 | 7,888,750 | 3,576,250 | 45,133 | 4,243,750 | 3,351,250 | 3,557,500 |
| 1.8 | 872 | 7,868,750 | 3,566,250 | 43,553 | 4,257,500 | 3,338,750 | 3,563,750 |
| 2.4 | 1,110 | 7,887,500 | 3,575,000 | 42,476 | 4,260,000 | 3,366,250 | 3,571,250 |
| 3.0 | 1,137 | 7,880,000 | 3,576,250 | 43,036 | 4,266,250 | 3,397,500 | 3,562,500 |
| 3.6 | 1,193 | 7,860,000 | 3,577,500 | 43,637 | 4,276,250 | 3,386,250 | 3,586,250 |
| 4.2 | 1,095 | 7,855,000 | 3,556,250 | 42,896 | 4,293,750 | 3,406,250 | 3,568,750 |
| 4.8 | 928 | 7,862,500 | 3,556,250 | 44,755 | 4,290,000 | 3,415,000 | 3,565,000 |
| 5.4 | 998 | 7,852,500 | 3,538,750 | 44,112 | 4,315,000 | 3,422,500 | 3,568,750 |
| 6.0 | 774 | 7,843,750 | 3,542,500 | 44,196 | 4,311,250 | 3,433,750 | 3,551,250 |
| 6.6 | 1,026 | 7,841,250 | 3,520,000 | 42,938 | 4,332,500 | 3,431,250 | 3,525,000 |
| 7.2 | 1,277 | 7,786,250 | 3,516,250 | 43,217 | 4,311,250 | 3,445,000 | 3,512,500 |
| 7.8 | 1,012 | 7,783,750 | 3,511,250 | 43,986 | 4,318,750 | 3,430,000 | 3,486,250 |
| 8.4 | 816 | 7,775,000 | 3,491,250 | 43,483 | 4,317,500 | 3,440,000 | 3,467,500 |
| 9.0 | 1,110 | 7,771,250 | 3,471,250 | 42,854 | 4,317,500 | 3,450,000 | 3,416,250 |
| 9.6 | 928 | 7,750,000 | 3,460,000 | 44,713 | 4,308,750 | 3,465,000 | 3,422,500 |
| 10.1 | 732 | 7,705,000 | 3,457,500 | 44,168 | 4,320,000 | 3,462,500 | 3,386,250 |
| 10.7 | 970 | 7,706,250 | 3,451,250 | 43,245 | 4,296,250 | 3,433,750 | 3,363,750 |
| 11.3 | 1,068 | 7,687,500 | 3,430,000 | 43,902 | 4,315,000 | 3,450,000 | 3,333,750 |

Figure 18A

Og luc composites 0.5% tergitol

| time(min) | C1+C2+A4E | C1+A4 | hRL | Og-Luc | T2T | A54F |
|---|---|---|---|---|---|---|
| 0 | 3,283,757 | 705,604,545 | 82,499,609 | 40,946 | 129,209 | 3,196,722 |
| 1 | 3,272,774 | 655,089,672 | 81,682,809 | 43,269 | 144,141 | 3,053,210 |
| 2 | 3,263,848 | 607,514,297 | 80,390,118 | 39,618 | 141,818 | 3,051,850 |
| 3 | 3,323,641 | 561,553,077 | 78,958,229 | 45,923 | 164,050 | 2,972,811 |
| 4 | 3,251,173 | 520,696,293 | 77,087,346 | 29,000 | 165,045 | 2,863,212 |
| 5 | 3,259,501 | 461,737,466 | 75,545,993 | 54,218 | 178,318 | 2,773,522 |
| 6 | 3,332,268 | 443,689,477 | 73,595,608 | 38,955 | 168,031 | 2,774,186 |
| 7 | 3,290,426 | 409,149,917 | 71,663,815 | 37,296 | 184,622 | 2,630,011 |
| 8 | 3,389,076 | 375,439,634 | 69,682,029 | 44,264 | 180,641 | 2,614,748 |
| 9 | 3,320,986 | 346,313,863 | 67,570,182 | 42,936 | 192,586 | 2,575,659 |

Stability of og-luc clones

| Temp | Clone | 1/2 life |
|---|---|---|
| RT (22°C) | WT | 1 hour |
| RT (22°C) | og-luc C1 | 9.4 hours |
| RT (22°C) | Renilla | ~24 hours |
| 30°C | N166R | 30 minutes |
| 30°C | og-luc C1+A4E | No decay in 6 hours |
| 30°C | Renilla | 7.9 hours |
| 37°C | N166R | 2 min |
| 37°C | og-luc C1+A4E | no loss 3 hours |
| 42°C | og-luc C1+A4E | 6.4 hours |
| 54°C | og-luc C1 | 7.1 min |
| 54°C | og-luc C1+A4E | 8 (7.1, 7.7) min |
| 54°C | og-luc C1+C2+A4E | 128 min |
| 54°C | og-luc C1+C3+A4E | 23.7 min |

Figure 24

Mutations: C1+A4E random mutagenesis

| C1A4E random mutagenesis | AA change | Fold over C1A4E |
|---|---|---|
| 04g7 | L72Q | 3 |
| 10f2 | I90T | 1.9 |
| 16c5 | Q20R | 4.1 |
| 25a1 | C164S | 3.1 |
| 28b2 | V79I | 2.9 |
| 29h7 | F54I | 10.3 |
| 35d11 | K89E | 2.2 |

Figure 27A

Mutations: C1+A4E random mutagenesis

| Amino Acid change | Fold over C1+A4E |
|---|---|
| I90V | 1.5 |
| F77W | 2 |

Fig

Changes at position 92

| Amino Acid change | Fold over C1A4E (20uM coelenterazine) |
|---|---|
| L92G | 2.2 |
| L92Q | 2 |
| L92S | 2.9 |
| L92A | 2.5 |

FIG. 28

Combinations that improve light output

| Sample ID (Combination experiment) | Fold over C1A4E | Amino Acid change from C1A4E |
|---|---|---|
| 17A6 | 19.3 | F54I, F68S, I90V |
| 14A12 | 17.7 | F54I, M75K |
| 1G4 | 17.5 | F54I, M75K, I90V |
| 3C6 | 17.5 | F54I, F68S, M75K |
| 14B7 | 17.5 | F54I, I90V |

Signal Stability normalized by N166R

| Sample | Signal 1/2 life (minutes) RLAB normalized by N166R |
|---|---|
| T2T | 1.2 |
| T2T+N166R | 1.1 |
| A4E | 1.4 |
| Q11R | 1.1 |
| V44I | 1.0 |
| A54F | 0.8 |
| A54F+N166R | 0.9 |
| A54I | 1.3 |
| P115E | 1.0 |
| P115E+N166R | 1.0 |
| Y138I | 1.0 |
| Q124K | 1.1 |
| Y138C+N166R | 0.6 |
| I90V | 1.1 |
| A33K | 1.4 |
| F68Y | 1.2 |
| N166R/A33K | 1.0 |
| N166R/F68Y | 1.0 |

| Sample | Signal stability 0.5% tergitol buffer normalized by N166R |
|---|---|
| T2T | 0.9 |
| T2T+N166R | 1.3 |
| A4E | 0.9 |
| Q11R | 0.8 |
| V44I | 0.8 |
| A54F | 0.8 |
| A54F+N166R | 1.1 |
| A54I | 0.7 |
| P115E | 1.2 |
| P115E+N166R | 1.9 |
| Y138I | 0.9 |
| Q124K | 1.0 |
| Y138C+N166R | 1.5 |
| I90V | 0.9 |
| A33K | 0.8 |
| F68Y | 0.9 |
| N166R/A33K | 1.0 |
| N166R/F68Y | 1.0 |

Figure 33C

Stability at 22°C normalized by N166R

| Sample | stability (1/2 life at 22C) normalized to N166R |
|---|---|
| T2T | 0.7 |
| T2T+N166R | 1.1 |
| A4E | 0.6 |
| Q11R | 0.7 |
| V44I | 0.8 |
| A54F | 0.9 |
| A54F+N166R | 2.9 |
| A54I | 1.0 |
| P115E | 0.8 |
| P115E+N166R | 1.9 |
| Y138I | 0.9 |
| Q124K | 0.7 |
| Y138C+N166R | 0.6 |
| I90V | 0.7 |

Figure 33D

Summary

| Sample | Signal 1/2 life(mintes) 0.5% tergitol buffer normalized by N166R | Signal 1/2 life (minutes) RLAB normalized by N166R | Fold over N166R 0.5% tergitol assay buffer | Fold over N166R (RLAB) | stability (1/2 life at 22C) normalized to N166R |
|---|---|---|---|---|---|
| T2T | 0.9 | 1.2 | 1.6 | 0.6 | 0.7 |
| T2T+N166R | 1.3 | 1.1 | 2.3 | 1.8 | 1.1 |
| A4E | 0.9 | 1.4 | 1.2 | 0.5 | 0.6 |
| Q11R | 0.8 | 1.1 | 1.1 | 0.7 | 0.7 |
| V44I | 0.8 | 1.0 | 13.4 | 2.3 | 0.8 |
| A54F | 0.8 | 0.8 | 9.7 | 1.5 | 0.9 |
| A54F+N166R | 1.1 | 0.9 | 50.2 | 14.3 | 2.9 |
| A54I | 0.7 | 1.3 | 97.8 | 5.8 | 1.0 |
| P115E | 1.2 | 1.0 | 2.5 | 1.3 | 0.8 |
| P115E+N166R | 1.9 | 1.0 | 3.1 | 2.9 | 1.9 |
| Y138I | 0.9 | 1.0 | 7.0 | 2.6 | 0.9 |
| Q124K | 1.0 | 1.1 | 2.0 | 1.0 | 0.7 |
| Y138C+N166R | 1.5 | 0.6 | 3.7 | 2.8 | 0.6 |
| I90V | 0.9 | 1.1 | 2.4 | 0.8 | 0.7 |
| A33K | 0.8 | 1.4 | 2.6 | 0.6 | 0.9 |
| F68Y | 0.9 | 1.2 | 2.7 | 0.7 | 0.9 |
| N166R+ A33K | 1.0 | 1.0 | 6.3 | 2.0 | 1.1 |
| N166R +F68Y | 1.0 | 1.0 | 3.4 | 1.3 | 1.2 |

SEQUENCE LISTING

```
<160> NUMBER OF SEQ ID NOS: 34

<210> SEQ ID NO 1
<211> LENGTH: 169
<212> TYPE: PRT
<213> ORGANISM: Oplophorus gracilirostris

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 2
<211> LENGTH: 513
<212> TYPE: DNA
<213> ORGANISM: Artificial Sequence
<220> FEATURE:
<223> OTHER INFORMATION: Synthetic

<400> SEQUENCE: 2
atggtgttta cctttggcaga tttcgttgga gactggcaac agacagctgg atacaaccaa      60
gatcaagtgt tagaacaagg aggattgtct agtctgttcc aagccctggg agtgtcagtc     120
accccaatcc agaaagttgt gctgtctggg gagaatgggt taaaagctga tattcatgtc     180 atcatcccctt acgagggact cagtggtttt caaatgggtc tgattgaaat gatcttcaaa    240
gttgtttacc cagtggatga tcatcatttc aagattattc tccattatgg tacactcgtt     300
attgacggtg tgacaccaaa catgattgac tactttggac gcccttaccc tggaattgct     360
gtgtttgacg gcaagcagat cacagttact ggaactctgt ggaacggcaa caagatctat     420
gatgagcgcc tgatcaaccc agatggttca ctcctcttcc gcgttactat caatggagtc     480
```
accggatggc gcctttgcga gaacattctt gcc                                     513

<210> SEQ ID NO 3
<211> LENGTH: 131
<212> TYPE: PRT
<213> ORGANISM: Bos taurus

<400> SEQUENCE: 3

Ser Asn Lys Phe Leu Gly Thr Trp Lys Leu Val Ser Ser Glu Asn Phe
1               5                   10                  15

Asp Glu Tyr Met Lys Ala Leu Gly Val Gly Leu Ala Thr Arg Lys Leu
            20                  25                  30

Gly Asn Leu Ala Lys Pro Arg Val Ile Ile Ser Lys Lys Gly Asp Ile
        35                  40                  45

Ile Thr Ile Arg Thr Glu Ser Pro Phe Lys Asn Thr Glu Ile Ser Phe
    50                  55                  60

Lys Leu Gly Gln Glu Phe Glu Glu Thr Thr Ala Asp Asn Arg Lys Thr
65                  70                  75                  80

Lys Ser Thr Val Thr Leu Ala Arg Gly Ser Leu Asn Gln Val Gln Lys
                85                  90                  95

Trp Asn Gly Asn Glu Thr Thr Ile Lys Arg Lys Leu Val Asp Gly Lys
            100                 105                 110

Met Val Val Glu Cys Lys Met Lys Asp Val Val Cys Thr Arg Ile Tyr
        115                 120                 125

Glu Lys Val
    130

<210> SEQ ID NO 4
<211> LENGTH: 134
<212> TYPE: PRT
<213> ORGANISM: Rattus rattus

<400> SEQUENCE: 4

Pro Val Asp Phe Asn Gly Tyr Trp Lys Met Leu Ser Asn Glu Asn Phe
1               5                   10                  15

Glu Glu Tyr Leu Arg Ala Leu Asp Val Asn Val Ala Leu Arg Lys Ile
            20                  25                  30

Ala Asn Leu Leu Lys Pro Asp Lys Glu Ile Val Gln Asp Gly Asp His
        35                  40                  45

Met Ile Ile Arg Thr Leu Ser Thr Phe Arg Asn Tyr Ile Met Asp Phe
    50                  55                  60

Gln Val Gly Lys Glu Phe Glu Glu Asp Leu Thr Gly Ile Asp Asp Arg
65                  70                  75                  80

Lys Cys Met Thr Thr Val Ser Trp Asp Gly Asp Lys Leu Gln Cys Val
                85                  90                  95

Gln Lys Gly Glu Lys Glu Gly Arg Gly Trp Thr Gln Trp Ile Glu Gly
            100                 105                 110

Asp Glu Leu His Leu Glu Met Arg Ala Glu Gly Val Thr Cys Lys Gln
        115                 120                 125

Val Phe Lys Lys Val His
    130

<210> SEQ ID NO 5
<211> LENGTH: 135
<212> TYPE: PRT
<213> ORGANISM: Schistosoma mansoni

<400> SEQUENCE: 5

```
Gly Ser Met Ser Ser Phe Leu Gly Lys Trp Lys Leu Ser Glu Ser His
1               5                   10                  15

Asn Phe Asp Ala Val Met Ser Lys Leu Gly Val Ser Trp Ala Thr Arg
            20                  25                  30

Gln Ile Gly Asn Thr Val Thr Pro Thr Val Thr Phe Thr Met Asp Gly
        35                  40                  45

Asp Lys Met Thr Met Leu Thr Glu Ser Thr Phe Lys Asn Leu Ser Cys
    50                  55                  60

Thr Phe Lys Phe Gly Glu Glu Phe Asp Glu Lys Thr Ser Asp Gly Arg
65              70                  75                  80

Asn Val Lys Ser Val Val Glu Lys Asn Ser Glu Ser Lys Leu Thr Gln
                85                  90                  95

Thr Gln Val Asp Pro Lys Asn Thr Thr Val Ile Val Arg Glu Val Asp
            100                 105                 110

Gly Asp Thr Met Lys Thr Thr Val Thr Val Gly Asp Val Thr Ala Ile
        115                 120                 125

Arg Asn Tyr Lys Arg Leu Ser
    130                 135

<210> SEQ ID NO 6
<211> LENGTH: 135
<212> TYPE: PRT
<213> ORGANISM: Schistosoma mansoni

<400> SEQUENCE: 6

Gly Ser Met Ser Ser Phe Leu Gly Lys Trp Lys Leu Ser Glu Ser His
1               5                   10                  15

Asn Phe Asp Ala Val Met Ser Lys Leu Gly Val Ser Trp Ala Thr Arg
            20                  25                  30

Gln Ile Gly Asn Thr Val Thr Pro Thr Val Thr Phe Thr Met Asp Gly
        35                  40                  45

Asp Lys Met Thr Met Leu Thr Glu Ser Thr Phe Lys Asn Leu Ser Cys
    50                  55                  60

Thr Phe Lys Phe Gly Glu Glu Phe Asp Glu Lys Thr Ser Asp Gly Arg
65              70                  75                  80

Asn Val Lys Ser Val Val Glu Lys Asn Ser Glu Ser Lys Leu Thr Gln
                85                  90                  95

Thr Gln Val Asp Pro Lys Asn Thr Thr Val Ile Val Arg Glu Val Asp
            100                 105                 110

Gly Asp Thr Met Lys Thr Thr Val Thr Val Gly Asp Val Thr Ala Ile
        115                 120                 125

Arg Asn Tyr Lys Arg Leu Ser
    130                 135

<210> SEQ ID NO 7
<211> LENGTH: 165
<212> TYPE: PRT
<213> ORGANISM: Artificial Sequence
<220> FEATURE:
<223> OTHER INFORMATION: Synthetic

<400> SEQUENCE: 7

Leu Ala Asp Phe Val Gly Asp Trp Gln Gln Thr Ala Gly Tyr Asn Gln
1               5                   10                  15

Asp Gln Val Leu Glu Gln Gly Gly Leu Ser Ser Leu Phe Gln Ala Leu
            20                  25                  30
```

```
Gly Val Ser Val Thr Pro Ile Gln Lys Val Val Leu Ser Gly Glu Asn
            35                  40                  45

Gly Leu Lys Ala Asp Ile His Val Ile Ile Pro Tyr Glu Gly Leu Ser
 50                  55                  60

Gly Phe Gln Met Gly Leu Ile Glu Met Ile Phe Lys Val Val Tyr Pro
 65                  70                  75                  80

Val Asp Asp His His Phe Lys Ile Ile Leu His Tyr Gly Thr Leu Val
                 85                  90                  95

Ile Asp Gly Val Thr Pro Asn Met Ile Asp Tyr Phe Gly Arg Pro Tyr
            100                 105                 110

Pro Gly Ile Ala Val Phe Asp Gly Lys Gln Ile Thr Val Thr Gly Thr
            115                 120                 125

Leu Trp Asn Gly Asn Lys Ile Tyr Asp Glu Arg Leu Ile Asn Pro Asp
130                 135                 140

Gly Ser Leu Leu Phe Arg Val Thr Ile Asn Gly Val Thr Gly Trp Arg
145                 150                 155                 160

Leu Cys Glu Asn Ile
                165

<210> SEQ ID NO 8
<211> LENGTH: 131
<212> TYPE: PRT
<213> ORGANISM: Bos taurus

<400> SEQUENCE: 8

Ser Asn Lys Phe Leu Gly Thr Trp Lys Leu Val Ser Ser Glu Asn Phe
1               5                  10                  15

Asp Glu Tyr Met Lys Ala Leu Gly Val Gly Leu Ala Thr Arg Lys Leu
                20                  25                  30

Gly Asn Leu Ala Lys Pro Arg Val Ile Ile Ser Lys Lys Gly Asp Ile
            35                  40                  45

Ile Thr Ile Arg Thr Glu Ser Pro Phe Lys Asn Thr Glu Ile Ser Phe
 50                  55                  60

Lys Leu Gly Gln Glu Phe Glu Glu Thr Thr Ala Asp Asn Arg Lys Thr
65                  70                  75                  80

Lys Ser Thr Val Thr Leu Ala Arg Gly Ser Leu Asn Gln Val Gln Lys
                85                  90                  95

Trp Asn Gly Asn Glu Thr Thr Ile Lys Arg Lys Leu Val Asp Gly Lys
            100                 105                 110

Met Val Val Glu Cys Lys Met Lys Asp Val Val Cys Thr Arg Ile Tyr
            115                 120                 125

Glu Lys Val
130

<210> SEQ ID NO 9
<211> LENGTH: 134
<212> TYPE: PRT
<213> ORGANISM: Rattus rattus

<400> SEQUENCE: 9

Pro Val Asp Phe Asn Gly Tyr Trp Lys Met Leu Ser Asn Glu Asn Phe
1               5                  10                  15

Glu Glu Tyr Leu Arg Ala Leu Asp Val Asn Val Ala Leu Arg Lys Ile
                20                  25                  30

Ala Asn Leu Leu Lys Pro Asp Lys Glu Ile Val Gln Asp Gly Asp His
            35                  40                  45
```

```
Met Ile Ile Arg Thr Leu Ser Thr Phe Arg Asn Tyr Ile Met Asp Phe
    50                  55                  60

Gln Val Gly Lys Glu Phe Glu Asp Leu Thr Gly Ile Asp Asp Arg
65                  70                  75                  80

Lys Cys Met Thr Thr Val Ser Trp Asp Gly Asp Lys Leu Gln Cys Val
                85                  90                  95

Gln Lys Gly Glu Lys Glu Gly Arg Gly Trp Thr Gln Trp Ile Glu Gly
                100                 105                 110

Asp Glu Leu His Leu Glu Met Arg Ala Glu Gly Val Thr Cys Lys Gln
                115                 120                 125

Val Phe Lys Lys Val His
        130
```

<210> SEQ ID NO 10
<211> LENGTH: 196
<212> TYPE: PRT
<213> ORGANISM: Oplophorus gracilirostris

<400> SEQUENCE: 10

```
Met Ala Tyr Ser Thr Leu Phe Ile Ile Ala Leu Thr Ala Val Val Thr
1               5                   10                  15

Gln Ala Ser Ser Thr Gln Lys Ser Asn Leu Thr Phe Thr Leu Ala Asp
                20                  25                  30

Phe Val Gly Asp Trp Gln Gln Thr Ala Gly Tyr Asn Gln Asp Gln Val
                35                  40                  45

Leu Glu Gln Gly Gly Leu Ser Ser Leu Phe Gln Ala Leu Gly Val Ser
    50                  55                  60

Val Thr Pro Ile Gln Lys Val Val Leu Ser Gly Glu Asn Gly Leu Lys
65                  70                  75                  80

Ala Asp Ile His Val Ile Ile Pro Tyr Glu Gly Leu Ser Gly Phe Gln
                85                  90                  95

Met Gly Leu Ile Glu Met Ile Phe Lys Val Val Tyr Pro Val Asp Asp
                100                 105                 110

His His Phe Lys Ile Ile Leu His Tyr Gly Thr Leu Val Ile Asp Gly
                115                 120                 125

Val Thr Pro Asn Met Ile Asp Tyr Phe Gly Arg Pro Tyr Pro Gly Ile
    130                 135                 140

Ala Val Phe Asp Gly Lys Gln Ile Thr Val Thr Gly Thr Leu Trp Asn
145                 150                 155                 160

Gly Asn Lys Ile Tyr Asp Glu Arg Leu Ile Asn Pro Asp Gly Ser Leu
                165                 170                 175

Leu Phe Arg Val Thr Ile Asn Gly Val Thr Gly Trp Arg Leu Cys Glu
                180                 185                 190

Asn Ile Leu Ala
        195
```

<210> SEQ ID NO 11
<211> LENGTH: 131
<212> TYPE: PRT
<213> ORGANISM: Bos taurus

<400> SEQUENCE: 11

```
Ser Asn Lys Phe Leu Gly Thr Trp Lys Leu Val Ser Ser Glu Asn Phe
1               5                   10                  15

Asp Glu Tyr Met Lys Ala Leu Gly Val Gly Leu Ala Thr Arg Lys Leu
                20                  25                  30
```

Gly Asn Leu Ala Lys Pro Arg Val Ile Ile Ser Lys Lys Gly Asp Ile
            35                  40                  45

Ile Thr Ile Arg Thr Glu Ser Pro Phe Lys Asn Thr Glu Ile Ser Phe
 50                  55                  60

Lys Leu Gly Gln Glu Phe Glu Glu Thr Thr Ala Asp Asn Arg Lys Thr
 65                  70                  75                  80

Lys Ser Thr Val Thr Leu Ala Arg Gly Ser Leu Asn Gln Val Gln Lys
                 85                  90                  95

Trp Asn Gly Asn Glu Thr Thr Ile Lys Arg Lys Leu Val Asp Gly Lys
                100                 105                 110

Met Val Val Glu Cys Lys Met Lys Asp Val Val Cys Thr Arg Ile Tyr
                115                 120                 125

Glu Lys Val
    130

<210> SEQ ID NO 12
<211> LENGTH: 588
<212> TYPE: DNA
<213> ORGANISM: Oplophorus gracilirostris

<400> SEQUENCE: 12
atggcgtact ccactctgtt cataattgca ttgaccgccg ttgtcactca agcttcctca      60
actcaaaaat ctaacctaac ttttacgttg gcagatttcg ttggagactg gcaacagaca     120
gctggataca accaagatca agtgttagaa caaggaggat tgtctagtct gttccaagcc     180
ctgggagtgt cagtcacgcc catacagaaa gttgtactgt ctggggagaa tgggttaaaa     240
gctgatattc atgtcataat accttacgag ggactcagtg gttttcaaat gggtctaatt     300
gaaatgatct tcaaagttgt ttaccccgtg gatgatcatc atttcaagat tattctccat     360
tatggtacac tcgttattga cggtgtaaca cccaacatga ttgactactt tggaagacct     420
taccctggaa ttgctgtatt tgacggcaag cagatcacag ttactggaac tctgtggaac     480
ggcaacaaga tctatgatga gaggctaatc aaccctgatg gttcactcct cttcagagtt     540
actatcaatg gagtcacggg atggaggctt tgcgagaaca ttcttgcc                  588

<210> SEQ ID NO 13
<211> LENGTH: 171
<212> TYPE: PRT
<213> ORGANISM: Artificial Sequence
<220> FEATURE:
<223> OTHER INFORMATION: Synthetic

<400> SEQUENCE: 13

Met Val Phe Thr Leu Ala Asp Phe Val Gly Asp Trp Gln Gln Thr Ala
1               5                   10                  15

Gly Tyr Asn Gln Asp Gln Val Leu Glu Gln Gly Gly Leu Ser Ser Leu
                20                  25                  30

Phe Gln Ala Leu Gly Val Ser Val Thr Pro Ile Gln Lys Val Val Leu
            35                  40                  45

Ser Gly Glu Asn Gly Leu Lys Ala Asp Ile His Val Ile Ile Pro Tyr
 50                  55                  60

Glu Gly Leu Ser Gly Phe Gln Met Gly Leu Ile Glu Met Ile Phe Lys
 65                  70                  75                  80

Val Val Tyr Pro Val Asp Asp His His Phe Lys Ile Ile Leu His Tyr
                 85                  90                  95

Gly Thr Leu Val Ile Asp Gly Val Thr Pro Asn Met Ile Asp Tyr Phe
                100                 105                 110

Gly Arg Pro Tyr Pro Gly Ile Ala Val Phe Asp Gly Lys Gln Ile Thr
            115                 120                 125

Val Thr Gly Thr Leu Trp Asn Gly Asn Lys Ile Tyr Asp Glu Arg Leu
        130                 135                 140

Ile Asn Pro Asp Gly Ser Leu Leu Phe Arg Val Thr Ile Asn Gly Val
145                 150                 155                 160

Thr Gly Trp Arg Leu Cys Glu Asn Ile Leu Ala
                165                 170

<210> SEQ ID NO 14
<211> LENGTH: 513
<212> TYPE: DNA
<213> ORGANISM: Artificial Sequence
<220> FEATURE:
<223> OTHER INFORMATION: Synthetic

<400> SEQUENCE: 14
atggtgttta ccttggcaga tttcgttgga gactggcaac agacagctgg atacaaccaa    60
gatcaagtgt tagaacaagg aggattgtct agtctgttcc aagccctggg agtgtcagtc   120
accccaatcc agaaagttgt gctgtctggg gagaatgggt taaaagctga tattcatgtc   180
atcatccctt acgagggact cagtggtttt caaatgggtc tgattgaaat gatcttcaaa   240
gttgtttacc cagtggatga tcatcatttc aagattattc tccattatgg tacactcgtt   300
attgacggtg tgacaccaaa catgattgac tactttggac gcccttaccc tggaattgct   360
gtgtttgacg gcaagcagat cacagttact ggaactctgt ggaacggcaa caagatctat   420
gatgagcgcc tgatcaaccc agatggttca ctcctcttcc gcgttactat caatggagtc   480
accggatggc gcctttgcga gcgtattctt gcc                                513

<210> SEQ ID NO 15
<211> LENGTH: 171
<212> TYPE: PRT
<213> ORGANISM: Artificial Sequence
<220> FEATURE:
<223> OTHER INFORMATION: Synthetic

<400> SEQUENCE: 15

Met Val Phe Thr Leu Ala Asp Phe Val Gly Asp Trp Gln Gln Thr Ala
1               5                   10                  15

Gly Tyr Asn Gln Asp Gln Val Leu Glu Gln Gly Gly Leu Ser Ser Leu
            20                  25                  30

Phe Gln Ala Leu Gly Val Ser Val Thr Pro Ile Gln Lys Val Val Leu
        35                  40                  45

Ser Gly Glu Asn Gly Leu Lys Ala Asp Ile His Val Ile Ile Pro Tyr
    50                  55                  60

Glu Gly Leu Ser Gly Phe Gln Met Gly Leu Ile Glu Met Ile Phe Lys
65                  70                  75                  80

Val Val Tyr Pro Val Asp Asp His His Phe Lys Ile Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Pro Gly Ile Ala Val Phe Asp Gly Lys Gln Ile Thr
            115                 120                 125

Val Thr Gly Thr Leu Trp Asn Gly Asn Lys Ile Tyr Asp Glu Arg Leu
        130                 135                 140

Ile Asn Pro Asp Gly Ser Leu Leu Phe Arg Val Thr Ile Asn Gly Val

<210> SEQ ID NO 16
<211> LENGTH: 513
<212> TYPE: DNA
<213> ORGANISM: Artificial Sequence
<220> FEATURE:
<223> OTHER INFORMATION: Synthetic

<400> SEQUENCE: 16

```
atggtgttta cattggagga tttcgttgga gactggcggc agacagctgg atacaaccaa      60
gatcaagtgt tagaacaagg aggattgtct agtctgttcc aaaagctggg agtgtcagtc     120
accccaatcc agaaaattgt gctgtctggg gagaatgggt taaatttga tattcatgtc     180
atcatcccctt acgagggact cagtggtttt caaatgggtc tgattgaaat gatcttcaaa   240
gttgtttacc cagtgatga tcatcatttc aagattattc tccattatgg tacactcgtt     300
attgacggtg tgacaccaaa catgattgac tactttggac gcccttacga gggaattgct     360
gtgtttgacg gcaagaagat cacagttact ggaactctgt ggaacggcaa caagatcatt     420
gatgagcgcc tgatcaaccc agatggttca ctcctcttcc gcgttactat caatggagtc     480
accggatggc gcctttgcga gcgtattctt gcc                                   513
```

<210> SEQ ID NO 17
<211> LENGTH: 133
<212> TYPE: PRT
<213> ORGANISM: Locusta migratoria

<400> SEQUENCE: 17

```
Val Lys Glu Phe Ala Gly Ile Lys Tyr Lys Leu Asp Ser Gln Thr Asn
 1               5                  10                  15

Phe Glu Glu Tyr Met Lys Ala Ile Gly Val Gly Ala Ile Glu Arg Lys
                20                  25                  30

Ala Gly Leu Ala Leu Ser Pro Val Ile Glu Leu Glu Val Leu Asp Gly
            35                  40                  45

Asp Lys Phe Lys Leu Thr Ser Lys Thr Ala Ile Lys Asn Thr Glu Phe
        50                  55                  60

Thr Phe Lys Leu Gly Glu Glu Phe Asp Glu Asp Thr Leu Asp Gly Arg
 65                 70                  75                  80

Lys Val Lys Ser Ile Ile Thr Gln Asp Gly Pro Asn Lys Leu Val His
                85                  90                  95

Glu Gln Lys Gly Asp His Pro Thr Ile Ile Ile Arg Glu Phe Ser Lys
               100                 105                 110

Glu Gln Cys Val Ile Thr Ile Lys Leu Gly Asp Leu Val Ala Thr Arg
           115                 120                 125

Ile Tyr Lys Ala Gln
       130
```

<210> SEQ ID NO 18
<211> LENGTH: 125
<212> TYPE: PRT
<213> ORGANISM: Bufo arenarum

<400> SEQUENCE: 18

```
Ala Phe Asn Gly Thr Trp Asn Val Tyr Ala Gln Glu Asn Tyr Glu Asn
 1               5                  10                  15
```

```
Phe Leu Arg Thr Val Gly Leu Pro Glu Asp Ile Ile Lys Val Ala Lys
             20                  25                  30

Asp Val Asn Pro Val Ile Glu Ile Gln Asn Gly Asn Glu Phe Val
         35                  40                  45

Val Thr Ser Lys Thr Pro Lys Gln Thr His Ser Asn Ser Phe Thr Val
 50                  55                  60

Gly Lys Glu Ser Glu Ile Thr Ser Met Asp Gly Lys Lys Ile Lys Val
 65                  70                  75                  80

Thr Val Gln Leu Glu Gly Gly Lys Leu Ile Cys Lys Ser Asp Lys Phe
                 85                  90                  95

Ser His Ile Gln Glu Val Asn Gly Asp Glu Met Val Glu Lys Ile Thr
            100                 105                 110

Ile Gly Ser Ser Thr Leu Thr Arg Lys Ser Lys Arg Val
            115                 120                 125

<210> SEQ ID NO 19
<211> LENGTH: 134
<212> TYPE: PRT
<213> ORGANISM: Echinococcus granulosus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 19

Xaa Met Glu Ala Phe Leu Gly Thr Trp Lys Met Glu Lys Ser Glu Gly
 1               5                  10                  15

Phe Asp Lys Ile Met Glu Arg Leu Gly Val Asp Phe Val Thr Arg Lys
             20                  25                  30

Met Gly Asn Leu Val Lys Pro Asn Leu Ile Val Thr Asp Leu Gly Gly
         35                  40                  45

Gly Lys Tyr Lys Met Arg Ser Glu Ser Thr Phe Lys Thr Thr Glu Xaa
 50                  55                  60

Ser Phe Lys Leu Gly Glu Lys Phe Lys Glu Val Thr Pro Asp Ser Arg
 65                  70                  75                  80

Glu Val Ala Ser Leu Ile Thr Val Glu Asn Gly Val Met Lys His Glu
                 85                  90                  95

Gln Asp Asp Lys Thr Lys Val Thr Tyr Ile Glu Arg Val Val Glu Gly
            100                 105                 110

Asn Glu Leu Lys Ala Thr Val Lys Val Asp Glu Val Val Cys Val Arg
            115                 120                 125

Thr Tyr Ser Lys Val Ala
            130

<210> SEQ ID NO 20
<211> LENGTH: 190
<212> TYPE: PRT
<213> ORGANISM: Mycobacterium tuberculosis

<400> SEQUENCE: 20

Ala Ala Val Glu Arg Ala Lys Ala Thr Ala Ala Arg Asn Ile Pro Ala
 1               5                  10                  15

Phe Asp Asp Leu Pro Val Pro Ala Asp Thr Ala Asn Leu Arg Glu Gly
             20                  25                  30

Ala Asp Leu Asn Asn Ala Leu Leu Ala Leu Leu Pro Leu Val Gly Val
```

```
                      35                  40                  45
Trp Arg Gly Glu Gly Glu Gly Arg Gly Pro Asp Gly Asp Tyr Arg Phe
     50                  55                  60

Gly Gln Gln Ile Val Val Ser His Asp Gly Asp Tyr Leu Asn Trp
 65                  70                  75                  80

Glu Ser Arg Ser Trp Arg Leu Thr Ala Thr Gly Asp Tyr Gln Glu Pro
                 85                  90                  95

Gly Leu Arg Glu Ala Gly Phe Trp Arg Phe Val Ala Ile Glu Leu Leu
            100                 105                 110

Leu Ala His Ser Ala Gly Tyr Val Glu Leu Phe Tyr Gly Arg Pro Arg
        115                 120                 125

Thr Gln Ser Ser Trp Glu Leu Val Thr Asp Ala Leu Ala Arg Ser Arg
    130                 135                 140

Ser Gly Val Leu Val Gly Gly Ala Lys Arg Leu Tyr Gly Ile Val Glu
145                 150                 155                 160

Gly Gly Asp Leu Ala Tyr Val Glu Glu Arg Val Asp Ala Asp Gly Gly
                165                 170                 175

Leu Val Pro His Leu Ser Ala Arg Leu Ser Arg Phe Val Gly
            180                 185                 190

<210> SEQ ID NO 21
<211> LENGTH: 351
<212> TYPE: PRT
<213> ORGANISM: Lingulodinium polyedrum
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid

<400> SEQUENCE: 21

Glu Lys Gly Phe Glu Ala Gly Asp Asn Lys Leu Gly Gly Ala Leu Asn
 1               5                  10                  15

Ala Lys His Val Glu Lys Tyr Gly Asp Asn Phe Lys Asn Gly Xaa His
                20                  25                  30

Lys Pro Glu Phe His Glu Asp Gly Leu His Lys Pro Xaa Glu Val Gly
            35                  40                  45

Gly Lys Lys Phe Glu Ser Gly Phe His Tyr Leu Leu Glu Cys His Glu
        50                  55                  60

Leu Gly Gly Lys Asn Ala Ser Gly Gly Tyr Gly Gly Pro Leu Cys Glu
 65                  70                  75                  80
```

Asp Pro Tyr Gly Ser Glu Val Gln Ala Xaa Thr Glu Lys Leu Leu Lys
                85                  90                  95

Glu Ala Asp Ser Asp Arg Thr Leu Cys Phe Asn Asn Phe Gln Asp Pro
            100                 105                 110

Cys Pro Gln Leu Thr Lys Glu Gln Val Ala Xaa Cys Lys Gly Phe Asp
        115                 120                 125

Tyr Gly Asp Lys Thr Leu Lys Leu Pro Cys Gly Pro Leu Pro Trp Pro
    130                 135                 140

Ala Gly Leu Pro Glu Pro Gly Tyr Val Pro Lys Thr Asn Pro Leu His
145                 150                 155                 160

Gly Arg Trp Ile Thr Val Ser Gly Gly Gln Ala Ala Phe Ile Lys Glu
                165                 170                 175

Ala Ile Lys Ser Gly Met Leu Gly Ala Ala Glu Ala Asn Lys Ile Val
            180                 185                 190

Ala Asp Thr Asp His His Gln Thr Gly Gly Xaa Tyr Leu Arg Ile Asn
        195                 200                 205

Gln Phe Gly Asp Val Cys Thr Val Asp Ala Ser Val Ala Lys Phe Ala
    210                 215                 220

Arg Ala Lys Arg Thr Trp Lys Ser Gly His Tyr Phe Tyr Glu Pro Leu
225                 230                 235                 240

Val Ser Gly Gly Asn Leu Leu Gly Val Trp Val Leu Pro Glu Glu Tyr
                245                 250                 255

Arg Lys Ile Gly Phe Phe Trp Glu Xaa Glu Ser Gly Arg Cys Phe Arg
            260                 265                 270

Ile Glu Arg Arg Ala Phe Pro Val Gly Pro Tyr Thr Phe Xaa Arg Gln
        275                 280                 285

Ala Thr Glu Val Gly Gly Lys Ile Ser Phe Val Phe Tyr Val Lys Val
    290                 295                 300

Ser Asn Asp Pro Glu Ser Asp Pro Ile Pro Leu Gln Ser Arg Asp Tyr
305                 310                 315                 320

Thr Ala Leu Ala Gly Arg Asp Asn Ala Pro Thr Asn Leu Gly Lys Pro
                325                 330                 335

Tyr Pro Thr Leu Ala Lys Asp Leu Asp Tyr Pro Lys Lys Arg Asp
            340                 345                 350

<210> SEQ ID NO 22
<211> LENGTH: 131
<212> TYPE: PRT
<213> ORGANISM: Homo sapiens

<400> SEQUENCE: 22

Val Asp Ala Phe Leu Gly Thr Trp Lys Leu Val Asp Ser Lys Asn Phe
1               5                   10                  15

Asp Asp Tyr Met Lys Ser Leu Gly Val Gly Phe Ala Thr Arg Gln Val
            20                  25                  30

Ala Ser Met Thr Lys Pro Thr Thr Ile Ile Glu Lys Asn Gly Asp Ile
        35                  40                  45

Leu Thr Leu Lys Thr His Ser Thr Phe Lys Asn Thr Glu Ile Ser Phe
    50                  55                  60

Lys Leu Gly Val Glu Phe Asp Glu Thr Thr Ala Asp Asp Arg Lys Val
65                  70                  75                  80

Lys Ser Ile Val Thr Leu Asp Gly Gly Lys Leu Val His Leu Gln Lys
                85                  90                  95

Trp Asp Gly Gln Glu Thr Thr Leu Val Arg Glu Leu Ile Asp Gly Lys

```
                100               105               110
Leu Ile Leu Thr Leu Thr His Gly Thr Ala Val Cys Thr Arg Thr Tyr
        115               120               125

Glu Lys Glu
    130

<210> SEQ ID NO 23
<211> LENGTH: 171
<212> TYPE: PRT
<213> ORGANISM: Artificial Sequence
<220> FEATURE:
<223> OTHER INFORMATION: Synthetic

<400> SEQUENCE: 23

Met Val Phe Thr Leu Glu Asp Phe Val Gly Asp Trp Arg Gln Thr Ala
1               5                   10                  15

Gly Tyr Asn Gln Asp Gln Val Leu Glu Gln Gly Gly Leu Ser Ser Leu
            20                  25                  30

Phe Gln Lys Leu Gly Val Ser Val Thr Pro Ile Gln Lys Ile Val Leu
        35                  40                  45

Ser Gly Glu Asn Gly Leu Lys Phe Asp Ile His Val Ile Ile Pro Tyr
    50                  55                  60

Glu Gly Leu Ser Gly Phe Gln Met Gly Leu Ile Glu Met Ile Phe Lys
65                  70                  75                  80

Val Val Tyr Pro Val Asp Asp His His Phe Lys Ile Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 24
<211> LENGTH: 513
<212> TYPE: DNA
<213> ORGANISM: Artificial Sequence
<220> FEATURE:
<223> OTHER INFORMATION: Synthetic

<400> SEQUENCE: 24
atggtgttta cattggcaga tttcgttgga gactggcggc agacagctgg atacaaccaa        60
gatcaagtgt tagaacaagg aggattgtct agtctgttcc aaaagctggg agtgtcagtc       120
accccaatcc agaaaattgt gctgtctggg gagaatgggt taaatttga tattcatgtc       180 atcatccctt acgagggact cagtggtttt caaatgggtc tgattgaaat gatcttcaaa       240
gttgtttacc cagtggatga tcatcatttc aagattattc tccattatgg tacactcgtt       300
attgacggtg tgacaccaaa catgattgac tactttggac cccttacgag ggaattgct        360 gtgtttgacg gcaagaagat cacagttact ggaactctgt ggaacggcaa caagatcatt       420
gatgagcgcc tgatcaaccc agatggttca ctcctcttcc gcgttactat caatggagtc       480
accggatggc gcctttgcga gcgtattctt gcc                                    513
```

<210> SEQ ID NO 25
<211> LENGTH: 171
<212> TYPE: PRT
<213> ORGANISM: Artificial Sequence
<220> FEATURE:
<223> OTHER INFORMATION: Synthetic

<400> SEQUENCE: 25

```
Met Val Phe Thr Leu Ala Asp Phe Val Gly Asp Trp Arg Gln Thr Ala
1               5                   10                  15

Gly Tyr Asn Gln Asp Gln Val Leu Glu Gln Gly Leu Ser Ser Leu
            20                  25                  30

Phe Gln Lys Leu Gly Val Ser Val Thr Pro Ile Gln Lys Ile Val Leu
            35                  40                  45

Ser Gly Glu Asn Gly Leu Lys Phe Asp Ile His Val Ile Ile Pro Tyr
50                  55                  60

Glu Gly Leu Ser Gly Phe Gln Met Gly Leu Ile Glu Met Ile Phe Lys
65                  70                  75                  80

Val Val Tyr Pro Val Asp Asp His His Phe Lys Ile Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 26
<211> LENGTH: 513
<212> TYPE: DNA
<213> ORGANISM: Artificial Sequence
<220> FEATURE:
<223> OTHER INFORMATION: Synthetic

<400> SEQUENCE: 26

```
atggtgttta cattggcaga tttcgttgga gactggcggc agacagctgg atacaaccaa      60
gatcaagtgt tagaacaagg aggattgtct agtctgttcc aaaagctggg agtgtcagtc     120
accccaatcc agaaaattga gctgtctggg gagaatgggt taaatttga tattcatgtc      180 atcatccctt acgagggact cagtggtttt caaatgggtc tgattgaaat gatcttcaaa     240
gttgtttacc cagtgatga tcatcatttc aagattattc tccattatgg tacactcgtt      300
attgacggtg tgacacttaa catgattgac tactttggac gcccttacga gggaattgct     360
gtgtttgacg gcaagaagat cacagttact ggaactctgt ggaacggcaa gaagatcatt    420
gaggagcgcc tgatcaaccc agatggttca ctcctcttcc gcgttactat caatggagtc    480
accggatggc gcctttgcga gcgtgttctt gcc                                   513
```

<210> SEQ ID NO 27
<211> LENGTH: 171
<212> TYPE: PRT
<213> ORGANISM: Artificial Sequence
<220> FEATURE:
<223> OTHER INFORMATION: Synthetic

<400> SEQUENCE: 27

Met Val Phe Thr Leu Ala Asp Phe Val Gly Asp Trp Arg Gln Thr Ala
1               5                   10                  15

Gly Tyr Asn Gln Asp Gln Val Leu Glu Gln Gly Gly Leu Ser Ser Leu
            20                  25                  30

Phe Gln Lys Leu Gly Val Ser Val Thr Pro Ile Gln Lys Ile Glu Leu
        35                  40                  45

Ser Gly Glu Asn Gly Leu Lys Phe Asp Ile His Val Ile Ile Pro Tyr
    50                  55                  60

Glu Gly Leu Ser Gly Phe Gln Met Gly Leu Ile Glu Met Ile Phe Lys
65                  70                  75                  80

Val Val Tyr Pro Val Asp Asp His His Phe Lys Ile Ile Leu His Tyr
                85                  90                  95

Gly Thr Leu Val Ile Asp Gly Val Thr Leu Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Lys Lys Ile Ile Glu Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Val Leu Ala
                165                 170

<210> SEQ ID NO 28
<211> LENGTH: 513
<212> TYPE: DNA
<213> ORGANISM: Artificial Sequence
<220> FEATURE:
<223> OTHER INFORMATION: Synthetic

<400> SEQUENCE: 28

```
atggtgttta cattggagga tttcgttgga gactggcggc agacagctgg atacaaccaa    60
gatcaagtgt tagaacaagg aggattgtct agtctgttcc aaaagctggg agtgtcagtc   120
accccaatcc agaaaattga gctgtctggg gagaatgggt taaaatttga tattcatgtc   180
atcatccctt acgagggact cagtggtttt caaatgggtc tgattgaaat gatcttcaaa   240
gttgtttacc cagtggatga tcatcatttc aagattattc tccattatgg tacactcgtt   300
attgacggtg tgacacttaa catgattgac tactttggac gcccttacga gggaattgct   360
gtgtttgacg gcaagaagat cacagttact ggaactctgt ggaacggcaa gaagatcatt   420
gaggagcgcc tgatcaaccc agatggttca ctcctcttcc gcgttactat caatggagtc   480
accggatggc gcctttgcga gcgtgttctt gcc                                513
```

<210> SEQ ID NO 29
<211> LENGTH: 171
<212> TYPE: PRT
<213> ORGANISM: Artificial Sequence
<220> FEATURE:
<223> OTHER INFORMATION: Synthetic

<400> SEQUENCE: 29

Met Val Phe Thr Leu Glu Asp Phe Val Gly Asp Trp Arg Gln Thr Ala
1               5                   10                  15

Gly Tyr Asn Gln Asp Gln Val Leu Glu Gln Gly Gly Leu Ser Ser Leu
            20                  25                  30

Phe Gln Lys Leu Gly Val Ser Val Thr Pro Ile Gln Lys Ile Glu Leu
            35                  40                  45

Ser Gly Glu Asn Gly Leu Lys Phe Asp Ile His Val Ile Ile Pro Tyr
 50                  55                  60

Glu Gly Leu Ser Gly Phe Gln Met Gly Leu Ile Glu Met Ile Phe Lys
65                  70                  75                  80

Val Val Tyr Pro Val Asp Asp His Phe Lys Ile Ile Leu His Tyr
                85                  90                  95

Gly Thr Leu Val Ile Asp Gly Val Thr Leu Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Lys Lys Ile Ile Glu Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Val Leu Ala
                165                 170

<210> SEQ ID NO 30
<211> LENGTH: 513
<212> TYPE: DNA
<213> ORGANISM: Artificial Sequence
<220> FEATURE:
<223> OTHER INFORMATION: Synthetic

<400> SEQUENCE: 30
atggtgttta cattggagga tttcgttgga gactggcggc agacagctgg atacaaccaa      60
gatcaagtgt tagaacaagg aggattgcct agtctgttcc aaaagatggg agtgtcagtc     120
accccaatcc agaaaattgt gctgtctggg gagaatgtgt taaaatttga tattcatgtc     180
atcatccctt acgagggact cagtggtttt caaatgggtc tgattgaaat gatcttcaaa     240
gttgtttacc cagtggatga tcatcatttc aagattattc tccattatgg tacactcgtt     300
gttgacggtg tgacaccaaa catgattgac tactttggac gcccttacga gggaattgct     360
gtgtttgacg gcaagaagat cacagttact ggaactctgt ggaacggcaa caagatcatt     420
gatgagcgcc tgctcaaccc agatggttca ctcctcttcc gcgttactat caatggagtc     480
accggatggc gcctttgcga gcgtattctt gcc                                   513

<210> SEQ ID NO 31
<211> LENGTH: 171
<212> TYPE: PRT
<213> ORGANISM: Artificial Sequence
<220> FEATURE:
<223> OTHER INFORMATION: Synthetic

<400> SEQUENCE: 31

Met Val Phe Thr Leu Glu Asp Phe Val Gly Asp Trp Arg Gln Thr Ala
1               5                   10                  15

Gly Tyr Asn Gln Asp Gln Val Leu Glu Gln Gly Gly Leu Pro Ser Leu
            20                  25                  30

Phe Gln Lys Met Gly Val Ser Val Thr Pro Ile Gln Lys Ile Val Leu
        35                  40                  45

Ser Gly Glu Asn Val Leu Lys Phe Asp Ile His Val Ile Ile Pro Tyr
 50                  55                  60

Glu Gly Leu Ser Gly Phe Gln Met Gly Leu Ile Glu Met Ile Phe Lys
65                  70                  75                  80

Val Val Tyr Pro Val Asp Asp His His Phe Lys Ile Ile Leu His Tyr
                85                  90                  95

Gly Thr Leu Val Val Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Leu Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 32
<211> LENGTH: 513
<212> TYPE: DNA
<213> ORGANISM: Artificial Sequence
<220> FEATURE:
<223> OTHER INFORMATION: Synthetic

<400> SEQUENCE: 32
atggtgttta cattggcaga tttcgttgga gactggcaac agacagctgg atacaaccaa      60
gatcaagtgt tagaacaagg aggattgtct agtctgttcc aagccctggg agtgtcagtc     120
accccaatcc agaaagttgt gctgtctggg gagaatgggt taaaagctga tattcatgtc     180
atcatccctt acgagggact cagtggtttt caaatgggtc tgattgaaat gatcttcaaa     240
gttgtttacc cagtggatga tcatcatttc aagattattc tccattatgg tacactcgtt     300
attgacggtg tgacaccaaa catgattgac tactttggac gcccttaccc tggaattgct     360
gtgtttgacg gcaagcagat cacagttact ggaactctgt ggaacggcaa caagatctat     420
gatgagcgcc tgatcaaccc agatggttca ctcctcttcc gcgttactat caatggagtc     480
accggatggc gcctttgcga gaacattctt gcc                                  513

<210> SEQ ID NO 33
<211> LENGTH: 171
<212> TYPE: PRT
<213> ORGANISM: Artificial Sequence
<220> FEATURE:
<223> OTHER INFORMATION: Synthetic

<400> SEQUENCE: 33

Met Val Phe Thr Leu Ala Asp Phe Val Gly Asp Trp Arg Gln Thr Ala
1               5                   10                  15

Gly Tyr Asn Gln Asp Gln Val Leu Glu Gln Gly Gly Leu Ser Ser Leu
            20                  25                  30

Phe Gln Lys Leu Gly Val Ser Val Thr Pro Ile Gln Lys Ile Val Leu
        35                  40                  45

Ser Gly Glu Asn Gly Leu Lys Phe Asp Ile His Val Ile Ile Pro Tyr
    50                  55                  60

Glu Gly Leu Ser Gly Phe Gln Met Gly Leu Ile Glu Met Ile Phe Lys
65                  70                  75                  80

Val Val Tyr Pro Val Asp Asp His His Phe Lys Ile Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr

```
                 115                 120                 125
Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 34
<211> LENGTH: 513
<212> TYPE: DNA
<213> ORGANISM: Artificial Sequence
<220> FEATURE:
<223> OTHER INFORMATION: Synthetic

<400> SEQUENCE: 34
atggtgttta cattggcaga tttcgttgga gactggcggc agacagctgg atacaaccaa      60
gatcaagtgt tagaacaagg aggattgtct agtctgttcc aaaagctggg agtgtcagtc     120
accccaatcc agaaaattgt gctgtctggg gagaatgggt taaaatttga tattcatgtc     180
atcatccctt acgagggact cagtggtttt caaatgggtc tgattgaaat gatcttcaaa     240
gttgtttacc cagtggatga tcatcatttc aagattattc tccattatgg tacactcgtt     300
attgacggtg tgacaccaaa catgattgac tactttggac gcccttacga gggaattgct     360
gtgtttgacg gcaagaagat cacagttact ggaactctgt ggaacggcaa caagatcatt     420
gatgagcgcc tgatcaaccc agatggttca ctcctcttcc gcgttactat caatggagtc     480
accggatggc gcctttgcga gcgtattctt gcc                                  513
```

SYNTHETIC OPLOPHORUS LUCIFERASES WITH ENHANCED LIGHT OUTPUT

CROSS REFERENCE TO RELATED APPLICATIONS

This application is a continuation of U.S. patent application Ser. No. 15/714,210, filed Sep. 25, 2017, now allowed, which is a continuation of U.S. patent application Ser. No. 14/053,252, filed Oct. 14, 2013, now U.S. Pat. No. 9,777,311 which is a continuation of U.S. patent application Ser. No. 12/773,002, filed May 3, 2010, now U.S. Pat. No. 8,557,970, which claims priority to U.S. Provisional Application No. 61/174,838, filed May 1, 2009, each of which is incorporated herein by reference in its entirety.

BACKGROUND

The present invention relates to synthetic *Oplophorus* luciferases having enhanced properties compared to wild-type *Oplophorus* luciferase.

The deep-sea shrimp *Oplophorus gracilirostris* ejects a blue luminous cloud from the base of its antennae when stimulated, like various other luminescent decapod shrimps including those of the genera *Heterocarpus, Systellaspis* and *Acanthephyra* (Herring, J. Mar. Biol. Assoc. UK, 156:1029 (1976)). The mechanism underlying the luminescence of *Oplophorus* involves the oxidation of *Oplophorus* luciferin (coelenterazine) with molecular oxygen, which is catalyzed by *Oplophorus* luciferase as follows:

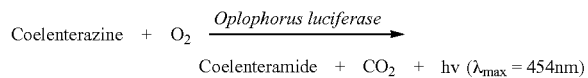

$$\text{Coelenterazine} + O_2 \xrightarrow{\textit{Oplophorus luciferase}} \text{Coelenteramide} + CO_2 + h\nu\ (\lambda_{max} = 454\text{nm})$$

Coelenterazine, an imidazopyrazinone compound, is involved in the bioluminescence of a wide variety of organisms as a luciferin or as the functional moiety of photoproteins. For example, the luciferin of the sea pansy *Renilla* is coelenterazine (Inoue et al., Tetrahed. Lett., 18:2685 (1977)), and the calcium-sensitive photoprotein aequorin from the jellyfish *Aequorea* also contains coelenterazine as its functional moiety (Shimomura et al., Biochem., 17:994 (1978); Head et al., Nature, 405:372 (2000)).

SUMMARY

In one embodiment, the invention provides a polynucleotide encoding a modified luciferase polypeptide. The modified luciferase polypeptide has at least 60% amino acid sequence identity to a wild-type *Oplophorus* luciferase and includes at least one amino acid substitution at a position corresponding to an amino acid in a wild-type *Oplophorus* luciferase of SEQ ID NO:1. The modified luciferase polypeptide has at least one of enhanced luminescence, enhanced signal stability, and enhanced protein stability relative to the wild-type *Oplophorus* luciferase.

In another embodiment, invention provides a polynucleotide encoding for a modified luciferase polypeptide. The modified luciferase polypeptide has enhanced luminescence relative to the wild-type *Oplophorus* luciferase and a substitution of at least one amino acid at position 2, 4, 11, 20, 23, 28, 33, 34, 44, 45, 51, 54, 68, 72, 75, 76, 77, 89, 90, 92, 99, 104, 115, 124, 135, 138, 139, 143, 144, 164, 166, 167, or 169 corresponding to SEQ ID NO:1.

Other aspects of the invention will become apparent by consideration of the detailed description and accompanying drawings.

BRIEF DESCRIPTION OF THE DRAWINGS

FIG. 3 shows an alignment of the amino acid sequences of OgLuc and various FABPs (SEQ ID NOs: 1, 3, 4, 5, and 17-20, respectively) based on 3D structure superimposition of FABPs.

FIGS. 5A-C summarize the average luminescence in RLU of the various OgLuc variants described in Example 7 ("Sample") at T=0 ("Average"), with standard deviation ("Stdev") and coefficient of variance ("CV") compared with WT OgLuc, using a 0.5% tergitol assay buffer.

FIGS. 7A-C summarize the average luminescence in RLU of the OgLuc variants ("Sample") at T=0 ("Average"), with standard deviation ("Stdev") and coefficient of variance ("CV") compared with WT OgLuc, using RLAB.

FIGS. 11A-B shows the signal half-life in minutes of the OgLuc variants compared to WT OgLuc determined from light output time course data shown in FIGS. 10A-C.

FIGS. 12A-B shows the protein stability at 22° C. as the half-life in minutes of the OgLuc variants compared to WT OgLuc.

FIGS. 15A-B shows the signal stability of the A33K and F68Y OgLuc variants compared to WT OgLuc, using 0.5% tergitol assay buffer. 15A) Light output time course of the A33K and F68Y OgLuc variants, with luminescence measured in RLU over time in minutes. 15B) Signal half-life in minutes of the A33K and F68Y OgLuc variants determined from light output time course data shown in FIG. 15A.

FIGS. 16A-B shows the signal stability of the A33K and F68Y OgLuc variants compared to WT OgLuc using RLAB. 16A) Light output time course of the A33K and F68Y OgLuc variants, with luminescence measured in RLU over time in minutes. 16B) Signal half-life in minutes of the A33K and F68Y OgLuc variants determined from light output time course data shown in FIG. 16A.

FIG. 17 shows the protein stability at 22° C. as the half-life in minutes of the A33K and F68Y OgLuc variants.

FIGS. 18A-B show the light output time course (i.e. signal stability) of the Core Combination OgLuc variants compared to the N166R OgLuc variant and *Renilla* luciferase, using 0.5% tergitol assay buffer, with luminescence measured in RLU over time in minutes.

FIG. 24 shows the shows the protein stability as the half-life in minutes of the C1, C1+A4E, C1+C2+A4E, and C1+C3+A4E OgLuc variants compared to WT OgLuc, *Renilla* luciferase and the N166R variant at various temperatures, such as 22, 37, 42, 50 and 54° C.

FIGS. 27A-B summarize the increase fold in luminescence at T=0 of the randomly mutagenized variants of C1+A4E ("sample ID") over the corresponding starting C1+A4E variant with the amino acid change indicated, using 0.5% tergitol buffer.

FIG. 28 summarizes the increase fold in luminescence at T=0 of the L92 variants of C1+A4E over the corresponding starting C1+A4E variant with the amino acid change indicated, using 0.5% tergitol buffer.

FIG. 29 summarizes the increase fold in luminescence at T=0 of the combination variants of C1+A4E ("Sample ID") over the corresponding starting C1+A4E variant with the amino acid changes indicated, using 0.5% tergitol buffer.

FIG. 31 shows the amino acid sequence alignment of SEQ ID NO:10 (NATIVE), SEQ ID NO:13 (Synthetic WT), SEQ ID NO:15 (N166R), SEQ ID NO:25 (C1), SEQ ID NO:27 (C1+C2), SEQ ID NO:23 (C1+A4E), SEQ ID NO:29 (C1+C2+A4E), and SEQ ID NO:31 (C1+C3+A4E) with the consensus sequence.

FIG. 33C summarizes the signal half-life in minutes of the OgLuc variants determined from the light output time course data shown in FIGS. 9A-C and 15B (0.5% tergitol assay buffer) and 10A-C and 16B (RLAB) normalized to the N166R variant.

FIG. 33D summarizes the protein stability at 22° C. as the half-life in minutes of the OgLuc variants compared to WT OgLuc shown in FIGS. 12A-B and 17 normalized to the N166R variant.

FIG. 33E summarizes the increase fold in luminescence, signal half-life and half-life at 22° C. shown in FIGS. 33A-D.

DETAILED DESCRIPTION

Figure 1:
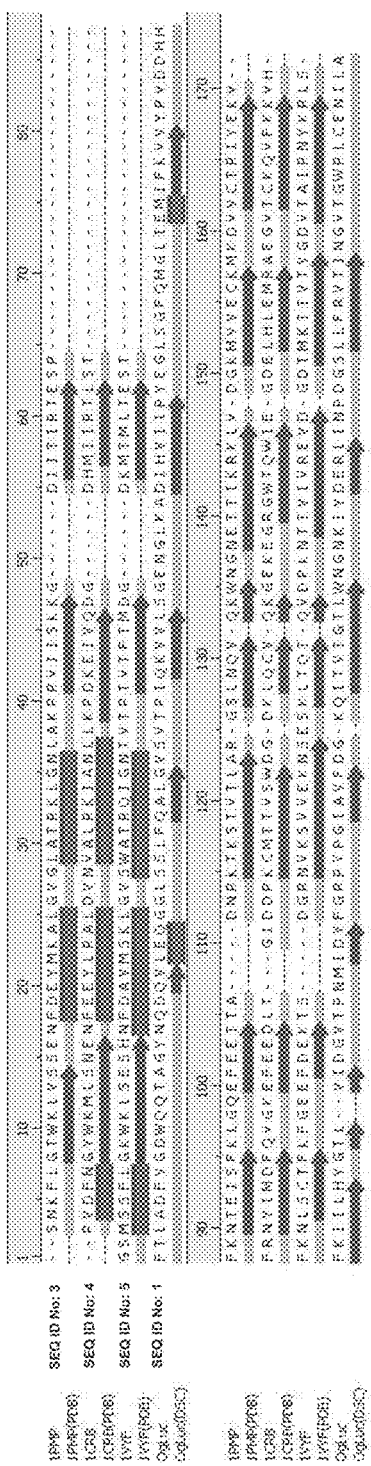
FIG. 1 shows secondary structure alignments of fatty acid binding proteins (FABPs) and OgLuc.

Before any embodiments of the invention are explained in detail, it is to be understood that the invention is not limited in its application to the details of structure, synthesis, and arrangement of components set forth in the following description or illustrated in the following drawings. The invention is described with respect to specific embodiments and techniques, however, the invention is capable of other embodiments and of being practiced or of being carried out in various ways.

In the following description of the methods of the invention, process steps are carried out at room temperature (about 22° C.) and atmospheric pressure unless otherwise specified. It also is specifically understood that any numerical range recited herein includes all values from the lower value to the upper value. For example, if a concentration range or beneficial effect range is stated as 1% to 50%, it is intended that values such as 2% to 40%, 10% to 30%, or 1% to 3%, etc. are expressly enumerated in this specification. Similarly, if a sequence identity range is given as between, e.g., 60% to <100%, it is intended that 65%, 75%, 90%, etc. are expressly enumerated in this specification. These are only examples of what is specifically intended, and all possible numerical values from the lowest value to the highest value are considered expressly stated in the application.

In embodiments of the present invention, various techniques as described herein were used to identify sites for amino acid substitution to produce an improved synthetic Oplophorus luciferase polypeptide. Additional techniques were used to optimize codons of the polynucleotides encoding for the various polypeptides in order to enhance expression of the polypeptides. It was found that making one or more amino acid substitutions, either alone or in various combinations, produced synthetic Oplophorus-type luciferases having at least one of enhanced luminescence, enhanced signal stability, and enhanced protein stability. Furthermore, including one or more codon optimizing substitutions in the polynucleotides which encode for the various polypeptides produced enhanced expression of the polypeptides in various eukaryotic and prokaryotic expression systems.

Luminescence refers to the light output of the luciferase polypeptide under appropriate conditions, e.g. in the presence of a suitable substrate such as a coelenterazine. The light output may be measured as an instantaneous or near-instantaneous measure of light output (which is sometimes referred to as "T=0" luminescence or "flash") upon start of the luminescence reaction, which may start upon addition of the coelenterazine substrate. The luminescence reaction in various embodiments is carried out in a solution containing lysate, for example from the cells in a prokaryotic or eukaryotic expression system; in other embodiments, expression occurs in an in vitro system or the luciferase protein is secreted into an extracellular medium, such that, in this latter case, it is not necessary to produce a lysate. In some embodiments, the reaction is started by injecting appropriate materials, e.g. coelenterazine, into a reaction chamber (e.g. a well of a multiwell plate such as a 96-well plate) containing the luciferase protein. The reaction chamber may be situated in a reading device which can measure the light output, e.g. using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or as the peak output.

Enhanced luminescence includes increased light output or luminescence, determined by suitable comparison of comparably-obtained measurements. As disclosed herein, one or more suitable amino acid substitutions to the synthetic Oplophorus luciferase sequence produce modified luciferase polypeptides which exhibit enhanced luminescence. Changes in the nucleotide sequence from the wild-type Oplophorus nucleotide sequence may contribute to enhanced luminescence by leading to an amino acid substitution and/or by enhancing protein expression.

Enhanced signal stability includes an increase in how long the signal from a luciferase continues to luminesce, for example, as measured by the half-life of decay of the signal in a time-course.

Enhanced protein stability includes increased thermal stability (e.g. stability at elevated temperatures) and chemical stability (e.g. stability in the presence of denaturants such as detergents, including e.g. Triton X-100).

The term "OgLuc" refers to the mature 19 kDa subunit of the Oplophorus luciferase protein complex, i.e. without a signal sequence; the native form of the mature OgLuc polypeptide sequence is given in SEQ ID NO:1. The term "OgLuc variant" refers to a synthetic OgLuc with one or more amino acid substitutions. For example, "OgLuc N166R variant" and "OgLuc+N166R" refers to a synthetic OgLuc which has an amino acid substitution of N to R at position 166 relative to SEQ ID NO:1. The terms "WT," "WT OgLuc," and "wild-type OgLuc" refer to synthetic, mature OgLuc protein encoded by a synthetic polynucleotide with ACC at position 2 relative to SEQ ID NO:1. The term "T2T" refers to a synthetic, mature OgLuc protein encoded by a synthetic polynucleotide with ACA at position 2 relative to SEQ ID NO:1. For the data presented below in the Examples, the wild-type protein that was synthesized is the synthetic wild-type protein of SEQ ID NO:13, which is encoded by the nucleotide sequence of SEQ ID NO:2.

The amino acid numbering used throughout this application to identify substituted residues is specified relative to the positions in the mature wild-type OgLuc polypeptide sequence of SEQ ID NO:1. The naturally-occurring wild-type OgLuc sequence may be initially synthesized with other amino acids which are later cleaved, resulting in the generation of a mature wild-type polypeptide such as shown in SEQ ID NO:1. For example, a signal sequence (e.g. to direct the nascent protein to a particular organelle such as the endoplasmic reticulum and/or to direct the protein for secretion) may be present at the beginning of the nascent protein and may then be cleaved to produce the mature wild-type protein.

The substrate specificity of Oplophorus luciferase is unexpectedly broad (Inouye and Shimomura. BBRC 223: 349(1997). For instance, bisdeoxycoelenterazine, an analogue of coelenterazine, is an excellent substrate for Oplophorus luciferase comparable to coelenterazine (Nakamura et al., Tetrahed. Lett., 38:6405 (1997)). Moreover, Oplophorus luciferase is a secreted enzyme, like the luciferase of the marine ostracod Cypridina (Vargula) hilgendorfii (Johnson and Shimomura, Meth. Enzyme, 57:331 (1978)), which also uses an imidazopyrazinone-type luciferin to emit light.

The molecular weight of Oplophorus luciferase was reported to be 130 kDa (by gel filtration) for the native protein complex, and 31 kDa after treatment with SDS (Shimomura et al., Biochem., 17:1994 (1978)). The luciferase also showed a molecular weight of approximately 106 kDa in gel filtration, and it was found that the molecule separates into 35 kDa and 19 kDa proteins upon sodium dodecyl sulfate-polyacrylamide gel electrophoresis (SDS-PAGE) analysis (Inouye et al., FEBS Lett., 481:19 (2000)). Inouye et al. (2000) reported the molecular cloning of the cDNAs encoding the 35 kDa and 19 kDa proteins, and the identification of the protein component that catalyzes the luminescence reaction. The cDNAs encoding the proteins were expressed in bacterial and mammalian cells as a 19 kDa protein which was capable of catalyzing the luminescent oxidation of coelenterazine (Inouye et al., 2000). The primary sequence of the 35 kDa protein revealed a leucine-rich repeat sequence, whereas the catalytic 19 kDa protein shared no homology with any known luciferases including various imidazopyrazinone luciferases (Inouye et al., 2000).

The 19 kDa protein (OgLuc) of *Oplophorus* luciferase appears to the smallest catalytic component having luciferase function and its primary structure has no significant homology with any reported luciferase including imidazopyrazinone luciferases (Lorenz et al., PNAS USA, 88:4438 (1991); Thompson et al., PNAS USA, 86:6567 (1989)). Inouye et al. (2000) reported that the overall amino acid sequence of the 19 kDa protein appears similar to that of an *E. coli* amine oxidase (757 amino acid residues; pir 140924) in the region of residues 217-392 (domain of D3-S1) (Parson et al. Structure 3:1171 (1995)), whereas the amino-terminal region (3-49) of the same protein is homologous to the amino-terminal region (1-47) of a fatty acid binding protein (132 amino acid residues; GenBank, L23322) (Becker et al., Gene, 148:321 (1994)).

Homology modeling requires the identification of at least one suitable 3D structure template, usually an experimentally determined 3D structure of a homologous protein with significant sequence similarity to the target protein. OgLuc does not have significant sequence similarity to other known proteins. Therefore, fold recognition methods designed to identify distant homologs of OgLuc, such as proteins with low sequence similarity to OgLuc, were employed. This approach yielded several potential 3D structure templates that belong to the protein family of fatty acid binding proteins (FABPs), which is part of the calycin protein superfamily. The model showed that the calycin fold structural signature, which effectively ties the N- and C-terminus together with hydrogen bonds, and which is present in at least three FABPs, is not completely conserved in OgLuc. OgLuc residue Asn166 (near the C-terminus) is unable to hydrogen bond with main chain carbonyls near the N-terminus. However, models of mutants containing either Arg or Lys at position 166 of OgLuc suggested that restoration of this structure motif could improve the structural stability of OgLuc and its expression/activity in cells.

Embodiments of the invention provide a synthetic, modified (variant) luciferase, as well as fragments thereof, for instance, those useful in complementation assays, having at least one amino acid substitution relative to a corresponding wild-type luciferase in a region that is structurally homologous to a member of the calycin protein superfamily, e.g., the family of fatty acid binding proteins. In one embodiment, the invention provides a modified crustacean luciferase, e.g., a modified decapod luciferase, as well as fragments thereof, for instance, those useful in complementation assays, having at least one amino acid substitution relative to a corresponding wild-type crustacean luciferase, in a region that is structurally homologous to a member of the calycin protein superfamily, e.g., the family of fatty acid binding proteins. In one embodiment, the invention provides a modified luciferase of a eukaryotic unicellular flagellate, as well as fragments thereof, for instance, those useful in complementation assays, having at least one amino acid substitution relative to a corresponding wild-type eukaryotic unicellular flagellate luciferase, e.g., luciferases from *Dinoflagellata* including Dinophyceae, Noctiluciphyceae, or Syndiniophycea, in a region that is structurally homologous to a member of the calycin protein superfamily, e.g., the family of fatty acid binding proteins. A nucleic acid molecule encoding the modified luciferase may or may not encode a secretory signal peptide linked to the modified luciferase.

The at least one substitution in the synthetic modified luciferase, or a fragment thereof, is to an amino acid residue at a corresponding position in the region that is structurally homologous to a member of the calycin protein superfamily, e.g., the family of fatty acid binding proteins, which residue may participate in intramolecular hydrogen or ionic bond formation, and is associated with enhanced luminescence, in the modified luciferase. Enhanced luminescence includes but is not limited to increased light emission, altered kinetics of light emission, e.g., greater stability of the light intensity, or altered luminescence color, e.g., a shift towards shorter or longer wavelengths, or a combination thereof. In one embodiment, the residue in the synthetic modified luciferase at the corresponding position may interact with a residue in a region corresponding to residues 1 to 10 or 144 to 148 of OgLuc, e.g., one having SEQ ID NO:1 (note that the numbering of those positions is based on a Phe at residue 1 of the mature sequence not a Met; however, other residues may precede the Phe such as a Val at position −1 which may be introduced by insertion of a cloning site) or a residue with atoms that are within 4 to 8 Å, e.g., within 6 Å, of the residue at the corresponding position (position 166). Corresponding positions may be identified by aligning sequences using, for instance, sequence alignment programs, secondary structure prediction programs or fold recognition methods, or a combination thereof. The modified luciferase in accordance with the invention may include additional amino acid substitutions that alter the color of luminescence, for example, substitution(s) that result in red-shifted luminescence, alter signal stability, alter protein stability, or any combination thereof.

In one embodiment, the invention provides a modified decapod luciferase which has enhanced luminescence relative to a corresponding wild-type decapod luciferase. In another embodiment, the invention provides a modified decapod luciferase which utilizes coelenterazine. Coelenterazines include but are not limited to naturally occurring coelenterazines as well as derivatives (analogs) thereof, such as those disclosed in U.S. Pat. No. 7,118,878, as well as EnduRen, ViviRen, coelenterazine n, coelenterazine h, coelenterazine c, coelenterazine cp, coelenterazine e, coelenterazine f, coelenterazine fcp, coelenterazine hh, coelenterazine i, coelenterazine icp, 2-methyl coelenterazine, and those disclosed in WO/040100 and U.S. application Ser. No. 12/056,073, the disclosures of which are incorporated by reference herein.

The modified luciferase in accordance with the invention has a residue other than asparagine at a position corresponding to residue 166 in SEQ ID NO:1 that results in the enhanced luminescence and optionally an aspartic acid at a position corresponding to residue 5 in SEQ ID NO:1, a glycine at a position corresponding to residue 8 in SEQ ID NO:1, an aspartic acid at a position corresponding to residue 9 in SEQ ID NO:1, a tryptophan, tyrosine or phenylalanine at a position corresponding to residue 10 in SEQ ID NO:1, an asparagine at a position corresponding to residue 144 in SEQ ID NO:1, and/or a glycine at a position corresponding to residue 147 in SEQ ID NO:1, or any combination thereof. In one embodiment, the residue in the modified luciferase corresponding to residue 166 in SEQ ID NO:1 is lysine. In another embodiment, the residue in the modified luciferase corresponding to residue 166 in SEQ ID NO:1 is arginine. In one embodiment, the residue in the modified luciferase corresponding to residue 166 in SEQ ID NO:1 is capable of forming one or more intramolecular hydrogen or ionic bonds with carbonyls or the side chain at a position corresponding to residue 9 in SEQ ID NO:1 near the N-terminus of the modified luciferase. In one embodiment, the modified luciferase lacks a signal peptide sequence. In one embodiment, the modified luciferase has at least 60%, e.g., at least 65%, 70%, 75%, 80%, 85%, 90%, 95%, 96%, 97%, 98%, or 99%, but less than 100%, amino acid sequence identity to SEQ ID NO:1.

In one embodiment, the corresponding wild-type luciferase is an *Oplophorus* luciferase, e.g., *Oplophorus gracilirostris, Oplophorus grimaldii, Oplophorus spinicauda, Oplophorus foliaceus, Oplophorus noraezeelandiae, Oplophorus typus, Oplophorus noraezelandiae* or *Oplophorus spinous, Heterocarpus* luciferase, *Systellapis* luciferase or an *Acanthephyra* luciferase. In one embodiment, the modified luciferase has at least a 2-fold or more, e.g., at least 4-fold, increased luminescence emission in a prokaryotic cell and/or an eukaryotic cell relative to the corresponding wild-type luciferase.

In another embodiment, the invention provides a modified dinoflagellate luciferase which has enhanced luminescence relative to a corresponding wild-type dinoflagellate luciferase, e.g., a dinoflagellate luciferase such as a *Lingulodinium polyedrum* luciferase, a *Pyrocystis lunula* luciferase or one having SEQ ID NO:21. The modified luciferase may have a residue other than asparagine at a position corresponding to residue 166 in SEQ ID NO:1, e.g., an arginine, and optionally a proline at a position corresponding to residue 5 in SEQ ID NO:1, a glycine at a position corresponding to residue 8 in SEQ ID NO:1, an arginine at a position corresponding to residue 9 in SEQ ID NO:1, a tryptophan, tyrosine or phenylalanine at a position corresponding to residue 10 in SEQ ID NO:1, a phenylalanine at a position corresponding to residue 144 in SEQ ID NO:1, and/or a threonine at a position corresponding to residue 147 in SEQ ID NO:1, or any combination thereof. In one embodiment, the residue in the modified luciferase corresponding to residue 166 in SEQ ID NO:1 is lysine. In another embodiment, the residue in modified luciferase corresponding to residue 166 in SEQ ID NO:1 is arginine. In one embodiment, the residue in the modified luciferase corresponding to residue 166 in SEQ ID NO:1 is capable of forming one or more intramolecular hydrogen or ionic bonds with carbonyls or the side chain at a position corresponding to residue 9 in SEQ ID NO:1 near the N-terminus of modified luciferase. In one embodiment, the modified luciferase lacks a signal peptide sequence.

In one embodiment, the modified luciferase has at least 60%, e.g., at least 65%, 70%, 75%, 80%, 85%, 90%, 95%, 96%, 97%, 98%, or 99%, but less than 100%, amino acid sequence identity to SEQ ID NO:21. The modified luciferase of the invention, including one with additional amino acid substitutions that alter the color of luminescence, may be employed with a modified luciferin in a luminogenic reaction that produces an altered luminescence color.

Further provided is a modified luciferase having a FABP beta-barrel related 3D structural domain, which modified luciferase has a substitution that results in the noncovalent joining, e.g., via intramolecular hydrogen or ionic bonds, of the terminal beta sheets of the beta barrel, and optionally additional noncovalent bonds, e.g., via intramolecular hydrogen or ionic bonds, with adjacent secondary structures.

Embodiments of the invention also provide a modified decapod or dinoflagellate luciferase which has enhanced luminescence and an arginine, lysine, alanine, leucine, proline, glutamine or serine at a position corresponding to residue 166 in SEQ ID NO:1 and at least one amino acid substitution relative to a corresponding wild-type decapod or dinoflagellate luciferase. In one embodiment, the at least one amino acid substitution in the modified luciferase is a substitution at a position corresponding to residue 4, 11, 33, 44, 45, 54, 75, 104, 115, 124, 135, 138, 139, 167, or 169, or a combination thereof, in SEQ ID NO:1, e.g., one which results in enhanced luminescence relative to a modified luciferase which has enhanced luminescence and an arginine, lysine, alanine, leucine, proline, glutamine or serine at a position corresponding to residue 166 in SEQ ID NO:1.

In one embodiment, the modified luciferase of the invention has one or more heterologous amino acid sequences at the N-terminus, C-terminus, or both (a fusion polypeptide such as one with an epitope or fusion tag), which optionally directly or indirectly interact with a molecule of interest. In one embodiment, the presence of the heterologous sequence (s) does not substantially alter the luminescence of the modified luciferase either before or after the interaction with the molecule of interest. In one embodiment, the heterologous amino acid sequence is an epitope tag. In another embodiment, the heterologous amino acid sequence is one which, during or after interaction with a molecule of interest, undergoes a conformational change, which in turn alters the activity of the luciferase, e.g., a modified OgLuc with such an amino acid sequence is useful to detect allosteric interactions. The modified luciferase or a fusion with the modified luciferase or a fragment thereof may be employed as a reporter.

In one embodiment, a fragment of a luciferase of the invention is fused to a heterologous amino acid sequence, the fusion thereby forming a beta-barrel, which fusion protein is capable of generating luminescence from a naturally occurring luciferin or a derivative thereof.

Also provided is a polynucleotide encoding a modified luciferase of the invention or a fusion thereof, an isolated host cell having the polynucleotide or the modified luciferase or a fusion thereof, and methods of using the polynucleotide, modified luciferase or a fusion thereof or host cell of the invention.

Further provided is a method to identify amino acid positions in a protein of interest which are in different secondary structures, e.g., structures separated by 5 amino acids or more that are not part of either secondary structure, and are capable of hydrogen or ionic bond formation with each other. The method includes comparing secondary structures predicted for the amino acid sequence of a protein of interest to secondary structures of one or more proteins without overall sequence similarly, e.g., less than 30% identity to the protein of interest. The one or more proteins have a defined 3D structure and at least one of the proteins has a first residue associated with at least one first secondary structure which forms a hydrogen or ionic bond, e.g., salt bridges, between side chains or between a side chain of or a main chain carbonyl near or within 5 or 10 residues of a second residue associated with a second secondary structure, respectively. In one embodiment, the first secondary structure is C-terminal to the second secondary structure. In another embodiment, the first secondary structure is N-terminal to the second secondary structure. Then it is determined whether the protein of interest has one or more secondary structures corresponding to at least the first secondary structure in the one or more proteins and if so determining amino acid positions in the protein of interest that correspond to the first residue, the second residue, or both, in the one or more proteins. In one embodiment, one secondary structure is a $3_{10}$ helix or a beta-barrel. In one embodiment, the protein of interest is a luciferase. In one embodiment, the first residue is capable of forming a hydrogen or ionic bond to one or more main chain carbonyls within 5 residues of the second residue. In one embodiment, the one or more proteins are fatty acid binding proteins.

Definitions

Amino acid residues in the modified luciferases of the invention may be those in the L-configuration, the D-configuration or nonnaturally occurring amino acids such as norleucine, L-ethionine, β-2-thienylalanine, 5-methyltryptophan norvaline, L-canavanine, p-fluorophenylalAnine, p-(4-hydroxybenzoyl)phenylalanine, 2-keto-4-(methylthio)butyric acid, beta-hydroxy leucine, gamma-chloronorvaline, gamma-methyl D-leucine, beta-D-L hydroxyleucine, 2-amino-3-chlorobutyric acid, N-methyl-D-valine, 3,4-difluoro-L-phenylalanine, 5,5,5-trifluoroleucine, 4,4,4,-trifluoro-L-valine, 5-fluoro-L-tryptophan, 4-azido-L-phenylalanine, 4-benzyl-L-phenylalanine, thiaproline, 5,5,5-trifluoroleucine, 5,5,5,5',5',5'-hexafluoroleucine, 2-amino-4-methyl-4-pentenoic acid, 2-amino-3,3,3-trifluoromethylpentanoic acid, 2-amino-3-methyl-5,5,5-trifluoropentanoic acid, 2-amino-3-methyl-4-pentenoic acid, trifluorovaline, hexafluorovaline, homocysteine, hydroxylysine, ornithine, and those with peptide linkages optionally replaced by a linkage such as, —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art. In keeping with standard polypeptide nomenclature, abbreviations for naturally occurring amino acid residues are as shown in the following Table of Correspondence.

| TABLE OF CORRESPONDENCE | | |
| --- | --- | --- |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

Enhanced luminescence, as used herein, may include any of the following: increased light emission, altered kinetics of light emission, e.g., greater stability of the light intensity, or altered luminescence color, e.g., a shift towards shorter or longer wavelengths.

The term "homology" refers to a degree of complementarity between two or more sequences. There may be partial homology or complete homology (i.e., identity). Homology is often measured using sequence analysis software (e.g., "GCG" and "Seqweb" Sequence Analysis Software Package formerly sold by the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a nucleic acid or a polypeptide, as in "isolated oligonucleotide", "isolated polynucleotide", "isolated protein", or "isolated polypeptide" refers to a nucleic acid or amino acid sequence that is identified and separated from at least one contaminant with which it is ordinarily associated in its source. Thus, an isolated nucleic acid or isolated polypeptide is present in a form or setting that is different from that in which it is found in nature. In contrast, non-isolated nucleic acids (e.g., DNA and RNA) or non-isolated polypeptides (e.g., proteins and enzymes) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., a single-stranded nucleic acid), but may contain both the sense and anti-sense strands (i.e., a double-stranded nucleic acid).

The term "nucleic acid molecule," "polynucleotide" or "nucleic acid sequence" as used herein, refers to nucleic acid, DNA or RNA that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

"*Oplophorus* luciferase" is a complex of native 35 kDa and 19 kDa proteins. The 19 kDa protein is the smallest catalytic component (GenBank accession BAB13776, 196 amino acids). As used herein, OgLuc is the 19 kDa protein without signal peptide (169 amino acids, residues 28 to 196 of BAB13776).

By "peptide," "protein" and "polypeptide" is meant any chain of amino acids, regardless of length or post-translational modification (e.g., glycosylation or phosphorylation). The nucleic acid molecules of the invention encode a variant of a naturally-occurring protein or polypeptide fragment thereof, which has an amino acid sequence that is at least 60%, e.g., at least 65%, 70%, 75%, 80%, 85%, 90%, 95%, 96%, 97%, 98%, or 99%, but less than 100%, amino acid sequence identity to the amino acid sequence of the naturally-occurring (native or wild-type) protein from which it is derived. The term "fusion polypeptide" or "fusion protein" refers to a chimeric protein containing a reference protein (e.g., luciferase) joined at the N- and/or C-terminus to one or more heterologous sequences (e.g., a non-luciferase polypeptide).

Protein primary structure (primary sequence, peptide sequence, protein sequence) is the sequence of amino acids. It is generally reported starting from the amino-terminal (N)

end to the carboxyl-terminal (C) end. Protein secondary structure can be described as the local conformation of the peptide chain, independent of the rest of the protein. There are 'regular' secondary structure elements (e.g., helices, sheets or strands) that are generally stabilized by hydrogen bond interactions between the backbone atoms of the participating residues, and 'irregular' secondary structure elements (e.g., turns, bends, loops, coils, disordered or unstructured segments). Protein secondary structure can be predicted with different methods/programs, e.g., PSIPRED (McGuffin et al., Bioinformatics, 16:404 (2000)), PORTER (Pollastri et al., Bioinformatics, 21:1719 (2005)), DSC (King and Sternberg, Protein Sci, 5:2298 (1996)), see www.expasy.org/tools/#secondary for a list. Protein tertiary structure is the global three-dimensional (3D) structure of the peptide chain. It is described by atomic positions in three-dimensional space, and it may involve interactions between groups that are distant in primary structure. Protein tertiary structures are classified into folds, which are specific three-dimensional arrangements of secondary structure elements. Sometimes there is no discernable sequence similarity between proteins that have the same fold.

The term "wild-type" or "native" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics when compared to the wild-type gene or gene product.

I. Exemplary Polynucleotides and Proteins

The invention includes a modified luciferase or protein fragments thereof, e.g., those with deletions, for instance a deletion of 1 to about 5 residues, and chimeras (fusions) thereof (see U.S. application Ser. Nos. 60/985,585 and 11/732,105, the disclosures of which are incorporated by reference herein) having at least one amino acid substitution relative to a wild-type luciferase, which substitution results in the modified luciferase having enhanced stability, enhanced luminescence, e.g., increased luminescence emission, greater stability of the luminescence kinetics, or altered luminescence color, or both. The luciferase sequences of a modified luciferase are substantially the same as the amino acid sequence of a corresponding wild-type luciferase. A polypeptide or peptide having substantially the same sequence means that an amino acid sequence is largely, but is not entirely, the same and retains the functional activity of the sequence to which it is related. In general, two amino acid sequences are substantially the same or substantially homologous if they are at least 60%, e.g., at least 65%, 70%, 75%, 80%, 85%, 90%, 95%, 96%, 97%, 98%, or 99%, but less than 100%, amino acid sequence identity. In one embodiment, the modified luciferase is encoded by a recombinant polynucleotide.

Homology or identity may be often measured using sequence analysis software. Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted by the local homology algorithm of Smith et al. (1981), by the homology alignment algorithm of Needleman et al. (J. Mol. Biol., 48:443 (1970), by the search for similarity method of Person et al. (Proc. Natl. Acad. Sci. USA, 85, 2444 (1988)), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al., CABIOS, 5:157 (1989); Corpet et al., Nucl. Acids Res., 16:1088 (1988); Huang et al., CABIOS, 8:155 (1992); and Pearson et al., Methods Mol. Biol., 24:307 (1994). The ALIGN program is based on the algorithm of Myers and Miller, LABIOS, 4:11 (1988). The BLAST programs of Altschul et al. (J. Mol. Biol., 215:403 (1990)) are based on the algorithm of Karlin and Altschul (PNAS USA, 90:5873 (1993)).

Software for performing BLAST analyses is publicly available through the National Center for Biotechnology information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol., 215:403 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin and Altschul, PNAS USA, 90:5873 (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (Nuc. Acids Res., 25:3389 (1997)). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, PNAS USA, 89:10915 (1989)). See "www.ncbi.nlm.nih.gov."

In particular, a polypeptide may be substantially related to another (reference) polypeptide but for a conservative or nonconservative variation. A conservative variation denotes the replacement of an amino acid residue by another, biologically similar residue including naturally occurring or nonnaturally occurring amino acid residues. Examples of conservative variations include the substitution of one hydrophobic residue such as isoleucine, valine, leucine or methionine for another, or the substitution of one polar residue for another such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. A modified luciferase of the invention has a conservative or a nonconservative substitution which results in enhanced stability, luminescence, or both.

The modified luciferase proteins or fusion proteins of the invention may be prepared by recombinant methods or by solid phase chemical peptide synthesis methods. Such methods are known in the art.

II. Vectors and Host Cells Encoding the Modified Luciferase or Fusions Thereof

Once a desirable nucleic acid molecule encoding a modified luciferase, a fragment thereof, such as one with luminescence activity or which may be complemented by another molecule to result in luminescence activity, or a fusion thereof with luminescence activity, is prepared, an expression cassette encoding the modified luciferase, a fragment thereof, e.g., one for complementation, or a fusion thereof with luminescence activity, may be prepared. For example, a nucleic acid molecule comprising a nucleic acid sequence encoding a modified luciferase is optionally operably linked to transcription regulatory sequences, e.g., one or more enhancers, a promoter, a transcription termination sequence or a combination thereof, to form an expression cassette. The nucleic acid molecule or expression cassette may be introduced to a vector, e.g., a plasmid or viral vector, which optionally includes a selectable marker gene, and the vector introduced to a cell of interest, for example, a prokaryotic cell such as $E.$ $coli$, $Streptomyces$ spp., $Bacillus$ spp., $Staphylococcus$ spp. and the like, as well as eukaryotic cells including a plant (dicot or monocot), fungus, yeast, e.g., $Pichia$, $Saccharomyces$ or $Schizosaccharomyces$, or a mammalian cell, lysates thereof, or to an in vitro transcription/translation mixture. Mammalian cells include but are not limited to bovine, caprine, ovine, canine, feline, non-human primate, e.g., simian, and human cells. Mammalian cell lines include, but are not limited to, CHO, COS, 293, HeLa, CV-1, SH-SY5Y, HEK293, and NIH3T3 cells.

The expression of an encoded modified luciferase may be controlled by any promoter capable of expression in prokaryotic cells or eukaryotic cells including synthetic promoters. Prokaryotic promoters include, but are not limited to, SP6, T7, T5, tac, bla, trp, gal, lac or maltose promoters, including any fragment that has promoter activity. Eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE, including any fragment that has promoter activity. The nucleic acid molecule, expression cassette and/or vector of the invention may be introduced to a cell by any method including, but not limited to, calcium-mediated transformation, electroporation, microinjection, lipofection and the like.

III. Optimized Sequences, and Vectors and Host Cells Encoding the Modified Luciferase Also provided is an isolated nucleic acid molecule (polynucleotide) comprising a nucleic acid sequence encoding a modified luciferase of the invention, a fragment thereof or a fusion thereof. In one embodiment, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. Such optimized sequences can produced enhanced expression, e.g. increased levels of protein expression, when introduced into a host cell.

In one embodiment, the polynucleotide includes a nucleic acid sequence encoding a modified luciferase of the invention, which nucleic acid sequence is optimized for expression in a mammalian host cell. In one embodiment, an optimized polynucleotide no longer hybridizes to the corresponding non-optimized sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids that are not completely complementary to one another be hybridized or annealed together. The art knows well that numerous equivalent conditions can be employed to comprise medium or low stringency conditions.

In another embodiment, the polynucleotide has less than 90%, e.g., less than 80%, nucleic acid sequence identity to the corresponding non-optimized sequence and optionally encodes a polypeptide having at least 60%, e.g., at least 65%, 70%, 75%, 80%, 85%, 90%, 95%, 96%, 97%, 98%, or 99%, but less than 100%, amino acid sequence identity with the polypeptide encoded by the non-optimized sequence. Constructs, e.g., expression cassettes, and vectors comprising the isolated nucleic acid molecule, e.g., with optimized nucleic acid sequence, as well as kits comprising the isolated nucleic acid molecule, construct or vector are also provided.

A nucleic acid molecule comprising a nucleic acid sequence encoding a modified luciferase of the invention, a fragment thereof or a fusion thereof is optionally optimized for expression in a particular host cell and also optionally operably linked to transcription regulatory sequences, e.g., one or more enhancers, a promoter, a transcription termination sequence or a combination thereof, to form an expression cassette.

In one embodiment, a nucleic acid sequence encoding a modified luciferase of the invention, a fragment thereof or a fusion thereof is optimized by replacing codons, e.g., at least 25% of the codons, in a wild type luciferase sequence with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Thus, the optimized nucleic acid product may have an improved level of expression due to improved codon usage frequency, and a reduced risk of inappropriate transcriptional behavior due to a reduced number of undesirable transcription regulatory sequences.

An isolated and optimized nucleic acid molecule may have a codon composition that differs from that of the corresponding wild type nucleic acid sequence at more than 30%, 35%, 40% or more than 45%, e.g., 50%, 55%, 60% or more of the codons. Exemplary codons for use in the invention are those which are employed more frequently than at least one other codon for the same amino acid in a particular organism and, in one embodiment, are also not low-usage codons in that organism and are not low-usage codons in the organism used to clone or screen for the expression of the nucleic acid molecule. Moreover, codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild type or parent nucleic acid sequence in those cells.

In one embodiment of the invention, the codons that are different are those employed more frequently in a mammal, while in another embodiment the codons that are different are those employed more frequently in a plant. Preferred codons for different organisms are known to the art, e.g., see www.kazusa.or.jp./codon/. A particular type of mammal, e.g., a human, may have a different set of preferred codons than another type of mammal. Likewise, a particular type of plant may have a different set of preferred codons than another type of plant. In one embodiment of the invention, the majority of the codons that differ are ones that are preferred codons in a desired host cell. Preferred codons for organisms including mammals (e.g., humans) and plants are known to the art (e.g., Wada et al., Nucl. Acids Res., 18:2367 (1990); Murray et al., Nucl. Acids Res., 17:477 (1989)).

IV. Exemplary Luciferase for Stability Enhancement

The luciferase secreted from the deep-sea shrimp *Oplophorus gracilirostris* has been shown to possess many interesting characteristics, such as high activity, high quantum yield, and broad substrate specificity (coelenterazine, coelenterazine analogs). The bioluminescent reaction of *Oplophorus* takes place when the oxidation of coelenterazine (the luciferin) with molecular oxygen is catalyzed by *Oplophorus* luciferase, resulting in light of maximum intensity at 462 nm and the products $CO_2$ and coelenteramide (Shimomura et al., Biochemistry, 17:994 (1978); this differs from Inouye 2000 which mentions 454 nm). Optimum luminescence occurs at pH 9 in the presence of 0.05-0.1 M NaCl at 40° C., and, due to the unusual resistance of this enzyme to heat, visible luminescence occurs at temperatures above 50° C. when the highly purified enzyme is used, or at over 70° C. when partially purified enzyme is used. At pH 8.7, the native luciferase has a molecular weight of approximately 130,000, apparently comprising 4 monomers of 31,000; at lower pHs, the native luciferase tends to polymerize.

The mature protein consists of 19 kDa and 35 kDa proteins (heterotetramer consisting of two 19 kDa components and two 35 kDa components). The 19 kDa protein (OgLuc) has been overexpressed as a monomer in *E. coli* and shown to be active, however, it is produced predominantly as inclusion bodies. The formation of inclusion bodies is likely due to the instability of the protein inside of the cell.

A 3D structure of OgLuc is not available. In addition, there are no known homology-based models available, as OgLuc does not have any sequence homology to other luciferases and no significant overall sequence similarity to other known proteins. In order to generate a model, a fold recognition method designed to identify distant homologous proteins was used. Using this approach, as described hereinbelow, a set of fatty acid binding proteins (FABPs) belonging to the calycin protein superfamily was identified, and an OgLuc homology model was generated based on the 3D structures of three of these FABPs.

Calycins are a protein superfamily whose members share similar n-barrel structures. Members include, but are not limited to, fatty acid binding proteins (FABPs) and lipocalins. The FABP protein family has a ten-stranded discontinuous n-barrel structure; the avidin and MPI barrels, although eight-stranded, are more circular in cross-section than that of the lipocalins and do not have a C-terminal helix or strand I; while triabin has a similar barrel geometry yet has a modified topology. The N- and C-terminal strands of the FABPs and lipocalins can be closely superimposed, with the loss (FABP to lipocalin) or gain (lipocalin to FABP) of two central strands necessary to effect the transformation of one to another (Flower et al., Protein Science, 2:753 (1993)). Moreover, beyond some functional similarity (hydrophobic ligand binding and/or macromolecular interaction) these families are characterized by a similar folding pattern (an antiparallel β-barrel dominated by a largely +1 topology), within which large parts of their structures can be structurally equivalenced, although the families share no global sequence similarity.

Previous work (Flower, Protein Pept. Lett., 2:341 (1995)) has shown that members of the calycin superfamily also share a distinct structural pattern. An arginine or lysine residue (from the last strand of the β-barrel) which forms hydrogen bonds to the main-chain carbonyl groups of the N-terminal $3_{10}$-like helix and packs across a conserved tryptophan (from the first strand of the n-barrel). This pattern can be seen both in the structures of kernel lipocalins, which also share a conserved interaction from loop L6, and in the more structurally diverse outlier lipocalins. It is also apparent in the other four families comprising the calycins. Examination of the available structures of streptavidin and chicken avidin, the metalloproteinase inhibitor from *Erwinia chrysanthemi*, and the structure of triabin, all reveal a very similar arrangement of interacting residues. Most of the known FABPs have an arrangement of side chain interactions similar to those described above, in which a tryptophan, from the first strand of the FABP barrel, packs against an arginine from near the end of the last. This feature is, however, lacking from a group of more highly diverged FABPs, typified by insect muscle FABPs.

The OgLuc homology model shows that the calycin fold structural signature, which effectively ties the N- and C-terminus together with hydrogen bonds, and which is present in the three FABPs, is not completely conserved in OgLuc. The distinct structural signature (in which an arginine or lysine, able to form a number of potential hydrogen bonds with the main chain carbonyls of a short $3_{10}$ helix, packs across a conserved tryptophan in a structurally superimposable, non-random manner) corresponds to sequence determinants common to the calycin member families: a characteristic N-terminal sequence pattern, displaying preservation of key residues, and a weaker C-terminal motif. The preservation of particular residues and interactions, across the member families lends some support to the view that there was a common, if very distant, evolutionary origin for the calycin superfamily. The present OgLuc model predicts that OgLuc residue Asn166 near the C-terminus is unable to hydrogen bond with main-chain carbonyls near the N-terminus. However, models of mutants containing either Arg or Lys at position 166 suggest restoration of this structure motif could improve the structural stability of the OgLuc and its expression/activity in cells.

The invention will be further described by the following non-limiting examples.

Example 1

The shortcomings of OgLuc could be addressed by protein engineering, but to do so in an efficient manner would require knowledge about the three-dimensional (3D) structure of OgLuc. There is no published experimental tertiary structure or tertiary structure model of OgLuc. Homology modeling was used to generate a tertiary structure model of OgLuc. Building a homology model comprises several steps including identification of 3D structural template(s), alignment of target sequence (e.g., OgLuc) and template structure(s), model building, and model quality evaluation. Identification of one or more 3D structural templates for OgLuc was not intuitive because standard sequence search methods did not identify significant overall similarity to proteins with known tertiary structure. To overcome this problem, two approaches were employed to identify remote OgLuc homologs with known tertiary structure.

Approach 1:

An Hidden Markov Model (HMM) based template library search (Karplus et al., Bioinformatics, 14:846 (1998)) was used to detect distantly related template structures using the SWISS-MODEL Template identification Tool at swissmodel.expasy.org//SWiSS-MODEL.html (Arnold et al. Bioinformatics, 22:195 (2006)).

The best (highest E-value score) 3D structure template identified for OgLuc using this approach was a fatty acid binding protein (FABP) (Protein Data Bank (PDB) accession number 1VYF) (Angelucci et al., Biochemistry, 43:13000 (2004)). Additional FABPs with lower scores were also identified, including PDB accession numbers 1PMP and 1CRB.

Exemplary alignments of the target sequence (OgLuc, residues 1-2 and 168-169 omitted) and the sequences of the identified 3D structure templates (1VYF, 1PMP, 1CRB) are shown below. Note that due to the low sequence similarity, the placement of gaps in the alignment can vary.

```
1vyf     1 GSMSSFLGKWKLSESHNFDAVMSKLGVSWATRQIGNTVTPTVTFTMDGDK..   50
           F G W     N D V    G S     G   VTP        G
Target   3 --LADFVGDWQQTAGYNQDQVLEQGGLSSLFQALGVSVTPIQKVVLSGENgl   52

1vyf    51 .......MTMLTESTFKN..LSCTFKF....................GEEF   72
                  S F          FK                          G
Target  53 kadihviIPYEGLSGFQMglIEMIFKVvypvddhhfkiilhygtlvidGVTP  104

1vyf    73 DEKTSDGRNVKSVVEKNSESKLTQTQVDPKNTTVIVREV.DGDTMKTTVTVG
                    GR                   N     R         VT      123
Target 105 NMIDYFGRPYPGIAVFDGKQITVTGTLWNGNKIYDERLInPDGSLLFRVTIN  156

1vyf   124 DVTAIRNYKRLS                                         135  (SEQ ID NO: 5)
              VT  R
Target 157 GVTGWRLCENI                                          167  (SEQ ID NO: 7)

1pmp     3 SNKFLGTWKLVSSENFDEYMKALGVGLATRKLGNLAKPRVIISKKGDI....   48
           F G W     N D     G    LG  P         G
Target   3 LADFVGDWQQTAGYNQDQVLEQGGLSSLFQALGVSVTPIQKVVLSGENglka   54
```

```
                                        -continued
1pmp      49 ....................ITIRTESPFKNTEISFKL........GQEFEE    72
                                    P              L           G
Target    55 dihviipyeglsgfqmglieMIFKVVYPVDDHHFKIILhygtlvidGVTPNM   106

1pmp      73 TTADNRKTKSTVTLARGSLNQVQK.WNGNETTIKRKL.VDGKMVVECKMKDV   122
                R                    WNGN      R   DG           V
Target   107 IDYFGRPYPGIAVFDGKQITVTGTlWNGNKIYDERLInPDGSLLFRVTINGV   158

1pmp     123 VCTRIYEKV                                              131 (SEQ ID NO: 3)
                R E
Target   159 TGWRLCENI                                              167 (SEQ ID NO: 7)

1crb       1 PVDFNGYWKMLSNENFEEYLRALDVNVALRKIANLLKPDKEIVQDGDH....    48
                 DF G W     N   L                     P   V G
Target     3 LADFVGDWQQTAGYNQDQVLEQGGLSSLFQALGVSVTPIQKVVLSGENglka    54

1crb      49 ....................MIIRTLSTFRNYIMDFQV........GKEFEE    72
                                    MI                          G
Target    55 dihvilpyeglsgfqmglieMIFKVVYPVDDHHFKIILhygtlvidGVTPNM   106

1crb      73 DLTGIDDRKCMTTVSWDGDKLQCVQK.GEKEGRGWTQWI.EGDELHLEMRAE   122
                R              DG                  I  L
Target   107 --IDYFGRPYPGIAVFDGKQITVTGTlWNGNKIYDERLInPDGSLLFRVTIN   156

1crb     123 GVTCKQVFKKVH                                           134 (SEQ ID NO: 4)
             GVT
Target   157 GVTGWRLCENI-                                           165 (SEQ ID NO: 7)
```

Approach 2:

A fold recognition method using the "GeneSilico meta-server" at genesilico.pl/meta2 (Kurowski et al., Nucl. Adds Res., 31:3305 (2003)) was also used to identify remote OgLuc homologs with known tertiary structure.

A protein fold is a 3D structural classification. Proteins that share the same fold have a similar arrangement of regular secondary structures but without necessarily showing evidence of evolutionary relatedness on the protein sequence level.

Using this method, three highest scoring 3D structure templates were identified (PDB accession numbers 1VYF, 1PMP, and 1CRB). Exemplary alignments of the target sequence (OgLuc) and the sequences of the 3D structure templates (1VYF, 1PMP, 1CRB) are shown below. Note that due to the low sequence similarity, the exact placement of gaps in the alignment is difficult to predict with confidence.

OgLuc and 1PMP:

```
--SNKFLGTWKLVSSENFDEYMKALGVGLATRKLGNLAKPRVIISKKG------DIITIRTE------------------
FTLADFVGDWQQTAGYNQDQVLEQGGLSSLFQALGVSVTPIQKVVLSGENGLKADIHVIIPYEGLSGFQMGLIEMIFKVV

-----SPFKNTEISFKLGQEFEETTAD-----NRKTKSTVTLARGSLNQV-QKWNGNETTIKRKLV-DGKMVVECKMKDV
YPVDDHHFKIILHYGTL--VIDGVTPNMIDYFGRPYPGIAVFDGKQITVTGTLWNGNKIYDERLINPDGSLLFRVTINGV

VCTRIYEKV-- (1PMP)  (SEQ ID NO: 3)
TGWRLCENILA (OgLuc) (SEQ ID NO: 1)
```

OgLuc and FABPs:

```
--SNKFLGTWKLVSSENFDEYMKALGVGLATRKLGNLAKPRVIISKKG------DIITIRTESP----------------
--PVDFNGYWKMLSNENFEEYLRALDVNVALRKIANLLKPDKEIVQDG------DHMIIRTLST----------------
GSMSSFLGKWKLSESHNFDAVMSKLGVSWATRQIGNTVTPTVTFTMDG------DKMTMLTEST----------------
FTLADFVGDWQQTAGYNQDQVLEQGGLSSLFQALGVSVTPIQKVVLSGENGLKADIHVIIPYEGLSGFQMGLIEMIFKVV

-------FKNTEISFKLGQEFEETTA-----DNRKTKSTVTLAR-GSLNQV-QKWNGNETTIKRKLV-DGKMVVECKMKD
-------FRNYIMDFQVGKEFEEDLT---GIDDRKCMTTVSWDG-DKLQCV-QKGEKEGRGWTQWIE-GDELHLEMRAEG
-------FKNLSCTFKFGEEFDEKTS-----DGRNVKSVVEKNSESKLTQT-QVDPKNTTVIVREVD-GDTMKTTVTVGD
YPVDDHHFKIILHYGTL--VIDGVTPNMIDYFGRPYPGIAVFDG-KQITVTGTLWNGNKIYDERLINPDGSLLFRVTING

VVCTRIYEKV-- (1PMP)  (SEQ ID NO: 3)
VTCKQVFKKVH- (1CRB)  (SEQ ID NO: 4)
VTAIRNYKRLS- (1VYF)  (SEQ ID NO: 5)
VTGWRLCENILA (OgLuc) (SEQ ID NO: 1)
```

Using the information generated in the above approaches, OgLuc homology models were generated based on three FABP 3D structure templates (1PMP, 1CRB, and 1VYF) using Discovery Studio and MODELER software (Accelrys Software Inc.).

FIG. 1 also shows the secondary structure alignments of FABPs and OgLuc. 1PMP, 1CRB, 1VYF are the Protein Data Bank (www.rcsb.org) accession codes for exemplary FABP sequences with known 3D structure. "PDB" means secondary structure assignment provided by authors who deposited the 3D structure information into Protein Data Bank. "DSC" means secondary structure prediction based on DSC method (King et al., Protein Science, 5:2298 (1996)). "Kabasch and Sander" means secondary structure prediction based on Kabasch and Sander method (Kabasch and Sander, Biopolymers, 22:2577 (198)). Red boxes indicate approximate extend of helix secondary structure elements, blue arrows indicate approximate extend of beta-sheet secondary structure elements, and gray bars indicate secondary structure other than helix or beta-sheet. The sequence motifs centered on the conserved residues of the calycin structural signature (Flower et al., Biochem. Biophys. Acta., 16:1088(2000)) may be seen in the alignments. The more highly conserved N-terminal MOTIF1 includes OgLuc residue Trp10, and the less well conserved C-terminal MOTIF2 includes OgLuc residue N166. For the second alignment, the approximate pair-wise percent protein sequence identities are: OgLuc-1PMP 14%, OgLuc-1CRB 9%, and OgLuc-1VYF 15%.

Figure 2:
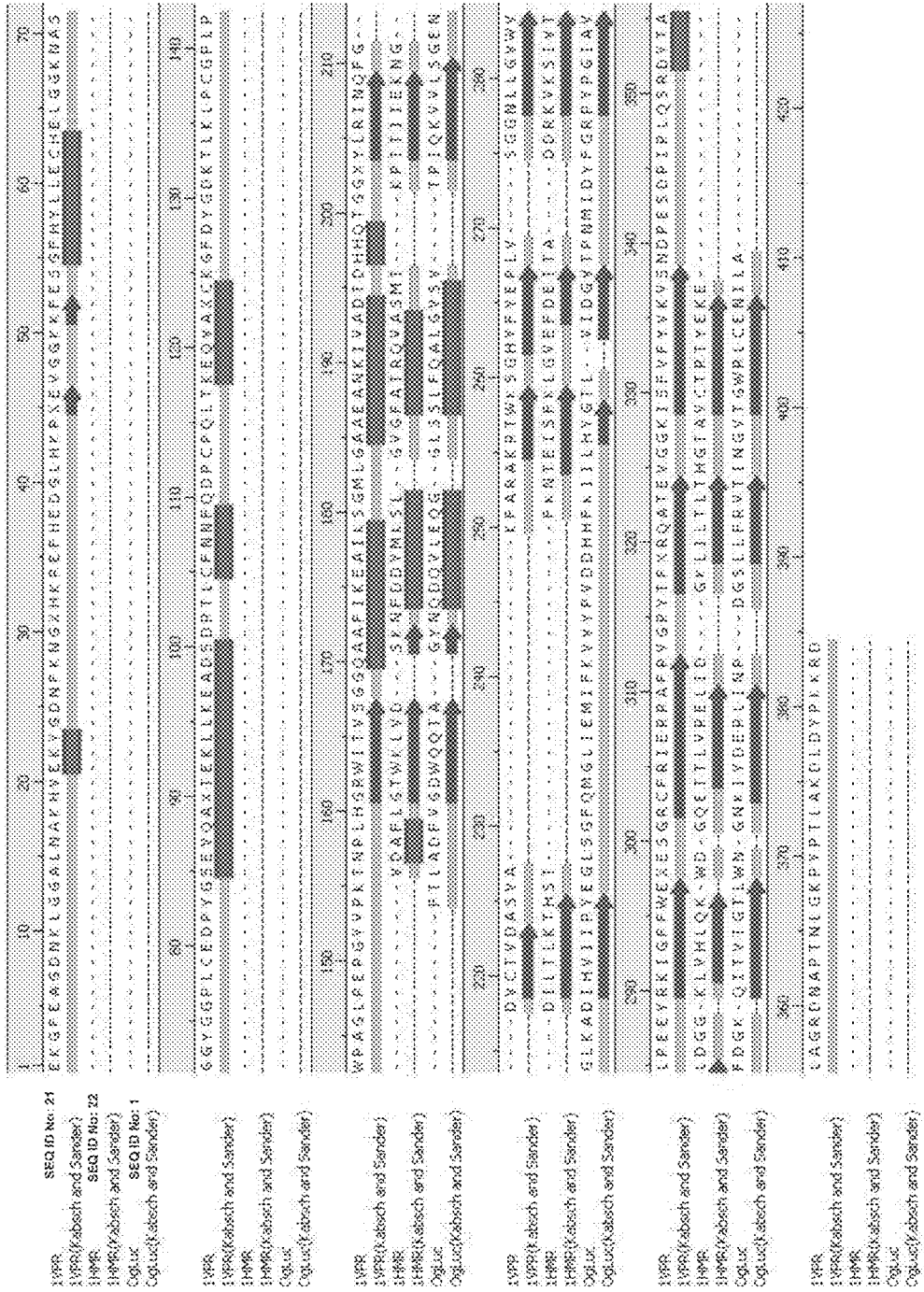
FIG. 2 shows secondary structure alignments of dinoflagellate luciferase, FABP and OgLuc.

FIG. 2 shows the secondary structure alignments of dinoflagellate luciferase, FABP and OgLuc. 1VPR and 1HMR are the Protein Data Bank (www.rcsb.org) accession codes for sequences with known 3D structure. 1VPR is dinoflagellate luciferase domain 3 and 1HMR is human muscle FABP, the most closely related protein to dinoflagellate luciferase (Schultz et al., PNAS USA, 102:1378 (2005)). "Kabasch and Sander" means secondary structure prediction based on Kabasch and Sander method (Kabasch and Sander, Biopolymers, 22:2577(1983)). Red boxes indicate approximate extend of helix secondary structure elements, blue arrows indicate approximate extend of beta-sheet secondary structure elements, and gray bars indicate secondary structure other than helix or beta-sheet. 1VPR has SEQ ID NO:21; 1HMR has SEQ ID NO:22.

Figure 3:
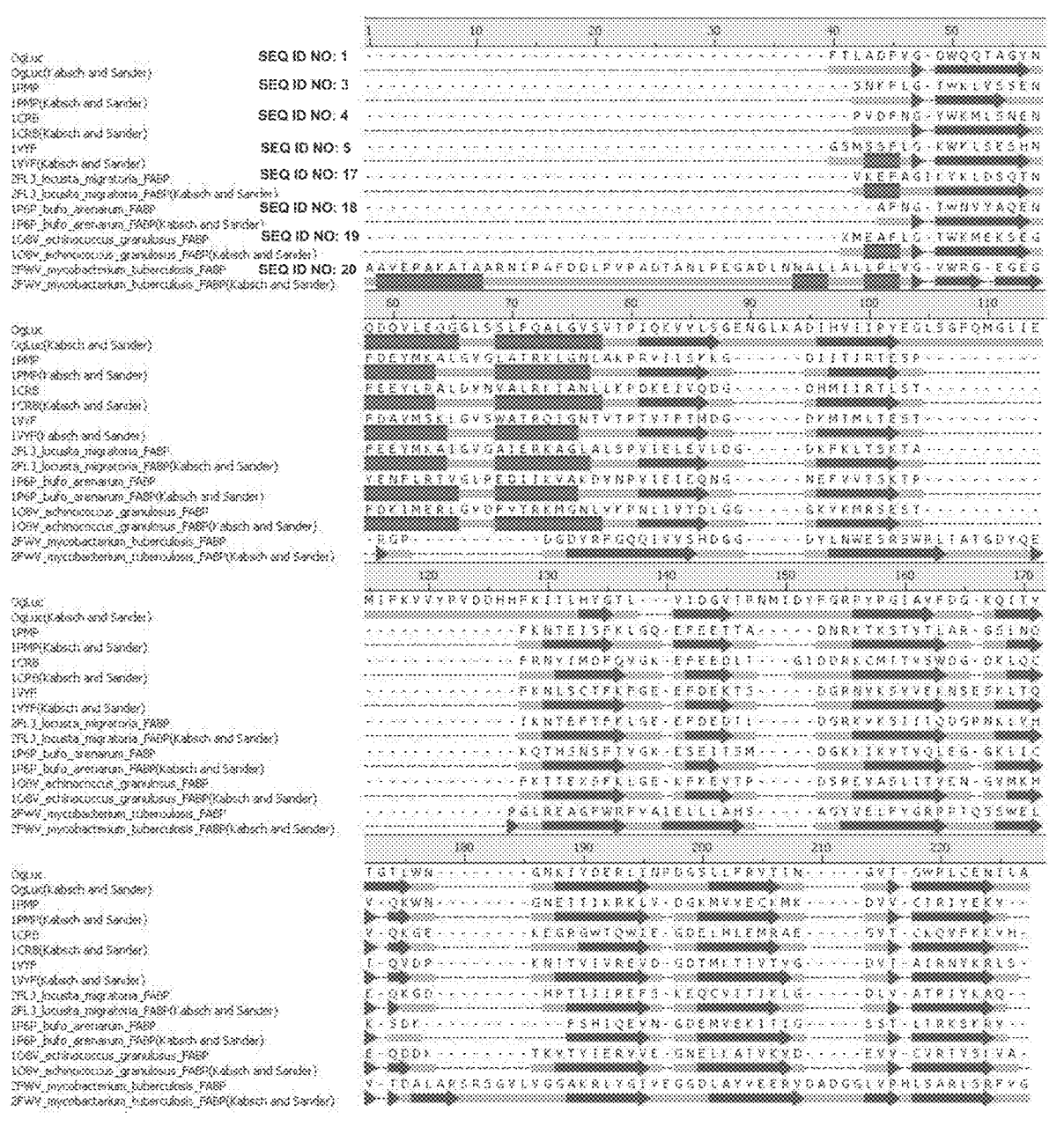

FIG. 3 shows the alignment of the amino acid sequences of OgLuc and various FABPs (SEQ ID NOs: 1, 3, 4, 5, and 17-20, respectively) based on the 3D structure superimposition of FABPs.

Example 2

Fatty acid binding proteins (FABPs) belong to the calycin protein superfamily. Calycins have no significant overall similarity at the sequence level, but share a related beta-barrel structure with a distinct structural signature: an arginine or lysine (near the C-terminus) that is able to form a number of potential hydrogen bonds with the main chain carbonyls of a short $3_{10}$ helix and packs across a conserved tryptophan (near the N-terminus) (Flower et al., Biochem. Biophys. Acta, 1482:9 (2000)). In the OgLuc model generated in Example 1, the calycin structural signature is only partially present. The conserved tryptophan (Trp10) near the N-terminus (such as one in a N-terminal beta-sheet of a beta-barrel) packs across an asparagine (Asn166) instead of an arginine or lysine near the C-terminus (such as one in a C-terminal beta-sheet of a beta-barrel). The present model predicts that the shorter asparagine side chain seems unable to form hydrogen bonds with residues near the N-terminus (in the N-terminal beta-sheet of the beta-barrel). OgLuc models, where the substitutions Asn166Arg and Asn166Lys were made, demonstrated that the longer arginine and lysine side chains in OgLuc should be able to form one or more bonds, e.g., one or more hydrogen bonds, with main chain carbonyls and/or side chains of residues near the N-terminus. For example, they may form one or more hydrogen bonds with OgLuc residues Asp9 and/or Gly8 and/or Asp5 near the N-terminus. Additionally, they could form one or more hydrogen bonds to one or more residues in other secondary structure elements that are in close spacial proximity to position 166, e.g., Asn144 and/or Gly147. Thus, restoring the calycin structural signature in OgLuc with an Asn166Arg or Asn166Lys mutation may effectively tie together the two termini of the beta-barrel (or terminal beta-sheets of the beta-barrel) and possibly other secondary structure elements. This could improve overall stability of the protein structure, and thus OgLuc activity.

An exemplary OgLuc protein sequence is

FTLADFVGDW QQTAGYNQDQ VLEQGGLSSL FQALGVSVTP

IQKVVLSGEN GLKADIHVII PYEGLSGFQM GLIEMIFKVV

YPVDDHHFKI ILHYGTLVID GVTPNMIDYF GRPYPGIAVF

DGKQITVTGT LWNGNKIYDE RLINPDGSLL FRVTINGVTG

WRLCENILA (SEQ ID NO: 1; 169 amino acids, Asn166 bold underlined).

An exemplary OgLuc nucleotide sequence is (SEQ ID NO: 2)
atggtgtttaccttggcagatttcgttggagactggcaacagacagctgg atacaaccaagatcaagtgttagaacaaggaggattgtctagtctgttcc aagccctgggagtgtcagtcaccccaatccagaaagttgtgctgtctggg gagaatgggttaaaagctgatattcatgtcatcatcccttacgagggact cagtggttttcaaatgggtctgattgaaatgatcttcaaagttgtttacc cagtggatgatcatcatttcaagattattctccattatggtacactcgtt attgacggtgtgacaccaaacatgattgactactttggacgcccttaccc tggaattgctgtgtttgacggcaagcagatcacagttactggaactctgt ggaacggcaacaagatctatgatgagcgcctgatcaacccagatggttca ctcctcttccgcgttactatcaatggagtcaccggatggcgcctttgcga gAACattcttgcc.

The AAC codon of SEQ ID NO:2, which is capitalized in the listing above, corresponds to amino acid position 166 in the mature wild-type OgLuc sequence of SEQ ID NO:1. The nucleotide sequence of SEQ ID NO:2 also includes an ATG codon (methionine/start signal) and a GTG codon (valine) at the beginning for convenience of use in expression systems. Nevertheless, the amino acid numbering used throughout this application to identify substituted residues is given relative to the mature wild-type OgLuc polypeptide sequence of SEQ ID NO:1. The naturally-occurring wild-type OgLuc sequence may be initially synthesized with other amino acids which are later cleaved, resulting in the generation of a mature wild-type polypeptide such as shown in SEQ ID NO:1. For example, a signal sequence (e.g. to direct the nascent protein to a particular organelle such as the endoplasmic reticulum and/or to direct the protein for secretion) may be present at the beginning of the nascent protein and may then be cleaved to produce the mature wild-type protein.

An exemplary alignment of OgLuc and three FABPs is shown below.

taining 20 μM coelenterazine (Promega Corp.) ("RLAB") to the lysate sample. This luminescence measurement, taken immediately after addition, is the "T=0" time point measurement and in various embodiments is taken as a measure of the total light output (luminescence) generated by the sample. The average luminescence of the 6 replicates was

```
--SNKFLGTWKLVSSENFDEyMKALGVGLATRKLGNLAKPRVIISKKG------DIITIRTESP----------
--PVDFNGYWKMLSNENFEEYLRALDVNVALRKIANLLKPDKEIVQDG------DHMIIRTLST----------
GSMSSFLGKWKLSESHNFDAVMSKLGVSWATRQIGNTVTPTVTFTMDG------DKMTMLTEST----------
FTLADFVGDWQQTAGYNQDQVLEQGGLSSLFQALGVSVTPIQKVVLSGENGLKADIHVIIPYEGLSGFQMGLIE
            11                33      44      54

--------------FKNTEISFKLGQEFEETTA-----DNRKTKSTVTLAR-GSLNQV-QKWNGNETTIKRKLV-
--------------FRNYIMDFQVGKEFEEDLT---GIDDRKCMTTVSWDG-DKLQCV-QKGEKEGRGWTQWIE-
--------------FKNLSCTFKFGEEFDEKTS-----DGRNVKSVVEKNSESKLTQT-QVDPKNTTVIVREVD-
MIFKVVYPVDDHHFKIILHYGTL--VIDGVTPNMIDYFGRPYPGIAVFDG-KQITVTGTLWNGNKIYDERLINP
75                        114     115     124     135

DGKMVVECKMKDVVCTRIYEKV-- (SEQ ID NO: 3)
GDELHLEMRAEGVTCKQVFKKVH- (SEQ ID NO: 4)
GDTMKTTVTVGDVTAIRNYKRLS- (SEQ ID NO: 5)
KGSLLFRVTINGVTGWRLCENILA (SEQ ID NO: 1)
```

Example 3

Generation of Modified Luciferase Variants with Increased Luminescence

Unless otherwise stated, variants of a starting OgLuc sequence with random substitutions were generated using the error-prone, mutagenic PCR-based system GeneMorph II Random Mutagenesis Kit (Stratagene; Daughtery, PNAS USA 97(5):2029 (2000)), according to manufacturer's instructions, and NNK saturation as known in the arts. The resulting variants were constructed in the context of pF1K Flexi® vector for T7 based expression (Promega Corp.) and were used to transform KRX E. coli using techniques known in the art. The resulting library was expressed in E. coli and screened for variants that had increased light emission compared to the starting OgLuc protein. Standard sequencing techniques known in the art were used to identify the amino acid substitution in each clone of interest.

Variants of a starting OgLuc sequence with specific mutations were generated using the oligo-based site-directed mutagenesis kit QuikChange Site-Directed Mutagenesis Kit (Stratagene; Kunkel, PNAS USA 82(2):488 (1985)), according to the manufacturer's instructions.

Example 4

Methods to Measure Light Emission and Signal Stability

E. coli clones containing the plasmid DNA encoding modified luciferase variants with amino acid substitutions in OgLuc were grown in a 96-well plate and induced with walk away induction, i.e. autoinduction (Shagat et al., "KRX Autoinduction Protocol: A Convenient Method for Protein Expression," Promega Notes 98:17 (2008)) for 17 hours. Each variant and corresponding starting luciferase had 6 well replicates. Cells were lysed using a lysis buffer consisting of 150 mM HEPES pH 8.0, 100 mM thiourea, 0.1×PLB (Promega Corp. Cat. No. E194A), 0.1 mg/mL lysozyme and 0.001 U/μL RQ1 DNase, and measured for luminescence using Renilla luciferase substrate reagents (Promega Corp.) on an Infinite 500 Tecan luminometer. Measurements were taken immediately after addition with injection of either a "Glo" 0.5% tergitol assay buffer ("0.5% tergitol"), which contains 150 mM KCl, 1 mM CDTA, 10 mM DTT, 0.5% tergitol, 20 μM coelenterazine (Promega Corp.)), or a "Flash" RLAB buffer (Promega Corp.) concompared between the variants with that of the corresponding starting luciferase. In various embodiments, the luminescence measurements were normalized to the corresponding starting luciferase of interest, for example synthetic OgLuc, and referred to in certain embodiments as "fold" (i.e. 2-fold, 3-fold, 4.5-fold, etc.) improvement, increase, or the like.

The signal stability of a variant clone was determined by re-reading the plate multiple times after the addition of the assay buffer to the sample, for example, measuring luminescence every 30 seconds or every 1 minute, for a length of time. The signal half-life was determined using these measurements and the average of the 6 replicates was compared between the variants with the corresponding starting luciferase. The half-life indicating signal stability was normalized to the corresponding starting luciferase of interest, for example OgLuc.

Example 5

Method of Measuring Protein Stability, i.e. Thermostability

Lysate samples were prepared from induced cultures as described in Example 4. Lysate samples in replicate 96 well plates were incubated at various temperatures, including for example at 22, 30, 37, 42, 50 or 54° C. At different time points, plates were placed at −70° C. Prior to measuring the luminescence as described in Example 4, each plate was thawed at RT, i.e. 22° C., for 10 minutes. Samples were assayed with the 0.5% tergitol assay buffer described in Example 4. The "T=0" measurement, as described in Example 4, for each time point plate, was used to determine the half-life of the protein. The half-life, which indicates protein stability, was normalized to the corresponding starting luciferase of interest, for example OgLuc.

Example 6

Generation of a Modified Luciferase with Increased Light Emission

To examine whether restoring the calycin structural signature in OgLuc could improve overall protein stability and activity, synthetic versions of the OgLuc sequence was designed. The synthetic versions included optimized codon usage for E. coli and mammalian cells and codons for either Arg or Lys substituted for Asn at position 166. As mentioned previously, the numbering is based on SEQ ID NO:1. Codon optimization (for *E. coli*) and nucleotide changes for codon 166 to Arg or Lys were engineered by synthetic means (Gene Dynamics, LLC). In the clone OgLuc+N166R, the AAC codon was changed to CGT (to code for Arg). In the clone OgLuc+N166K, the AAC codon was changed to AAA (to code for Lys).

The synthetic OgLuc genes were subcloned into a vector suitable for overexpression in bacteria or TnT® rabbit reticulocyte lysates (Promega Corp.; pF1K Flexi® vector for T7 based expression systems), and used to transform KRX *E. coli*. Individual colonies were picked, grown, induced with rhamnose, lysed using lysozyme and a single freeze-thaw, and measured for luminescence using *Renilla* luciferase substrate reagents (Promega Corp.) on a Veritas luminometer. Rabbit reticulocyte TnT® reactions were carried out according to the manufacturer's protocols (Promega Corp.) and measured the same way as the bacterial lysates.

The mutants were compared to the synthetic parental (i.e. starting) OgLuc protein for production of total light output (luminescence). In *E. coli*, a 5-fold and 10-fold improvement (N166K and N166R, respectfully) in luminescence was observed with coelenterazine as a substrate. In the TnT® lysates the improvement was between 4-fold and 7-fold (N166K and N166R). These sequences (containing either Arg or Lys at position 166) represent variants of OgLuc that result in enhanced stability.

Various OgLuc variants with an amino acid substitution at position 166 were analyzed for brightness, e.g., screened for variants that were at least 1.2× brighter than wild type OgLuc. The following substitutions yielded a variant that was at least 1.2× brighter than wild type OgLuc: N166K; N166R; N166A; N166L; N166P; N166Q; and N166S. (See Table 1). Table 1 shows the brightest variant, as indicated by the fold improvement over wild-type OgLuc, had the amino acid substitution N166R.

TABLE 1

Summary of the fold improvement in luminescence of the OgLuc variants with amino acid substitution at position 166 over wild type OgLuc.

| Amino Acid Substitution at Position 166 | Fold improvement |
|---|---|
| R | 10 |
| K | 4 |
| A | 3 |
| L | 3 |
| P | 2 |
| Q | 2 |
| S | 2 |

Mutagenesis using error-prone PCR and NNK saturation, as described in Example 3, of the OgLuc+N166R variant resulted in variants with enhanced brightness, e.g., at least 1.2× brighter, relative to the OgLuc+N166R variant. Table 2 summarizes these variants which comprised the N166R substitution as well as one of the following substitutions at residues 2 (S), 4 (E, S, R, G, D, T or L), 11 (R, V, I, L, K or T), 33 (K), 44 (I or L), 45 (E), 54 (F, T, V, G, W, S, or L), 68 (V, Y), 75 (R, K, Q, G, T or A), 104 (L), 115 (E, I, Q, L, V, G, H, R, S, C, A, or T), 124 (K), 135 (K), 138 (V, I, N, T, L, C, R, M or K), 139 (E), 167(V), or 169 (L). Table 2 shows the fold improvement in luminescence fold-improvement of the variant over the corresponding starting OgLuc+N166R variant using RLAB using an average of the signal in the range of 4-6 minutes after starting the reaction, e.g., after injection of the substrate. For each amino acid substitution listed, the most improved substitution is listed first and the least improved substitution listed last. The variants which showed the most improvement included variants containing a substitution at residue 4, 54, or 138.

TABLE 2

Summary of the fold improvement in luminescence of the OgLuc + N166R variants over the corresponding starting OgLuc + N166R.

| Position | Amino acid | Codon | Fold-improved brightness (RLAB), 4-6 min average (rel. to N166R) |
|---|---|---|---|
| 2 | S | TCC | 9 |
| 4 | E | GAG | 20 |
| 4 | S | AGT | 7 |
| 4 | R | AGG | 6 |
| 4 | G | GGG | 4 |
| 4 | D | GAT | 4 |
| 4 | T | ACG | 3 |
| 4 | L | CTG | 3 |
| 11 | R | CGG | 13 |
| 11 | V | GTG | 6 |
| 11 | I | ATT | 6 |
| 11 | L | CTT | 3 |
| 11 | K | AAG | 3 |
| 11 | T | ACT | 2 |
| 33 | K | AAG | 10 |
| 44 | I | ATT | 25 |
| 44 | L | CTT | 2 |
| 45 | E | GAG | 2 |
| 54 | F | TTT | 10 |
| 54 | T | ACT | 8 |
| 54 | V | GTT | 6 |
| 54 | G | GGG | 5 |
| 54 | S | AGT | 4 |
| 54 | W | TGG | 3 |
| 54 | L | TTG | 2 |
| 68 | V | GTT | 2 |
| 68 | Y | TAT | 3 |
| 72 | Q | CAG | 3 |
| 75 | R | AGG | 6 |
| 75 | K | AAG | 5 |
| 75 | Q | CAG | 5 |
| 75 | G | GGT | 4 |

TABLE 2-continued

Summary of the fold improvement in luminescence of the OgLuc + N166R variants over the corresponding starting OgLuc + N166R.

| Amino Position | acid | Codon | Fold-improved brightness (RLAB), 4-6 min average (rel. to N166R) |
|---|---|---|---|
| 75 | T | ACG | 4 |
| 75 | A | GCG | 4 |
| 104 | L | CTT | 10 |
| 115 | E | GAG | 20 |
| 115 | I | ATT | 4 |
| 115 | Q | CAG | 3 |
| 115 | L | CTT | 3 |
| 115 | V | GTT | 3 |
| 115 | G | GGG | 3 |
| 115 | H | CAT | 3 |
| 115 | R | CGG | 2 |
| 115 | S | AGT | 2 |
| 115 | C | TGT | 2 |
| 115 | A | GCT | 2 |
| 124 | K | AAA | 8 |
| 135 | K | AAG | 10 |
| 138 | V | GTG | 10 |
| 138 | I | ATT | 8 |
| 138 | T | ACG | 6 |
| 138 | L | CTG | 5 |
| 138 | C | TGT | 6 |
| 138 | R | CGG | 5 |
| 138 | M | ATG | 4 |
| 138 | K | AAG | 3 |
| 139 | E | GAG | 13 |
| 167 | V | GTT | 40 |
| 169 | L | TTG | 10 |

Additional variants of the OgLuc+N166R variant had more than one amino acid substitution. These additional variants are listed in Table 2 with the amino acid substitutions listed and the fold improvement in luminescence of the OgLuc+N166R variant over the corresponding starting N166R OgLuc. Additional variants were found which included silent mutations, i.e. changes in nucleotides which did not alter the amino acid encoded at that codon.

TABLE 3

Summary of the fold improvement in luminescence of the OgLuc + N166R variants with more than one amino acid substitution and/or silent mutations over the corresponding starting OgLuc + N166R.

| Fold over N166R | Amino Acid change from N166R (codons) |
|---|---|
| 6 | E23V (gta), S28P (cct), I143V (ctc) |
| 15 | A4S (gca), L34M (atg), I76V (gtc) |
| 2 | G51V (gtt), I99V (gtt) |
| 13 | L3L (tta), S37S (tcg), V44V (gta) |
| 5 | L3L (tta), L27M (atg) |
| 5 | L3L (tta) |
| 4 | L3L (tta), Q32L (cta), K43R (aga) |
| 3 | L72Q (cag), G10G (ggt) |
| 2 | N144K (aag), A54A (gca) |

Example 7

Evaluation of Specific Substitutions in Modified Luciferases

Figure 5B:
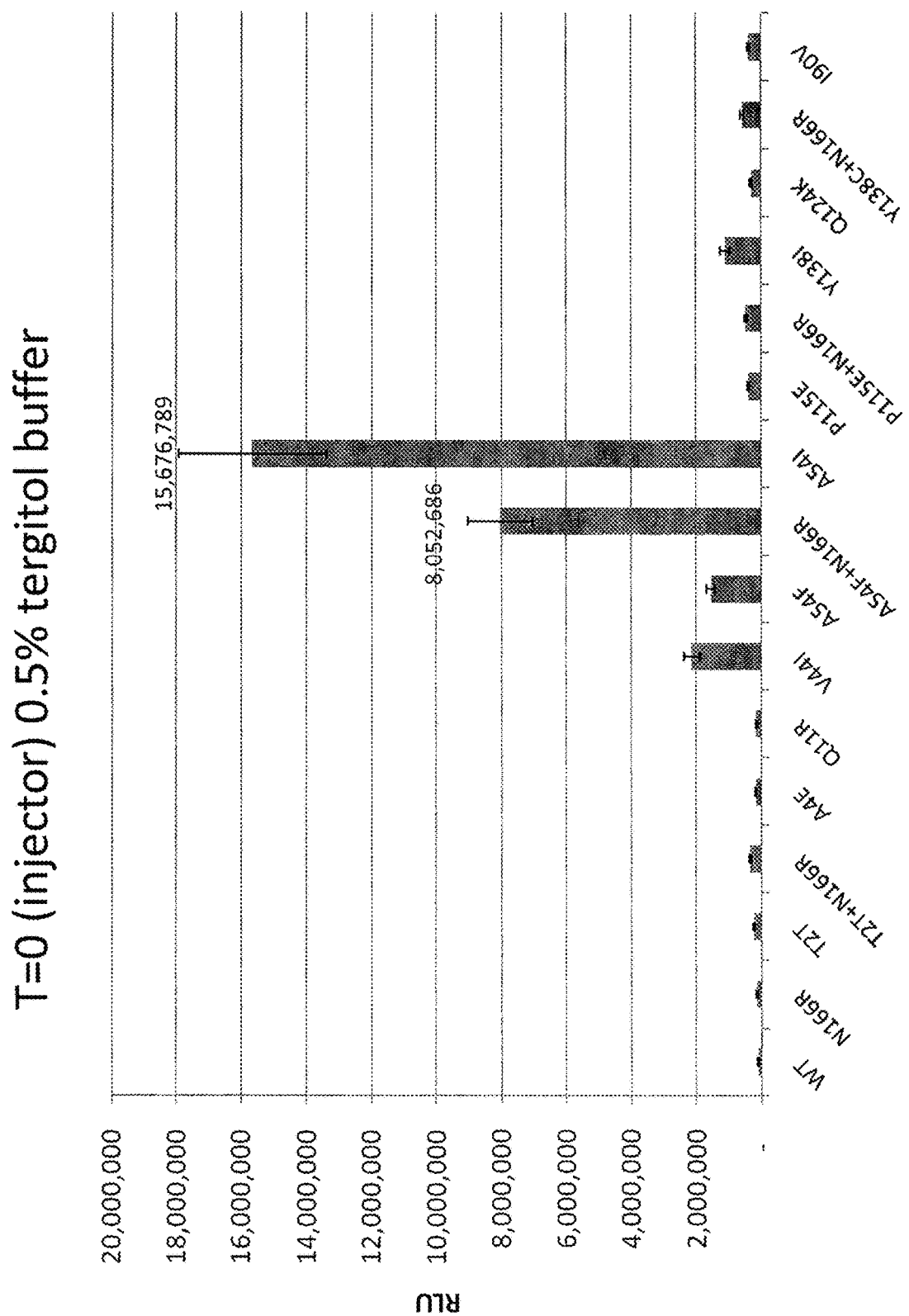
Figure 5C:
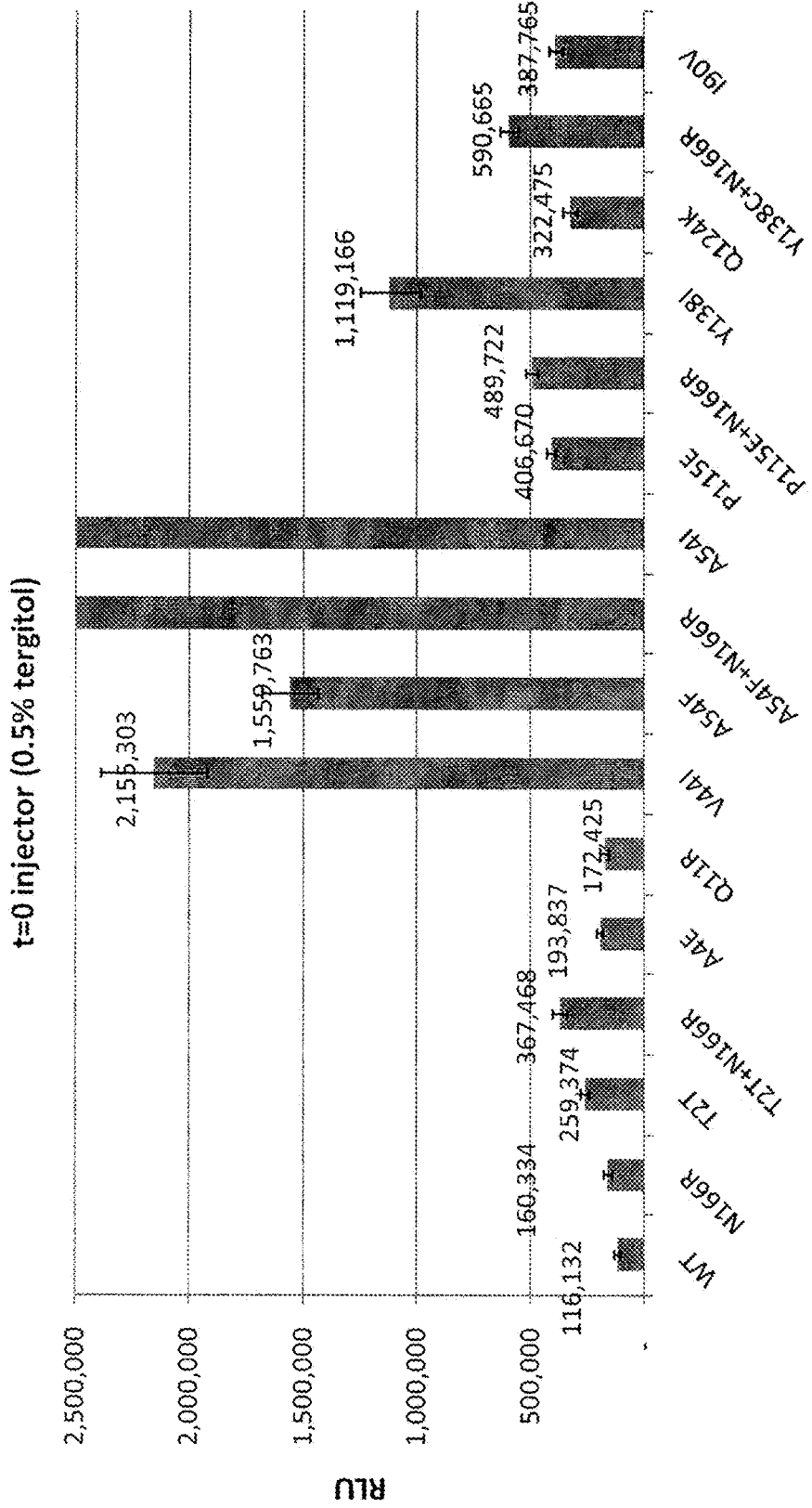
Figure 6A:
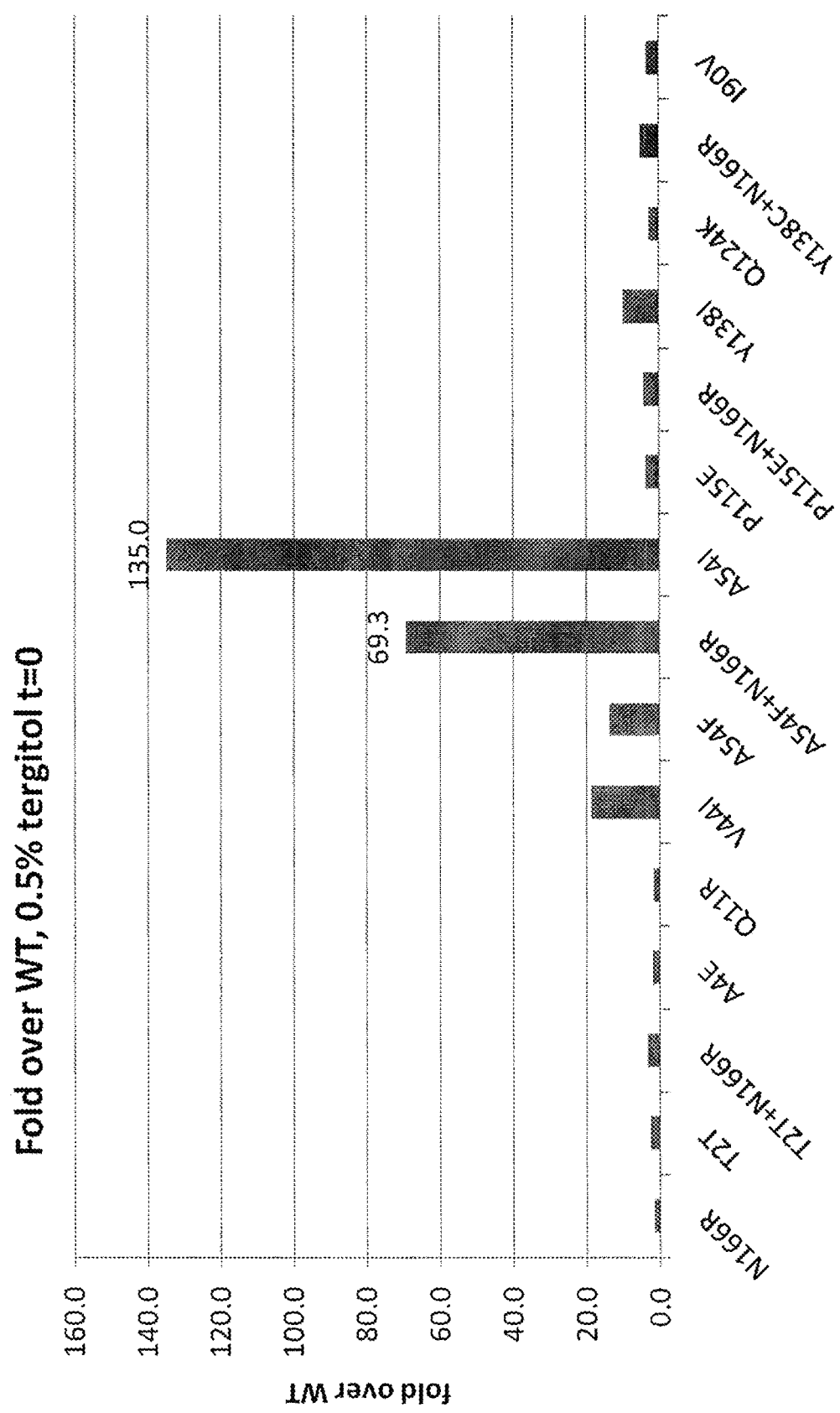
FIGS. 6A-B summarize the increase fold in luminescence at T=0 of the OgLuc variants over WT OgLuc determined from the 0.5% tergitol assay buffer data shown in FIGS. 5A-C.
Figure 6B:
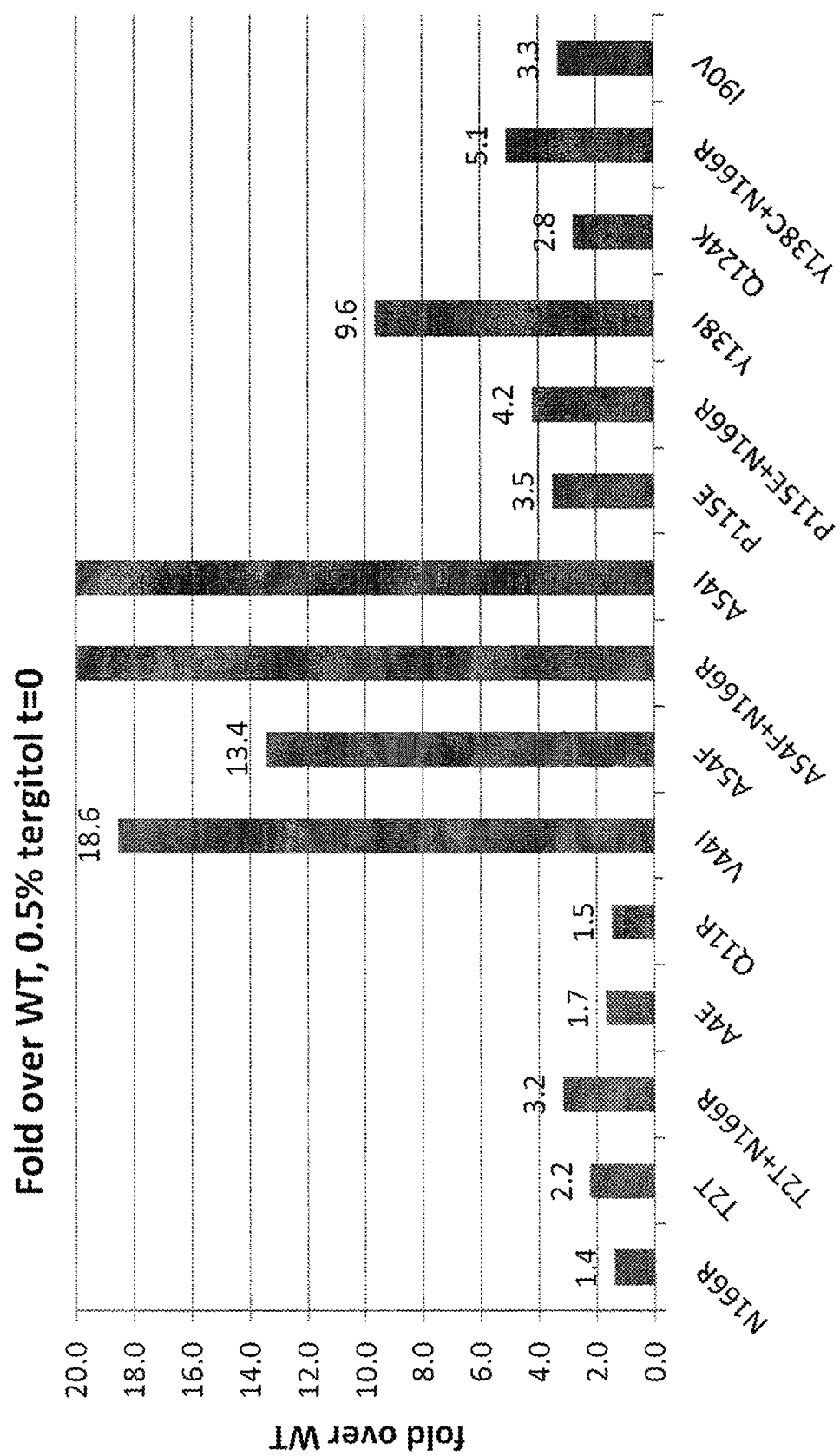
Figure 7B:
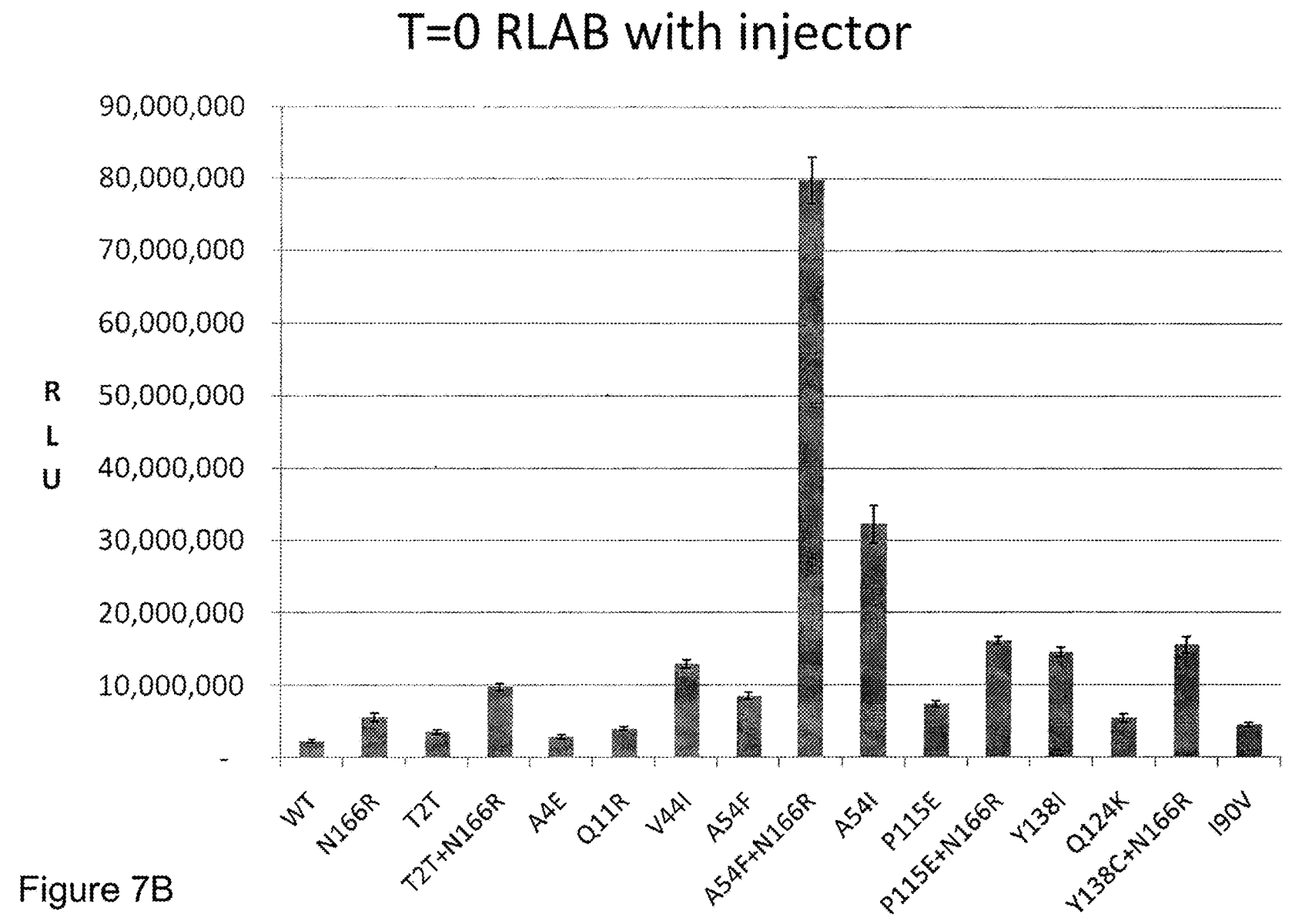
Figure 7C:
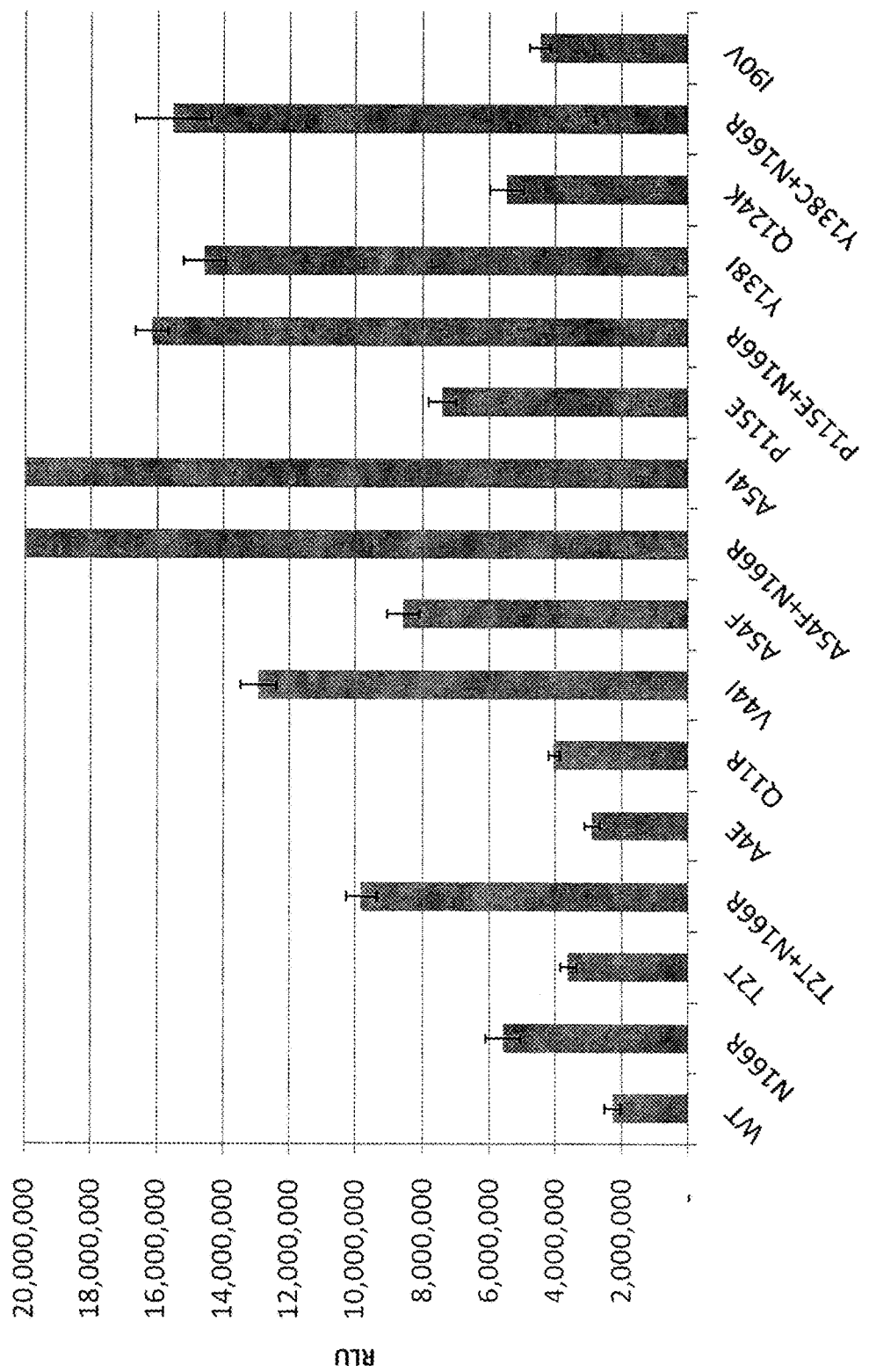
Figure 8:
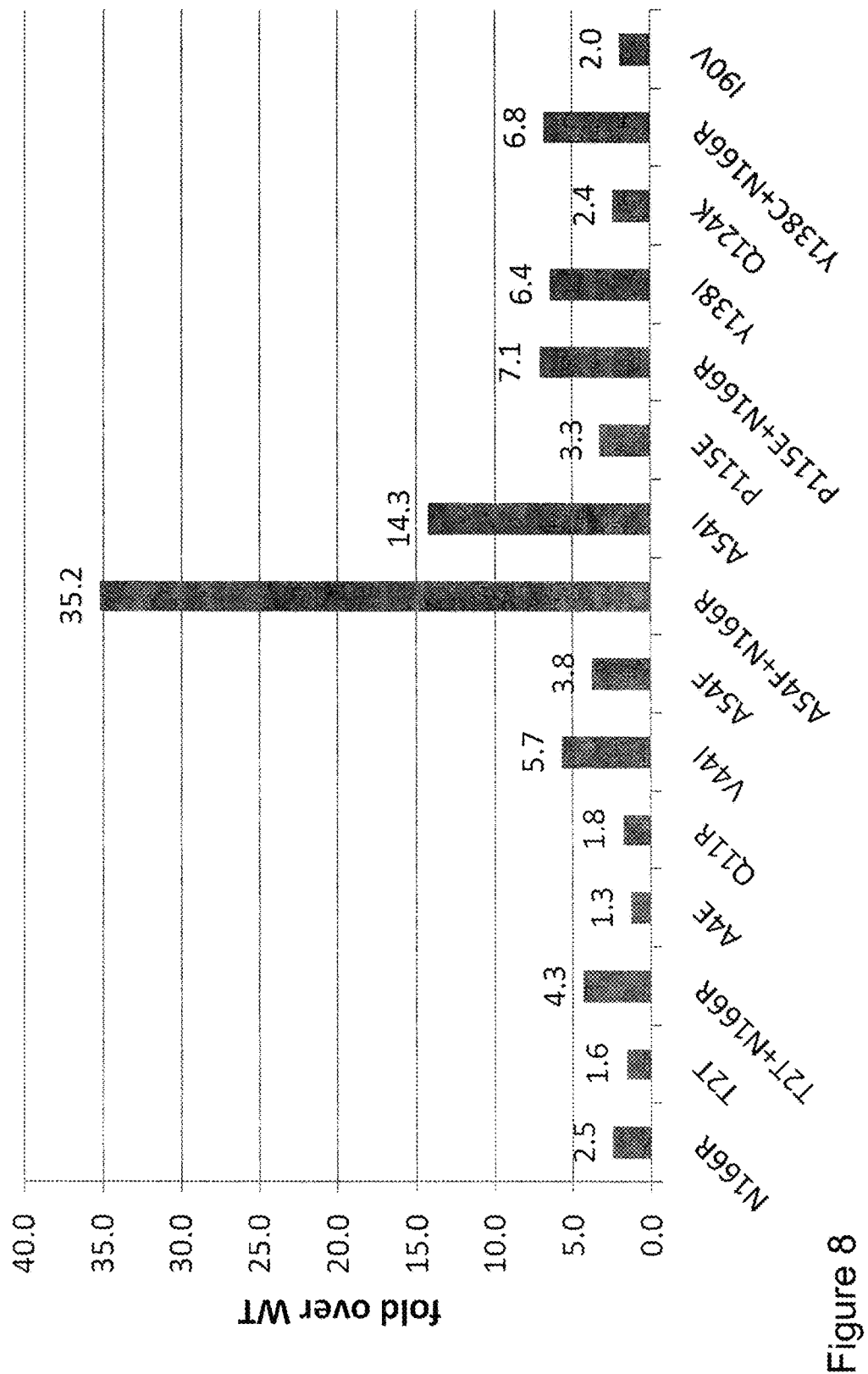
FIG. 8 summarizes the increase fold in luminescence at T=0 of the OgLuc variants over WT OgLuc determined from the RLAB data shown in FIGS. 7A-C.
Figure 9A:
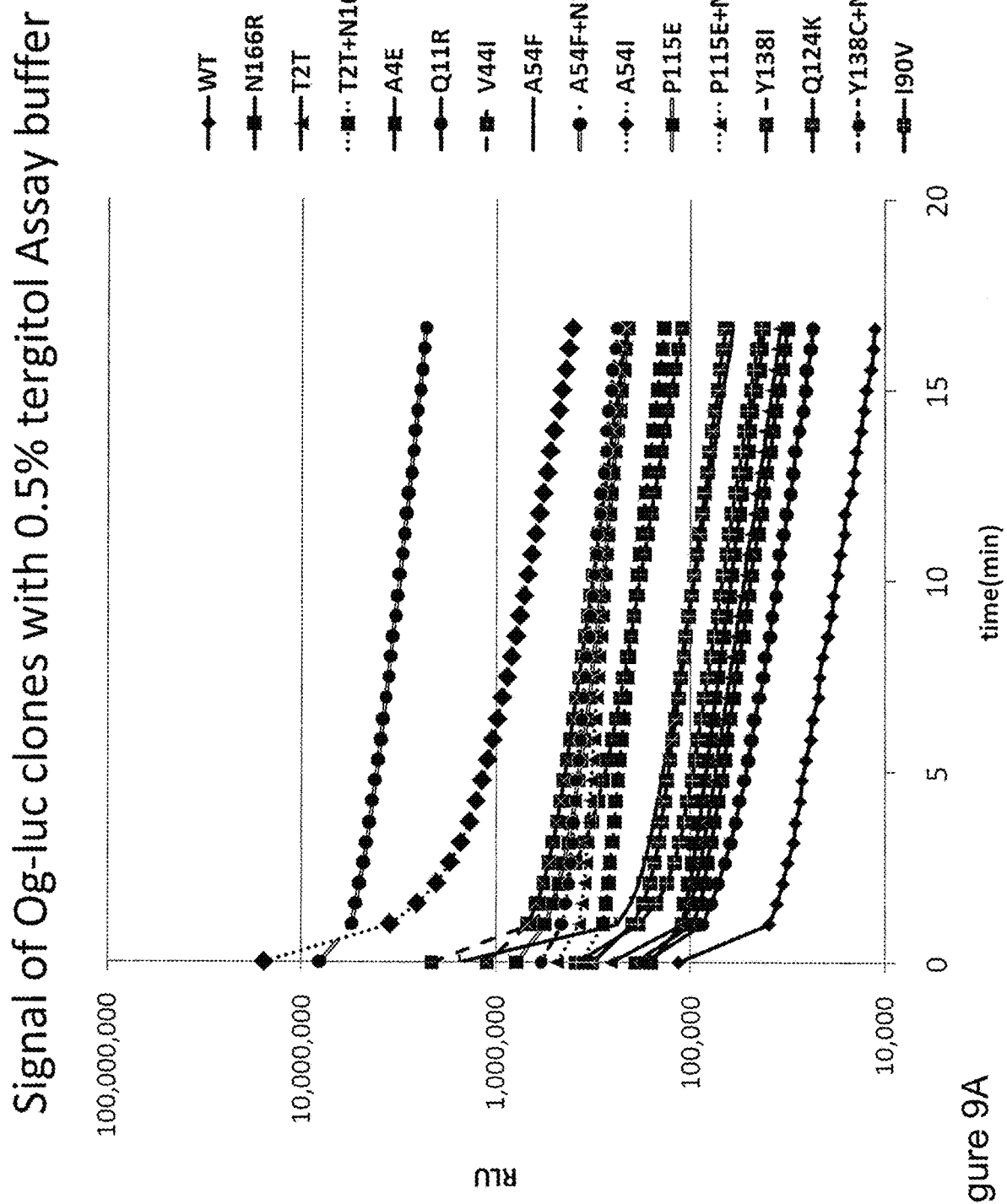
FIGS. 9A-D shows the signal stability of the OgLuc variants compared to WT OgLuc, using a 0.5% tergitol assay buffer. 9A-9C) Light output time course of the OgLuc variants ("clone"), with luminescence measured in RLU over time in minutes. 9D) Signal half-life in minutes of the OgLuc variants determined from light output time course data shown in FIGS. 9A-C.
Figure 9B:
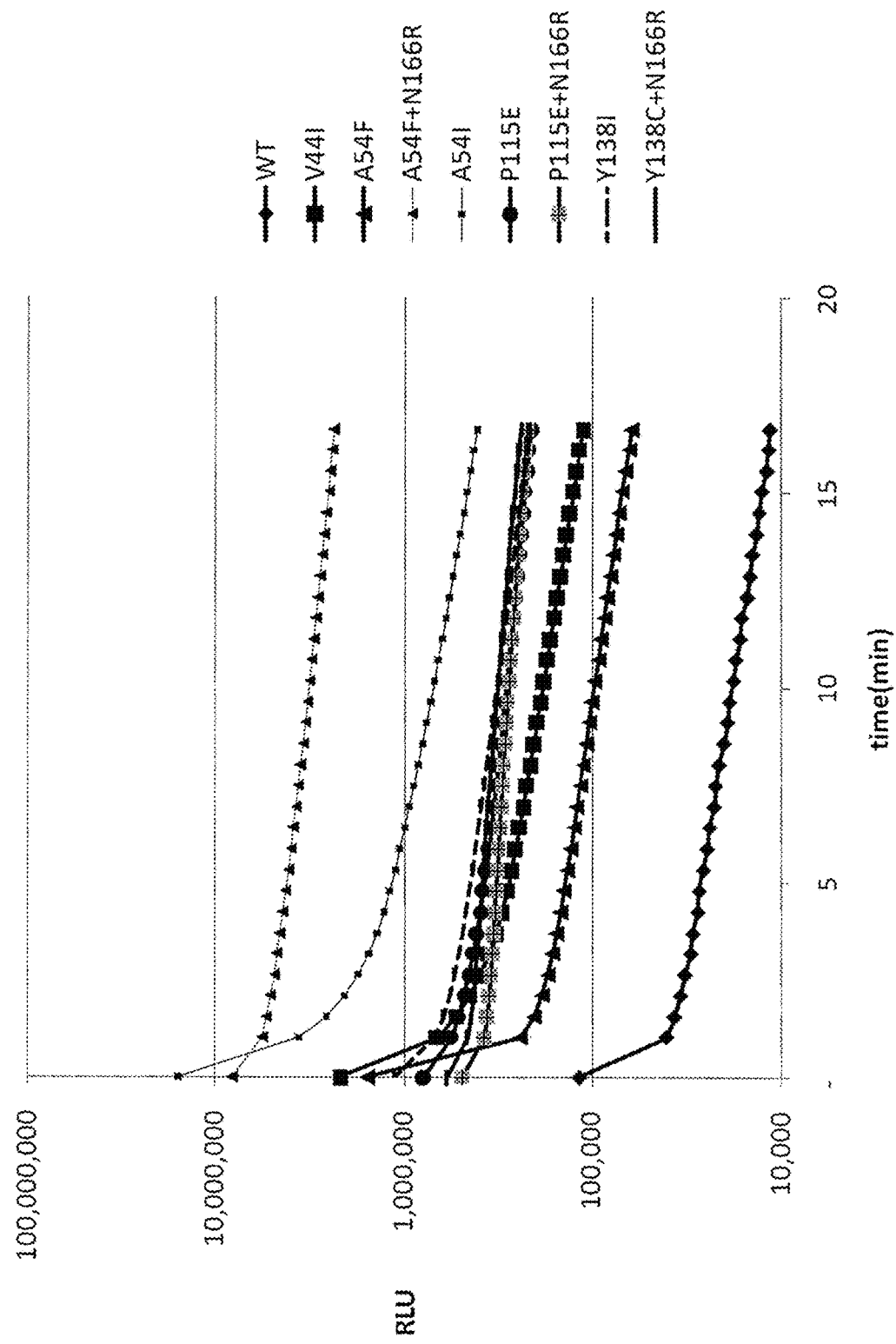
Figure 9C:
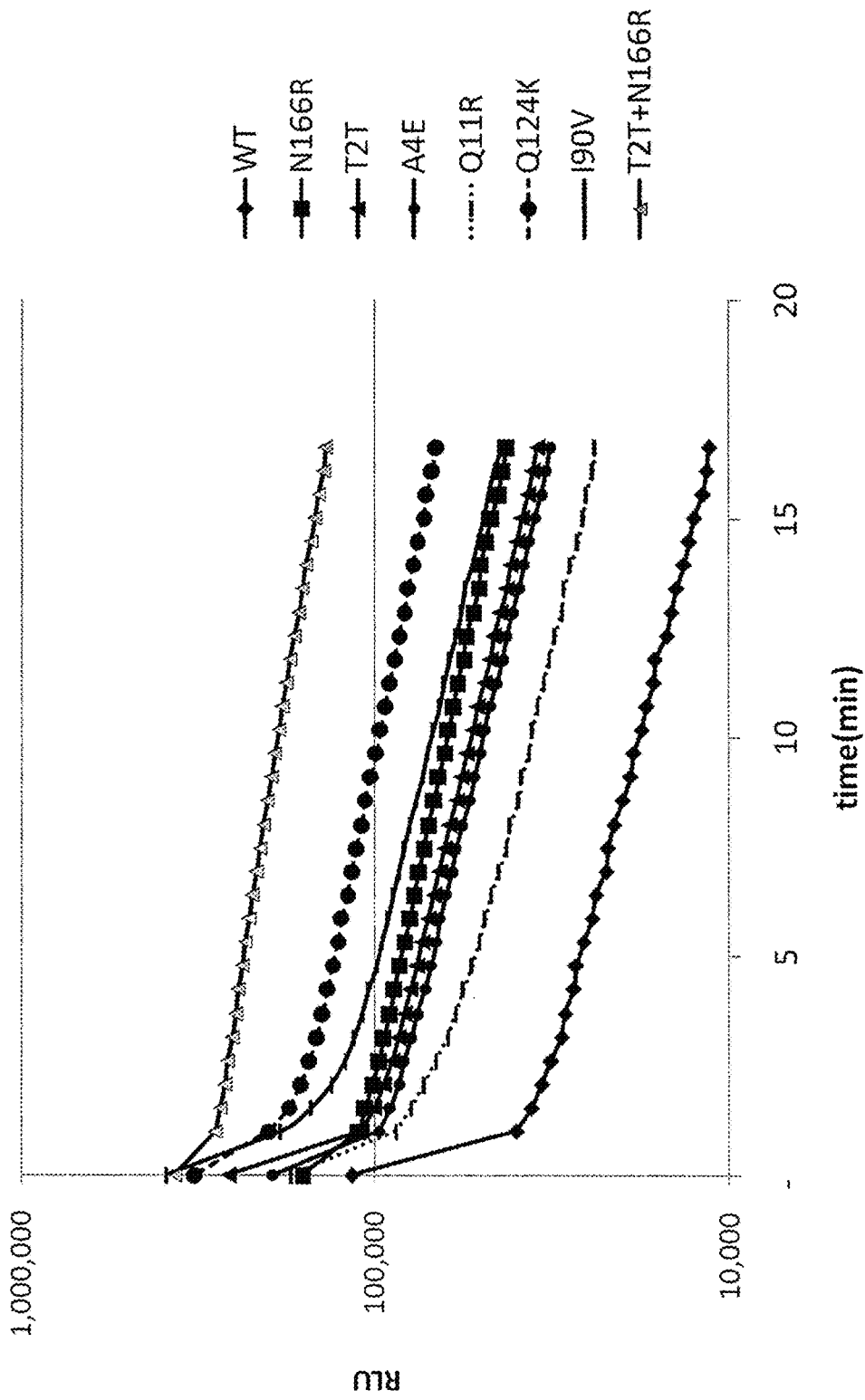
Figure 9D:
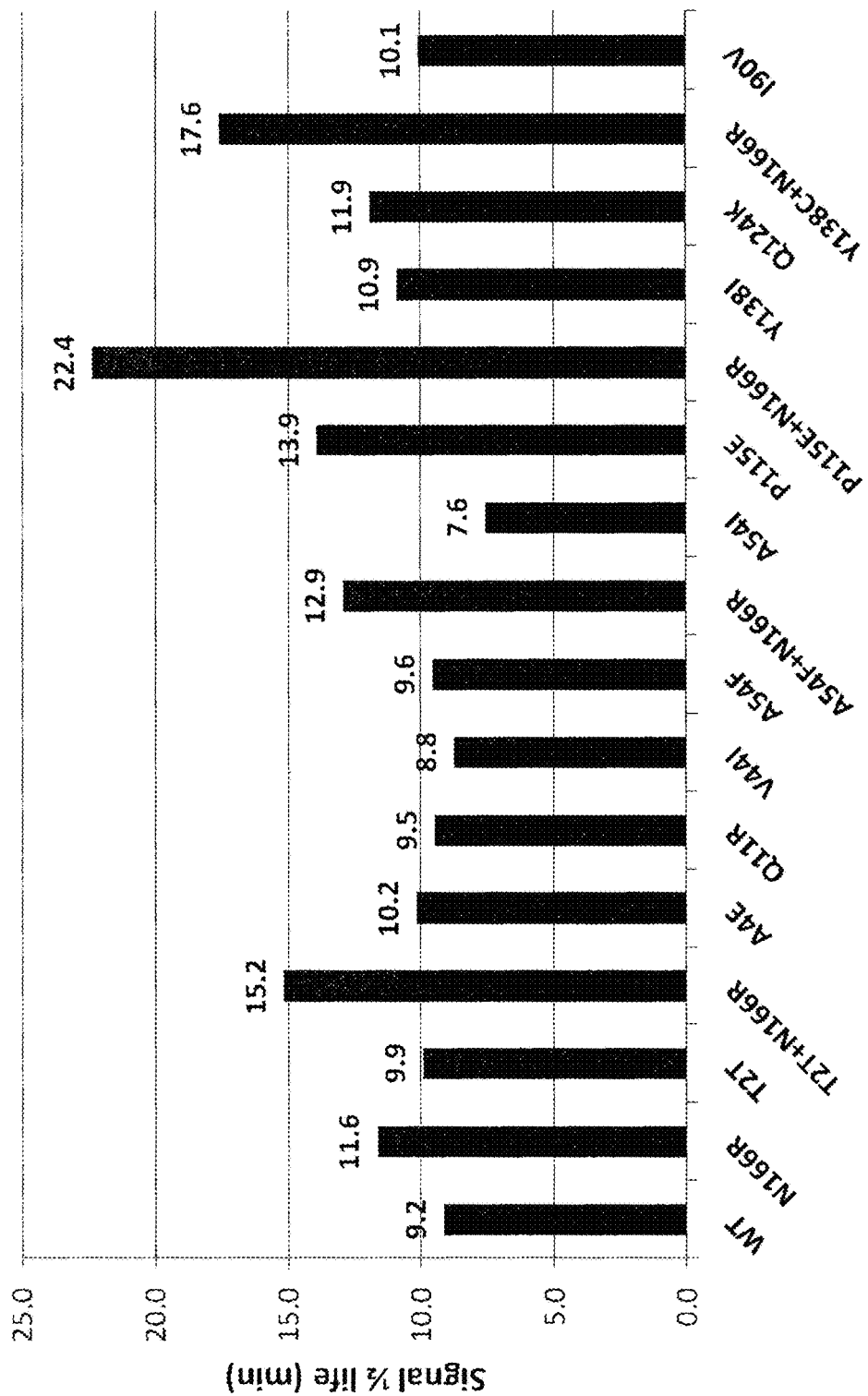
Figure 10A:
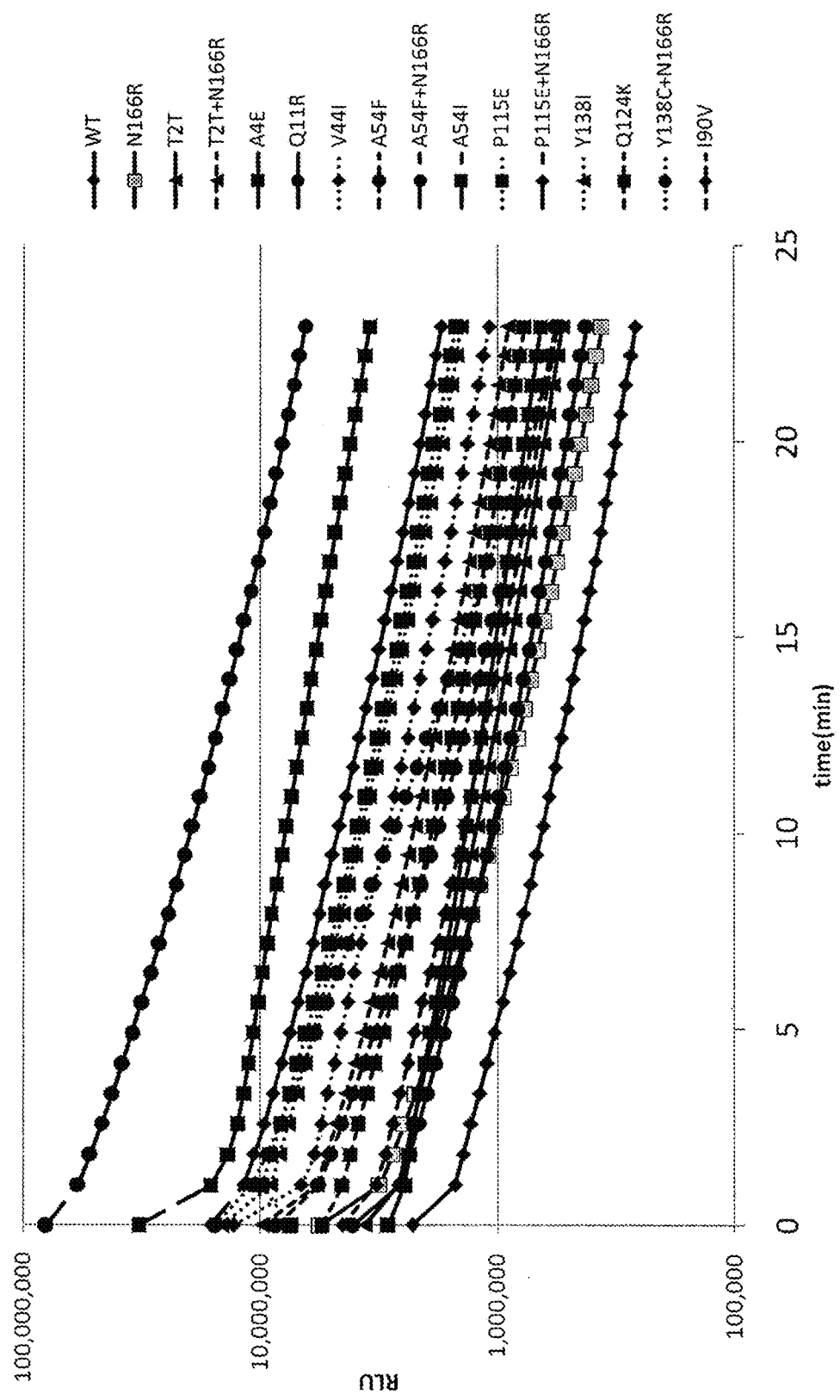
FIGS. 10A-C shows the light output time course (i.e. signal stability) of the OgLuc variants compared to WT OgLuc, using RLAB, with luminescence measured in RLU over time in minutes.
Figure 10B:
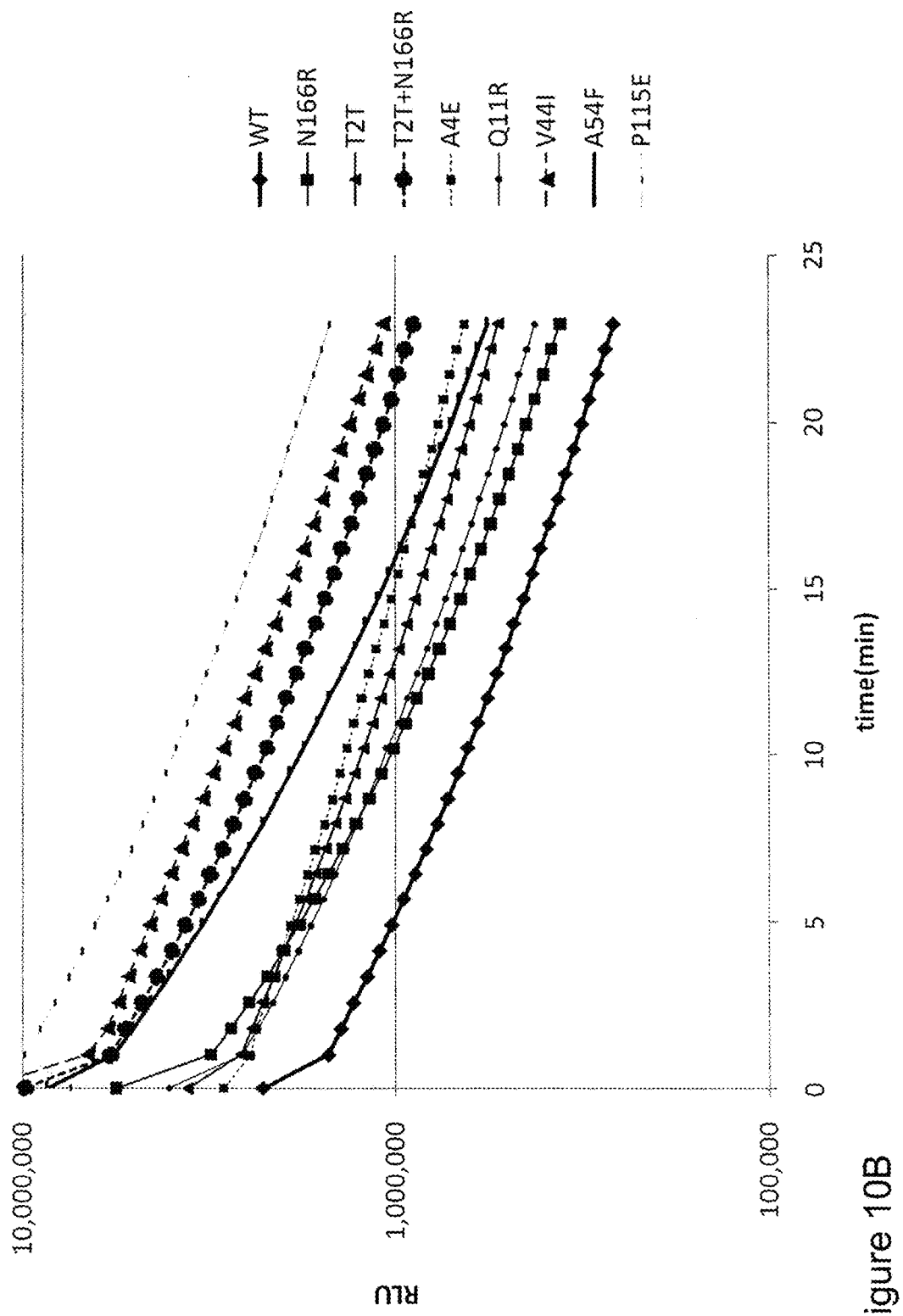
Figure 10C:
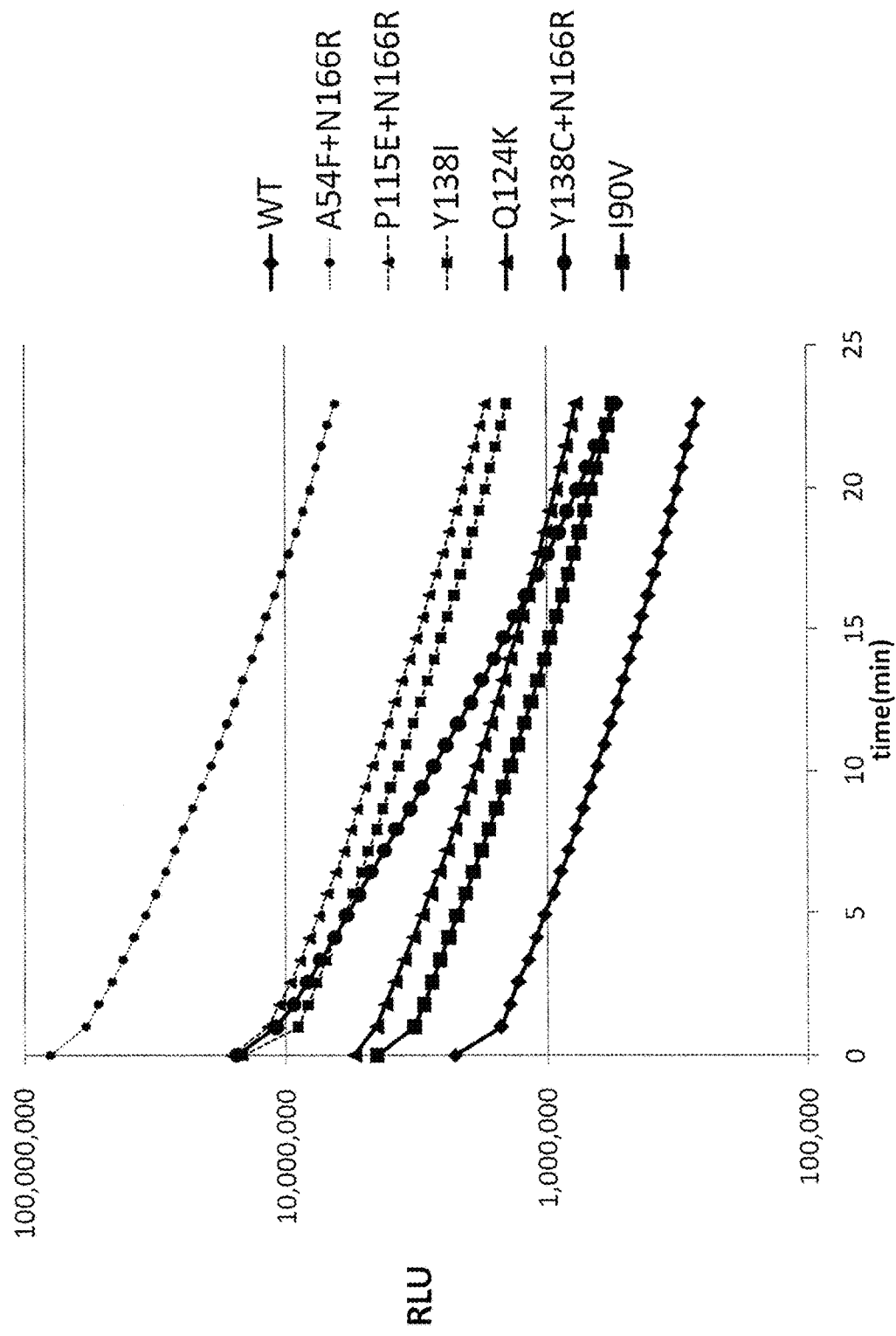
Figure 11B:
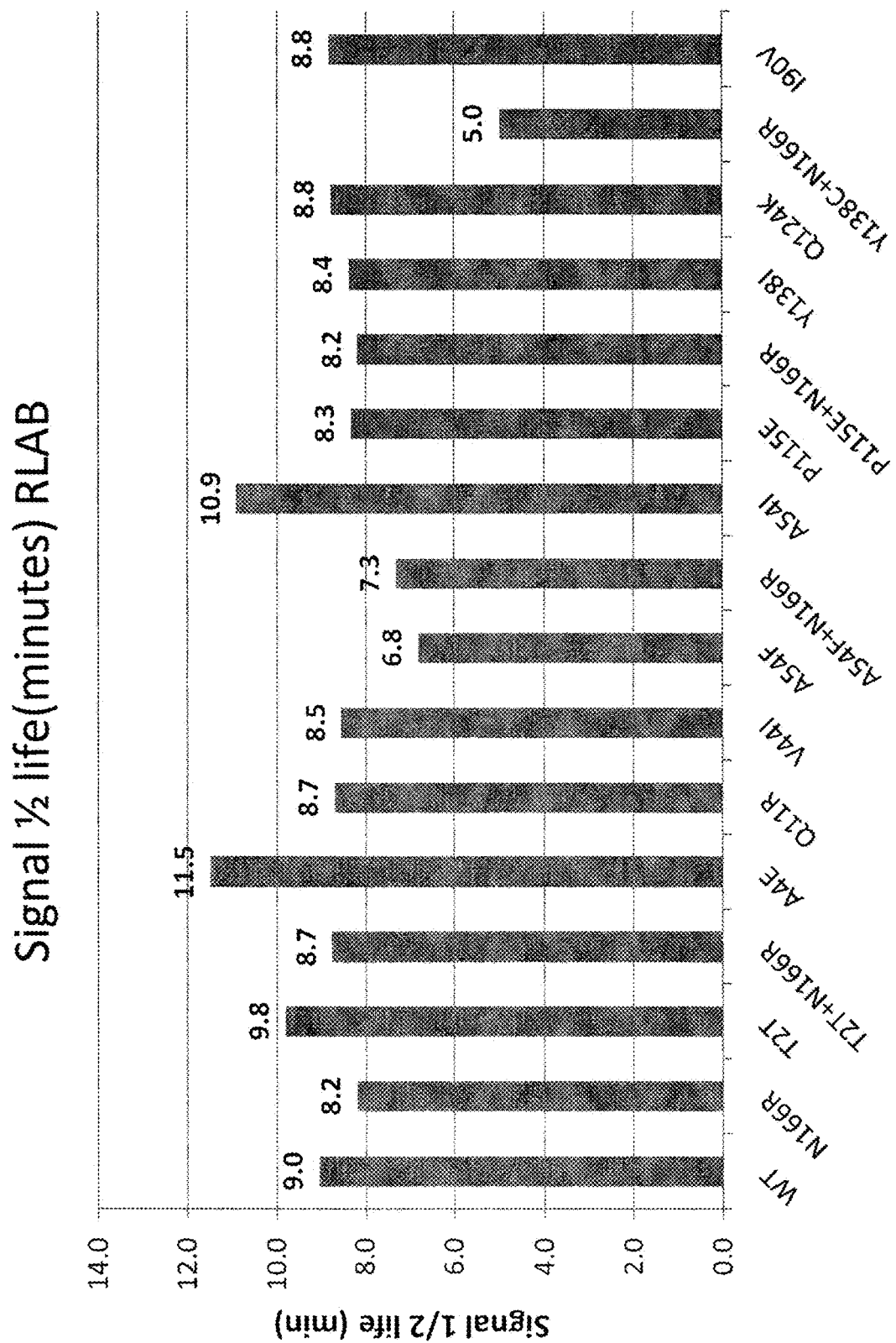
Figure 33A:
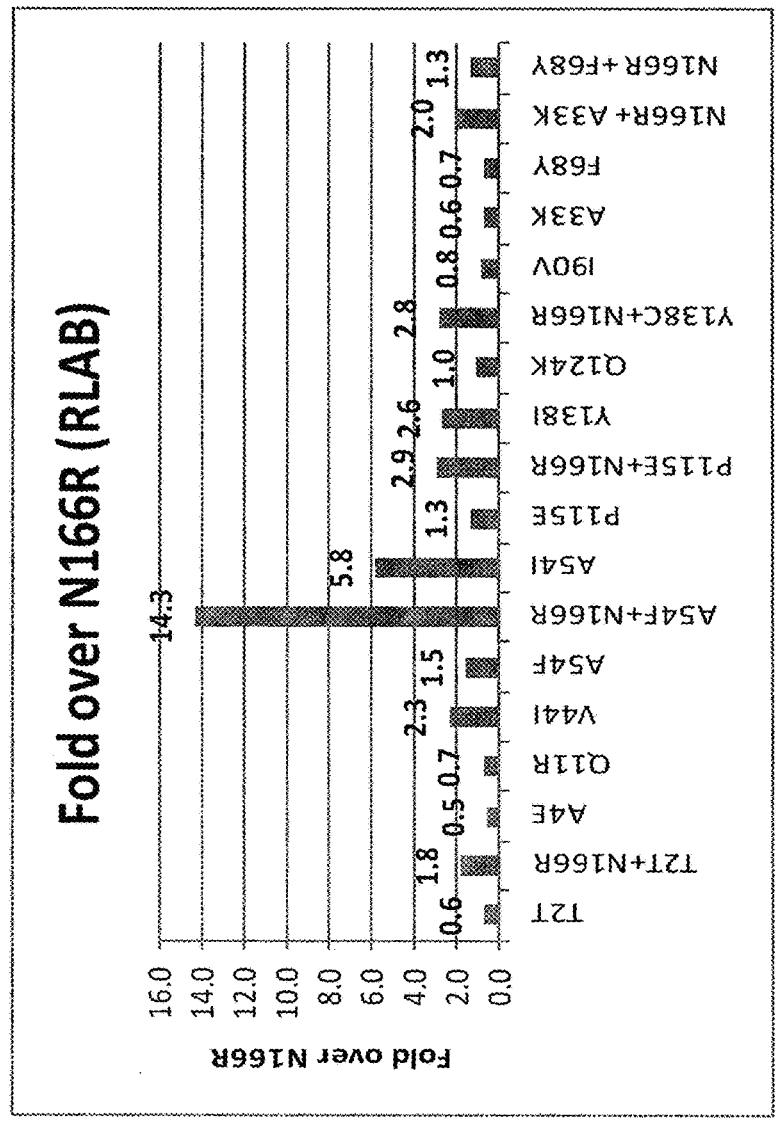
FIG. 33A summarizes the increase fold in luminescence at T=0 of the OgLuc variants over N166R determined from the 0.5% tergitol assay buffer data shown in FIGS. 5A-C and 14A, normalized to the N166R variant.
Figure 33B:
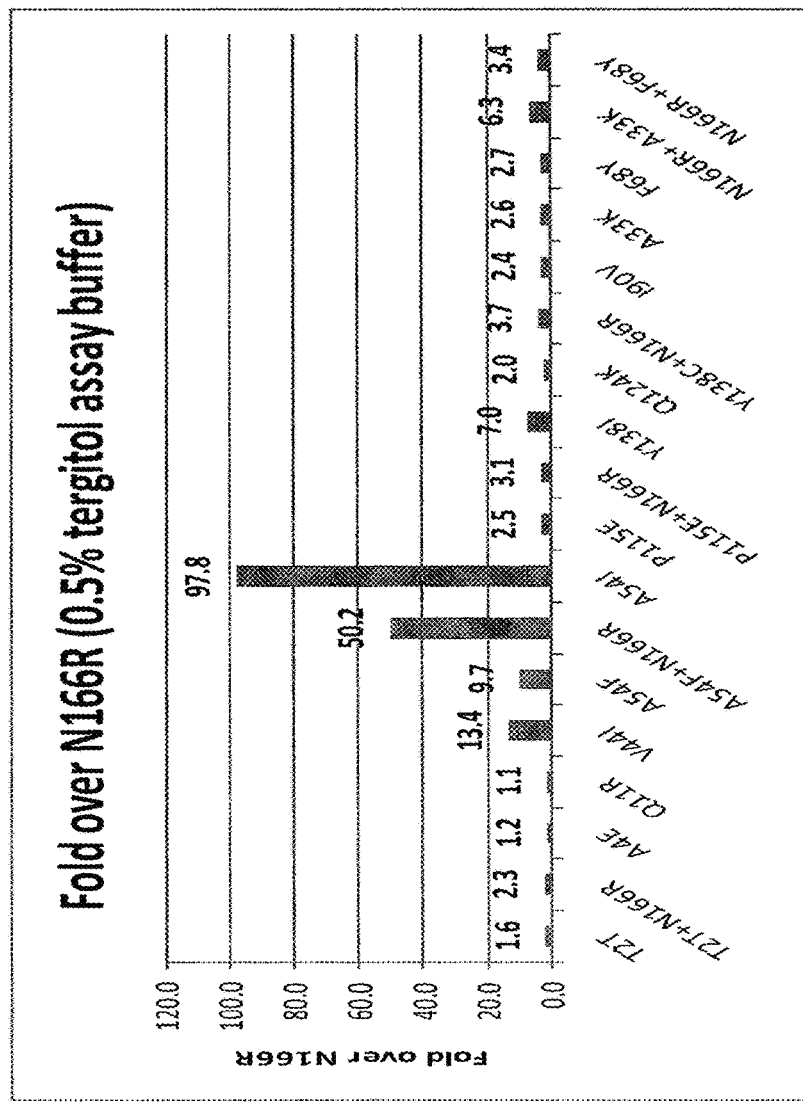
FIG. 33B summarizes the increase fold in luminescence at T=0 of the OgLuc variants over N166R determined from the RLAB data shown in FIGS. 7A-C and 14B, normalized to the N166R variant.

Additional OgLuc variants were generated by site-directed mutagenesis as described in Example 3 to have a substitution at one of the following positions: 2, 4, 11, 44, 54, 90, 115, 124 or 138 relative to SEQ ID NO:1. Substitutions at these positions in combination with N166R, were shown in Example 6 to have increased total light output (luminescence) compared to WT OgLuc. In FIGS. 5A-5C, 6A-6C, 7A-7C, 8, 9A-9D, 10A-10C, 11A-11B, 12A-12B and 33A-33E, "WT," "N166R," and "T2T" refer to the proteins encoded by SEQ ID NOS:2, 14 and 32, respectfully, "T2T+N166R" refers to the protein encoded by SEQ ID NO:32, which has a substitution at N166R, "A4E," "Q11R," "V44I," "A54F," "A54F+N166R," "A54I," "P115E," "P155E+N166R," "Y138I," "Q124K," "Y138C+N166R," and "I90V" each refer to the protein encoded by SEQ ID NO:2 having a substitution at the respective residues indicated in the "Sample" column in FIG. 5A. These variants were evaluated by measuring the luminescence as described in Example 4. FIGS. 5A-5C and 7A-7C summarize the average luminescence at T=0 of the WT OgLuc variants using either 0.5% tergitol (FIG. 5A-5C) or RLAB (FIG. 7A-7C). The fold increase in luminescence of the variants over WT OgLuc is shown in FIGS. 6A-B (0.5% tergitol) and FIG. 8 (RLAB). The fold increase in luminescence of the variants over the N166R variant is shown in FIGS. 33A (0.5% tergitol) and 33B (RLAB). FIGS. 5B, 6B, and 7B show the same data as FIGS. 5C, 6C, and 7C, respectively, but at different scales to permit the smaller bars to be seen more clearly.

To determine if the amino acid substitutions in the different variants also had an effect on signal stability, the signal stability was measured for each variant. The signal stability of the variants was measured as described in Example 4 and shown in FIG. 9A-9C (0.5% tergitol) and FIGS. 10A-10C (RLAB) as the total light output (luminescence) over time. The signal half-life of each variant was determined from this data and shown in FIG. 9D (0.5% tergitol) and FIGS. 11A-11B (RLAB). The signal half-life for each variant was normalized to the N166R variant and shown in FIG. 33C.

To determine if the amino acid substitutions in the different variants also had an effect on protein stability (i.e. thermostability), the protein stability of each variant at 22°

Figure 12B:
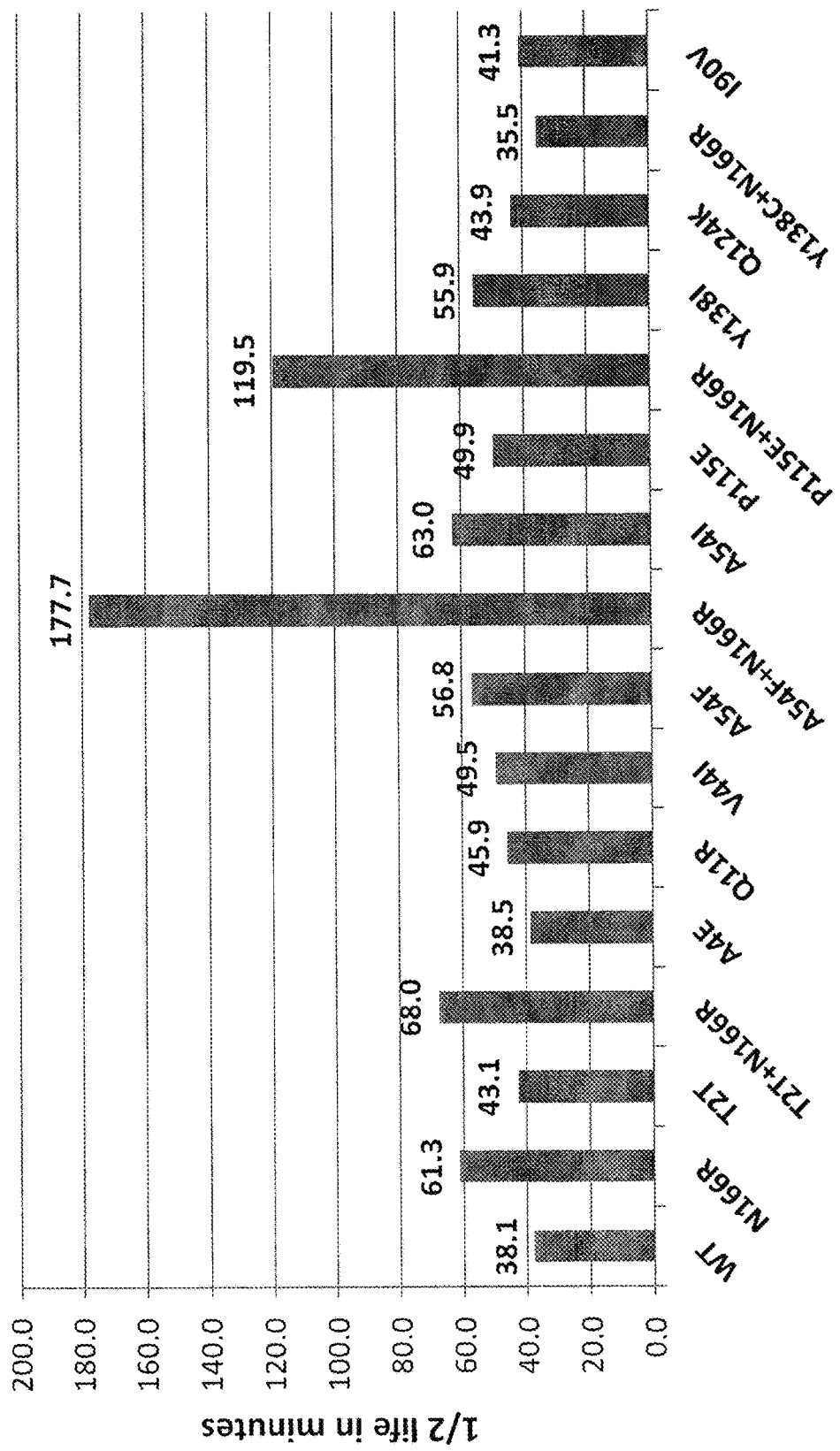

C. was measured as described in Example 5 and shown in FIGS. 12A-12B. At 22° C., the OgLuc A54F+N166R variant protein had a half-life of 178 minutes, while the OgLuc P115E+N166R variant had a half-life of almost 120 minutes, compared to WT OgLuc, which had a half-life of 38 minutes.

FIG. 33D summarizes the half-life in minutes at 22° C. of the OgLuc variants compared to WT OgLuc shown in FIGS. 12A-B and 17 normalized to the N166R variant.

FIG. 33E summarizes the increase fold in luminescence, signal half-life and half-life at 22° C. shown in Figures A-D.

Example 8

Evaluation of Specific Substitutions in Modified Luciferases

Figure 13A:
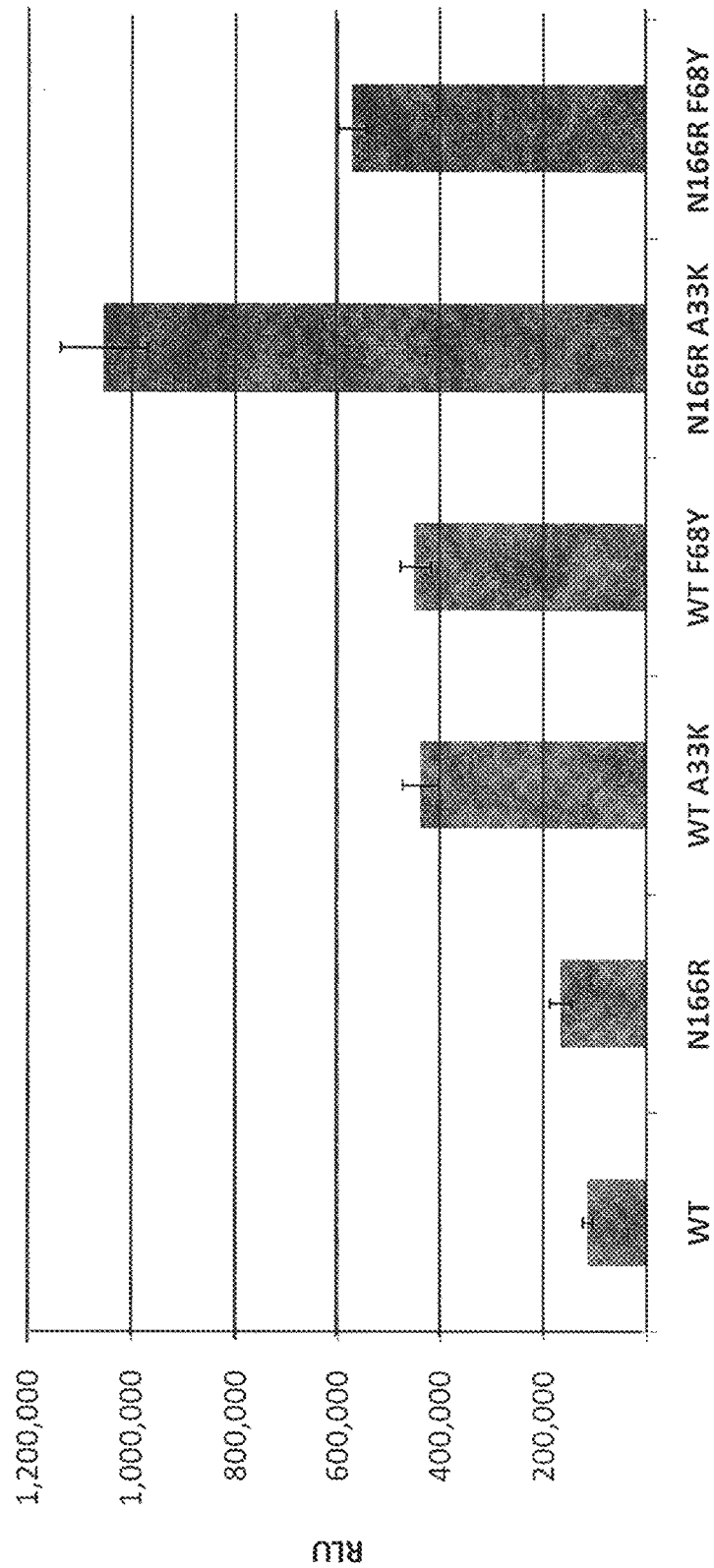
FIGS. 13A-B summarize the average luminescence in RLU of the A33K and F68Y OgLuc variants at T=0 ("Average"), with coefficient of variance ("% cv"), compared to WT OgLuc, using 0.5% tergitol assay buffer (13A) or RLAB (13B).
Figure 13B:
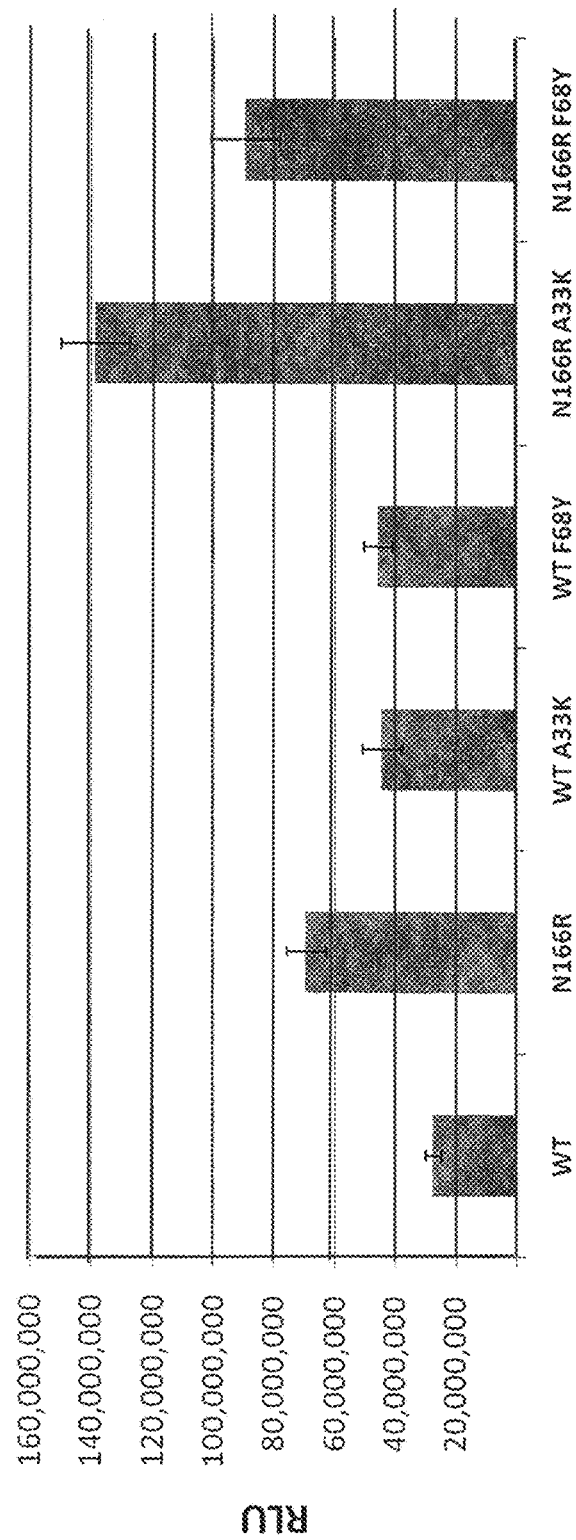
Figure 14A:
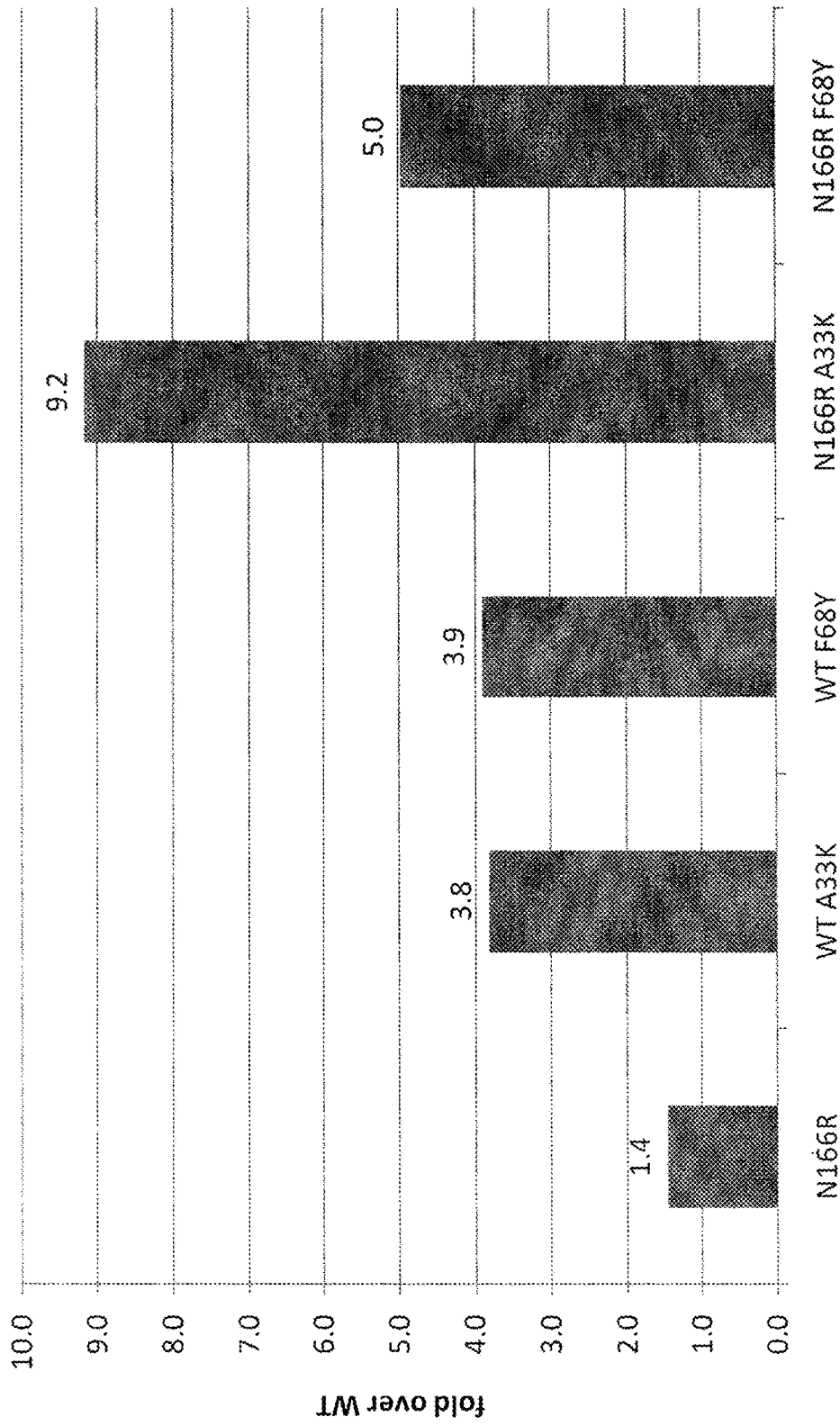
FIGS. 14A-B summarize the increase fold in luminescence at T=0 of the A33K and F68Y OgLuc variants over WT OgLuc, determined from the data shown in FIGS. 13A-B for assays using 0.5% tergitol assay buffer (14A) or RLAB (14B), respectively.
Figure 14B:
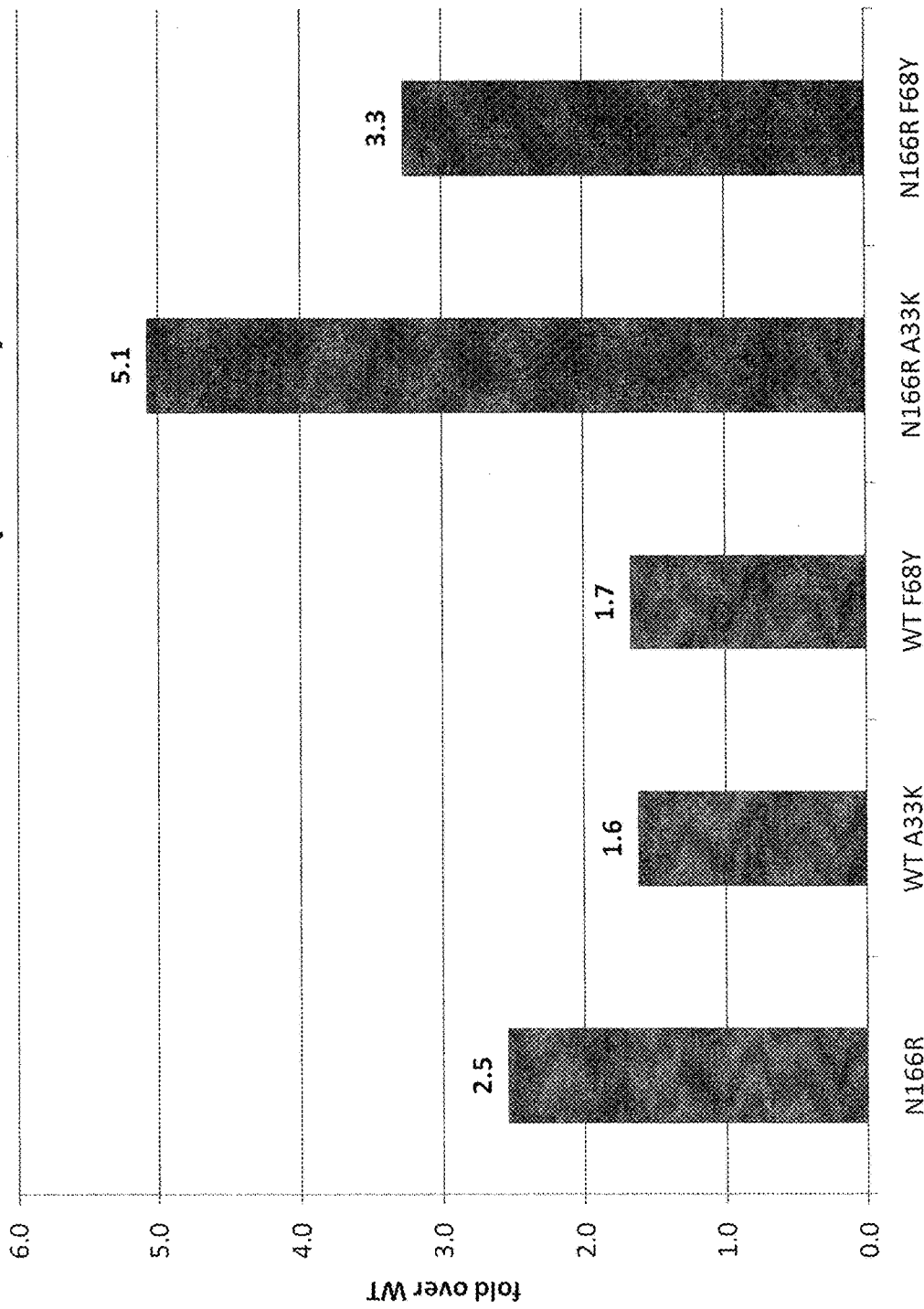

Additional synthetic OgLuc variants were generated with substitutions at sites 33 and 68. Specifically, A33K and F68Y substitutions were made in WT OgLuc (identified as "WT A33K" and "WT F68Y" in FIGS. 13A-13B, 14A-14B, 15A-15B, 16A-16B, 17, and 33A-33E) and the OgLuc+ N166R (identified as "N166R A33K" and "N166R F68Y" in FIGS. 13A-13B, 14A-14B, 15A-15B, 16A-16B, 17, and 33A-33E) variant sequence and compared with the corresponding starting WT OgLuc (identified as "WT" in FIGS. 13A-13B, 14A-14B, 15A-15B, 16A-16B, 17, and 33A-33E) and OgLuc+N166R variant (identified as "N166R" in FIGS. 13A-13B, 14A-14B, 15A-15B, 16A-16B, 17, and 33A-33E). The average luminescence at T=0 of the OgLuc A33K and F68Y variants using 0.5% tergitol and RLAB are shown in FIGS. 13A and 13B, respectively. The A33K and F68Y variants had higher luminescence compared to the respective corresponding starting OgLuc as further shown with the fold increase in luminescence of the variants over the WT OgLuc in FIGS. 14A (0.5% tergitol) and 14B (RLAB). A33K and F68Y separately in the wild-type background showed 1.6 and 1.7 fold increase over WT using RLAB (see FIG. 14B) and 3.8 and 3.9 fold increase over WT 0.5% tergitol (FIG. 14A). A33K and F68Y separately in the OgLuc+N166R background showed 5.1 and 3.3 fold increase over WT OgLuc using RLAB (see FIG. 14B) and 9.2 and 5 fold increase over WT OgLuc using 0.5% tergitol (FIG. 14A).

The fold increase in luminescence of the variants over the OgLuc+N166R variant is shown in FIGS. 33A (RLAB) and 33B (0.5% tergitol). The substitution A33K in the wild-type background showed 2.6 (0.5% tergitol) and 0.6 (RLAB) fold increase in luminescence over the OgLuc+N166R variant. (see FIGS. 33A and 33B). The substitution F68Y in the wild-type background showed 2.7 (0.5% tergitol) and 0.7 (RLAB) fold increase over the OgLuc+N166R variant (see FIGS. 33A and 33B). The substitution A33K in the OgLuc+ N166R variant background showed 6.3 (0.5% tergitol) and 2.0 (RLAB) fold increase over the OgLuc+N166R variant (see FIGS. 33A and 33B). The substitution F68Y in the OgLuc+N166R background showed 3.4 (tergitol) and 1.3 (RLAB) fold increase over N166R (see FIGS. 33A and 33B).

Figure 15A:
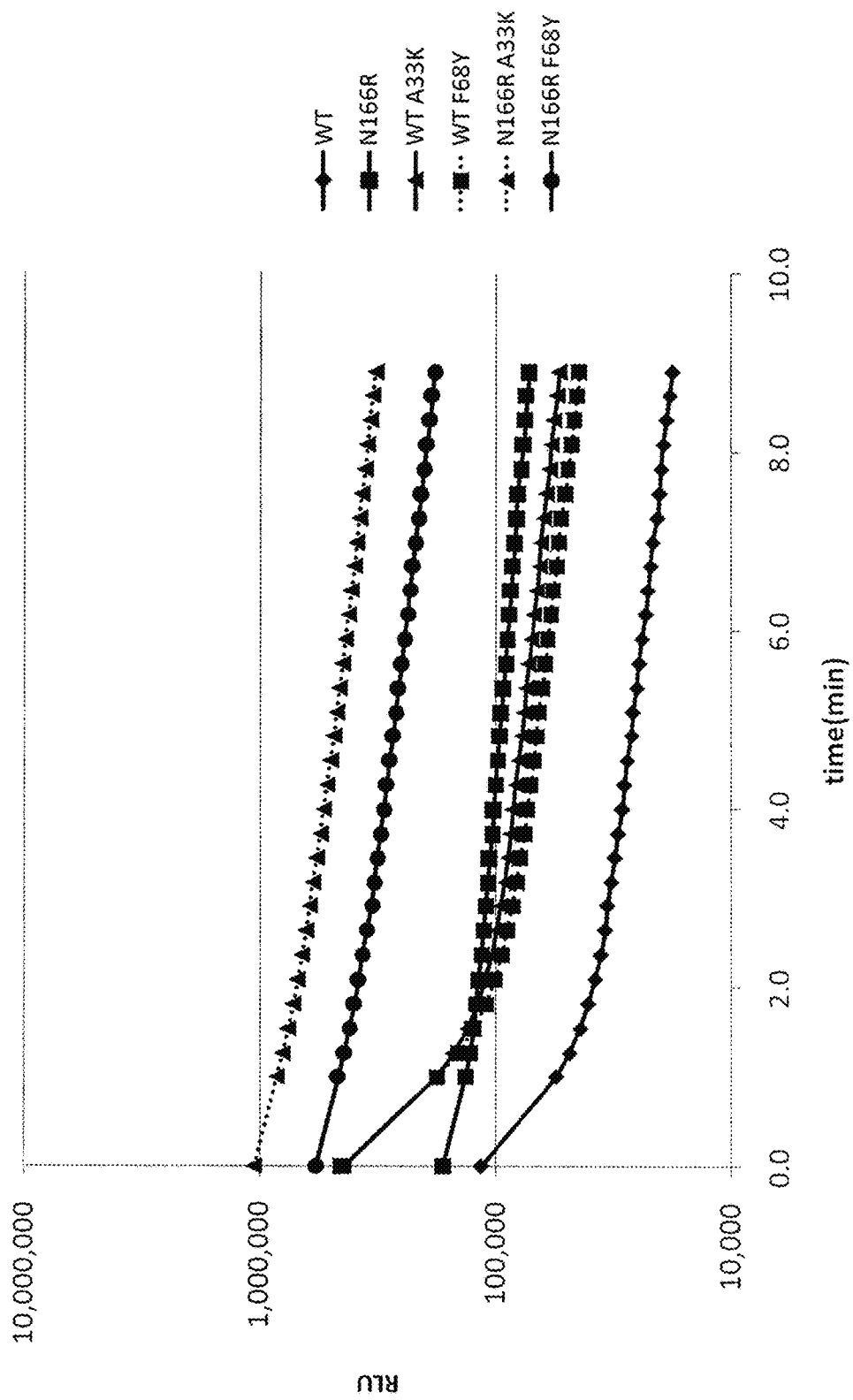
Figure 16A:
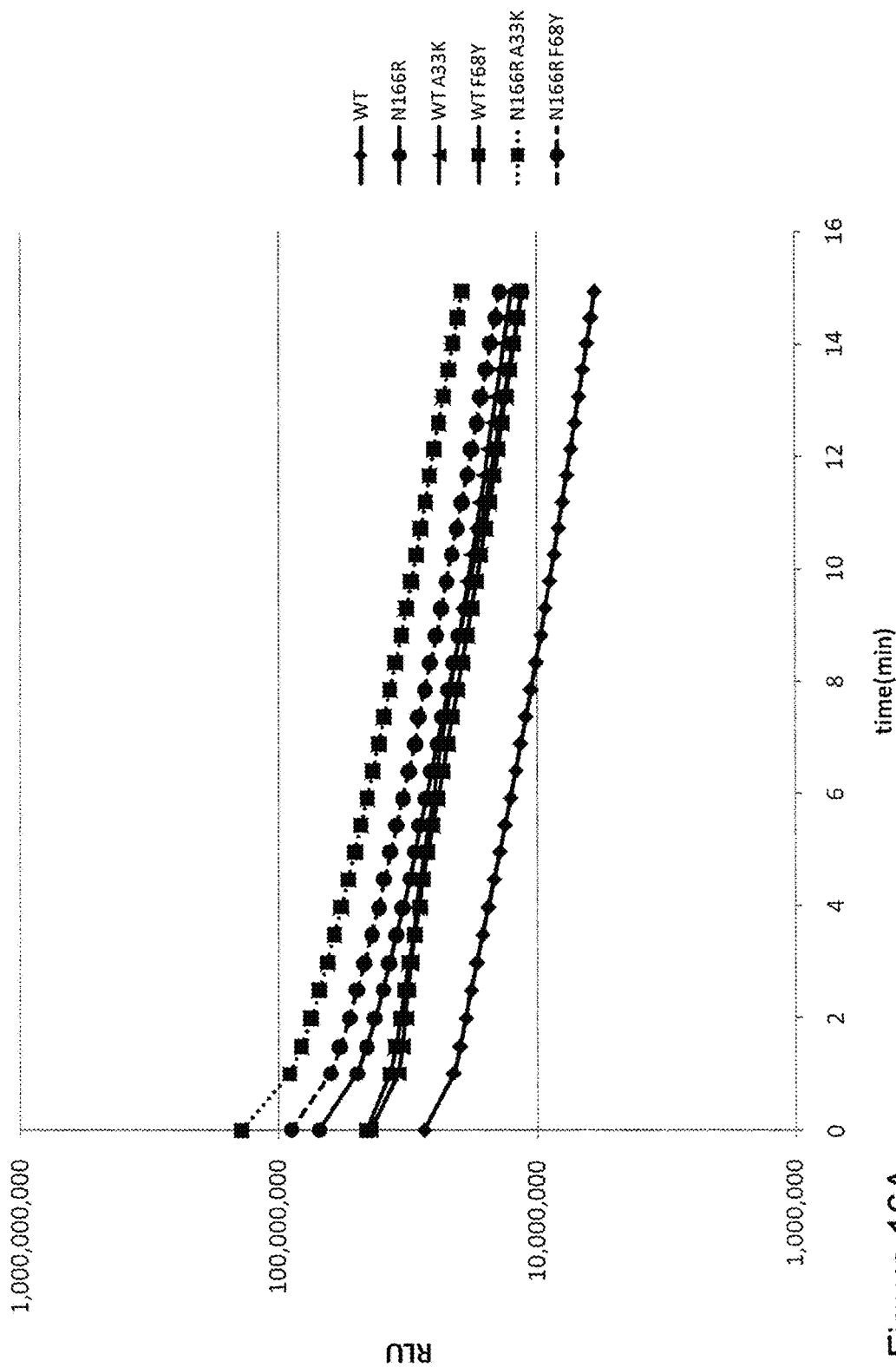

The signal stability of the A33K and F68Y variants was measured as described in Example 4 using 0.5% tergitol (FIGS. 15A-15B) and RLAB (FIGS. 16A-16B). The signal half-life of the A33K variant in the WT OgLuc background was higher than the WT OgLuc half-life, but lower in the OgLuc+N166R variant background when using either 0.5% tergitol (FIG. 15B) or RLAB (FIG. 16B). The signal half-life of the F68Y variant in the WT OgLuc background was higher than the WT OgLuc half-life using 0.5% tergitol (FIG. 16B), but lower in either background using RLAB (FIG. 15B).

The protein stability (i.e. thermostability) of the A33K and F68Y variants was measured as described in Example 5 at 22° C. and shown in FIG. 17. The A33K and F68Y substitutions in the N166R variant background had a longer half-life, specifically 72 and 78 minutes compared to WT OgLuc and the N166R variant, which was 55 and 67 minutes, respectively (FIG. 17). The A33K and F68Y substitutions in the WT OgLuc background, had 58 and 57 minutes half-lives, respectively (FIG. 17).

Example 9

Figure 4A:
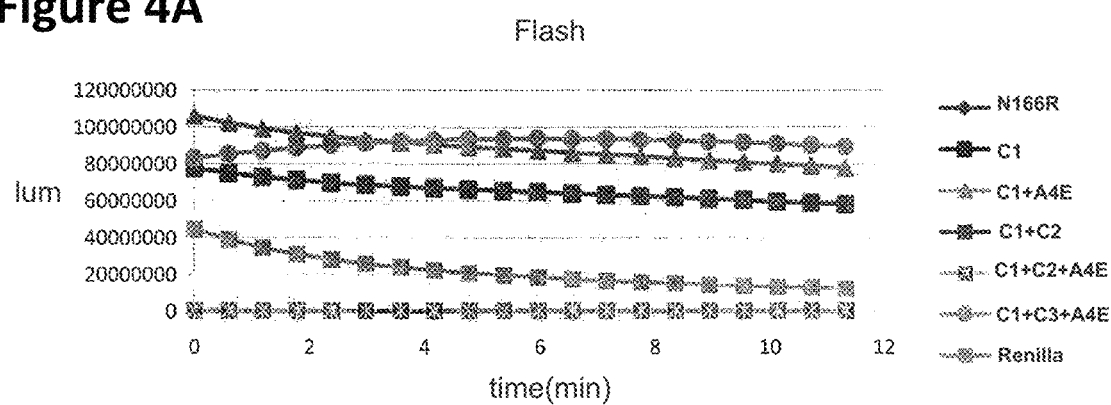
FIGS. 4A-D shows the light output (i.e. luminescence) time course of OgLuc variants modified with a combination of two or more amino acid substitutions in OgLuc compared with the N166R OgLuc variant and *Renilla* luciferase. 4A-4B) Luminescence ("lum") in relative light units (RLU) using a "Flash" luminescence assay shown on two different luminescence scales over time in minutes. 4C-4D) Luminescence ("lum") in RLU using a "Glo" 0.5% tergitol luminescence assay shown on two different luminescence scales over time in minutes.
Figure 4B:
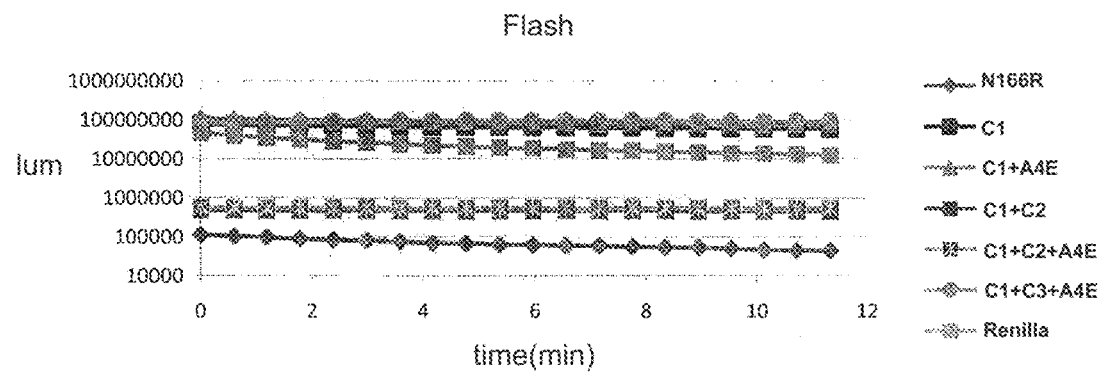
Figure 4C:
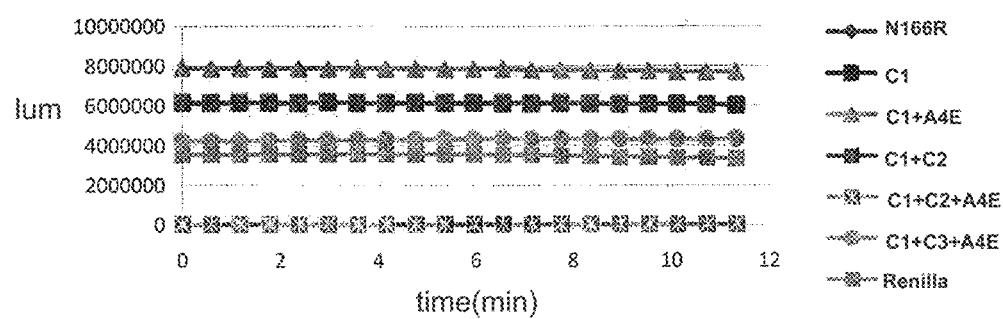
Figure 4D:
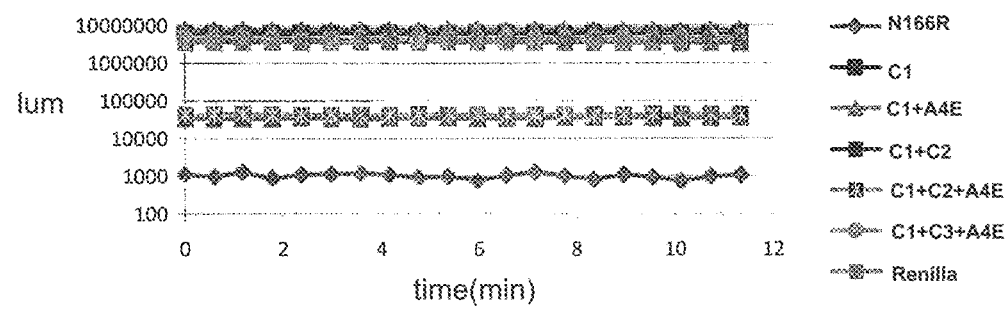

Evaluation of Specific Core Combinations of Substitutions in Modified Luciferases—Light Emission To determine if a combination of two or more amino acid substitutions in OgLuc provides a further improvement in luminescence, different variants (designated C1-C3) of OgLuc were generated containing the following amino acid substitutions: C1: N166R, Q11R, A33K, A54F, P115E, Q124K, Y138I and V44I (residue 44 may come into contact with substrate), C2: V45E, N135K, I167V, P104L, and D139E (note that 2 of these are at sites that may come into contact with substrate); C3; S28P, L34M, G51V, I99V, and I143L. These Core Combination variants were generated by mutating the T2T OgLuc by site-directed mutagenesis as described in Example 3. The C1 variant was further mutated to contain an A4E amino acid substitution to create the C1+A4E variant. Combinations of these variants were also created with the A4E substitutions, e.g., C1+C2+A4E and C1+C3+A4E. These recombinant clones were constructed using oligonucleotide-based site-directed mutagenesis followed by subcloning into pF4Ag vector (contains T7 and CMV promoters; commercially-available pF4A modified to contain an *E. coli* ribosome-binding site). All variants were screened in *E. coli* cells. Briefly, clones were overexpressed in KRX *E. coli*, after which cells were lysed and measured for luminescence using colenterazine as a substrate. The OgLuc N166R variant and *Renilla* luciferase were also screened. Both C1, C1+A4E and C1+C3+A4E variants were approximately 4 logs brighter than the OgLuc N166R variant and at least as bright as *Renilla* luciferase (FIG. 4A-4D). The total light output (i.e. luminescence) of these Core Combination variants at T=0 was measured as described in Example 4 using the "Flash" 0.5% tergitol (FIG. 4A) and the "Glo" RLAB (FIG. 4B).

Figure 31:
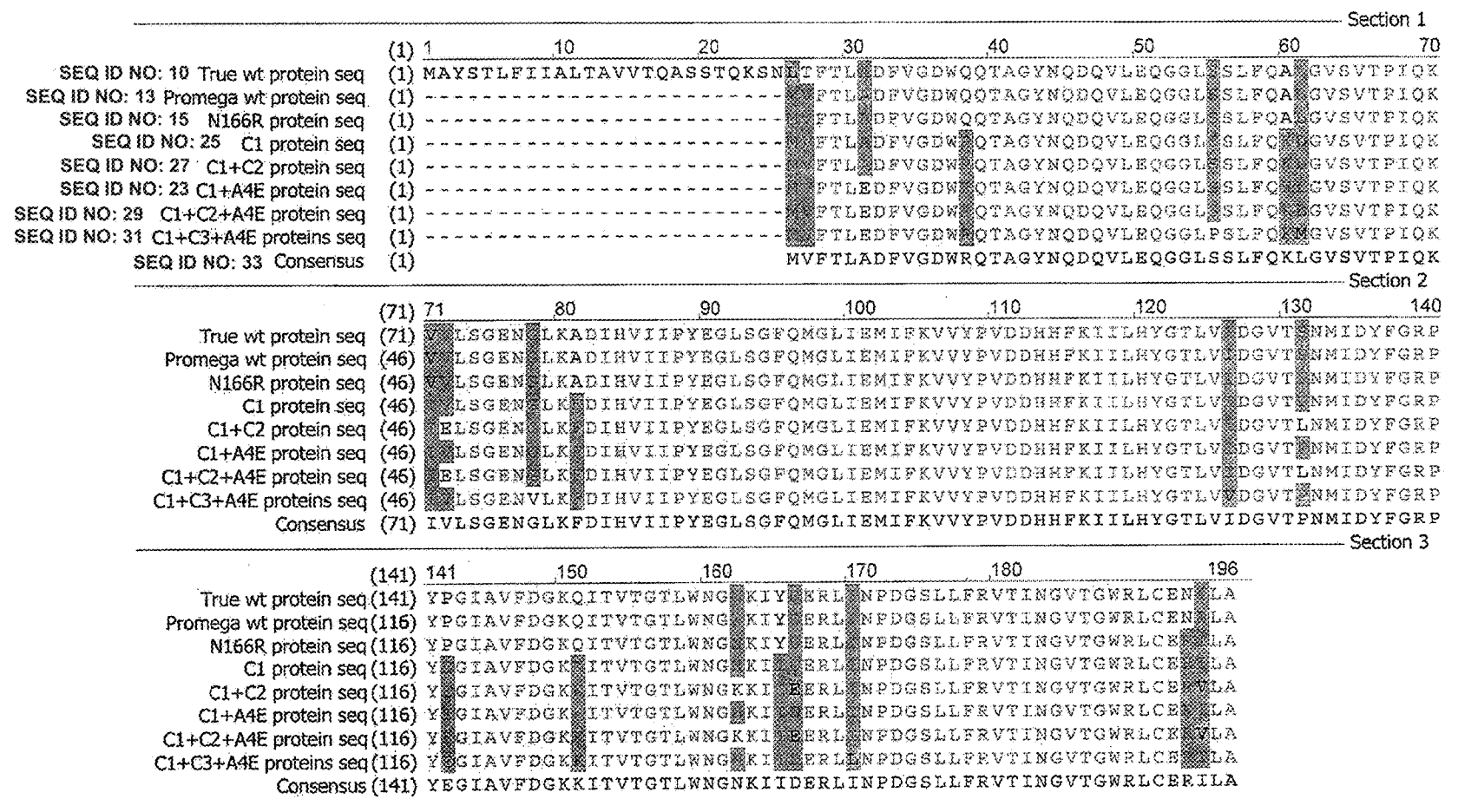
Figure 32:
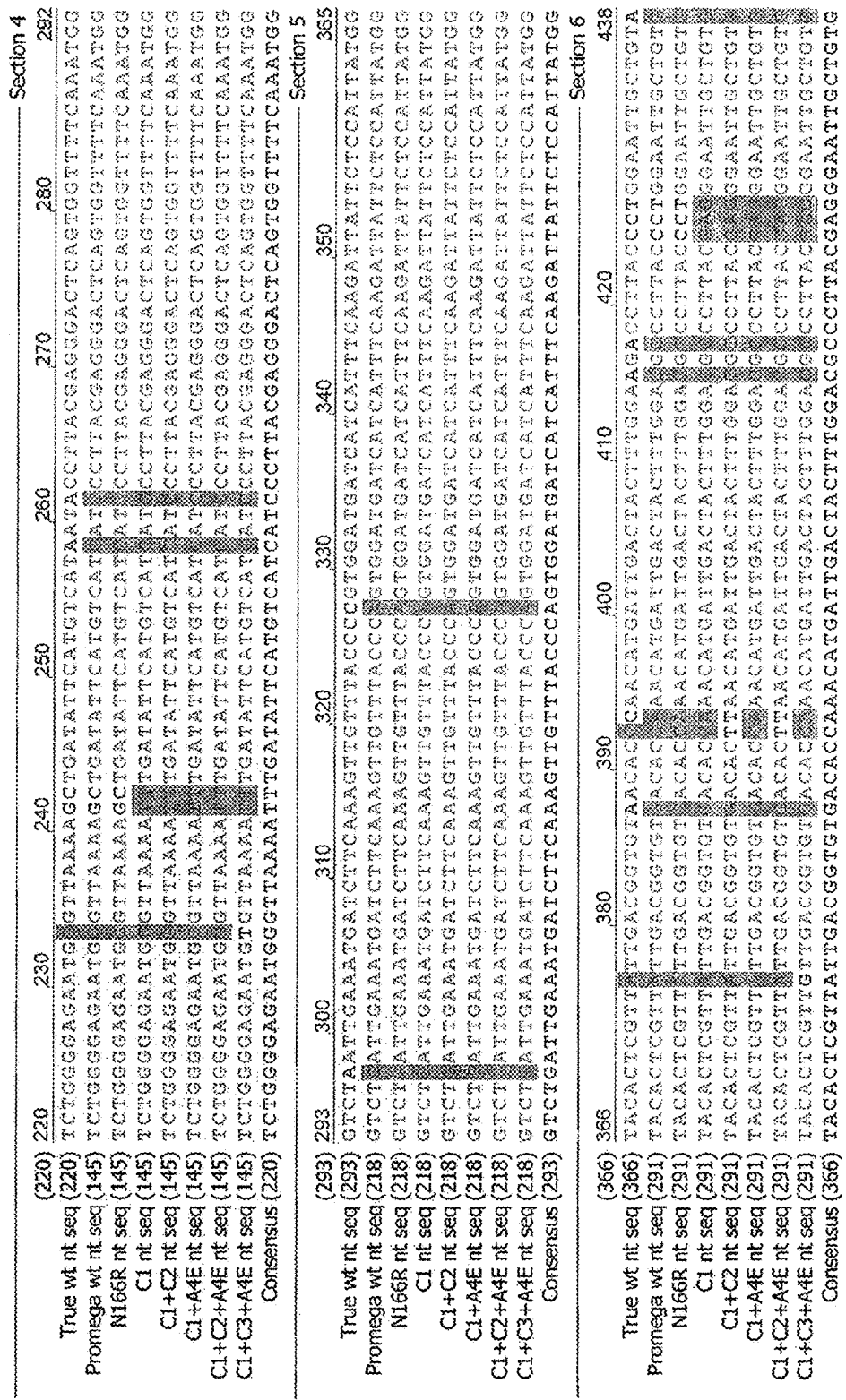
FIG. 32 shows the nucleotide sequence alignment of SEQ ID NO:12 (NATIVE), SEQ ID NO:2 (Synthetic WT), SEQ ID NO:14 (N166R), SEQ ID NO:18 (C1), SEQ ID NO:20 (C1+C2), SEQ ID NO:16 (C1+A4E), SEQ ID NO:22 (C1+C2+A4E), and SEQ ID NO: 24 (C1+C3+A4E) with the consensus sequence.

An alignment of the protein (FIG. 31) and nucleotide (FIG. 32) sequences of the native, WT, N166R, C1, C1+C2, C1+A4E, C1+C2+A4E, and C1+C3+A4E is shown.

Figure 18B:
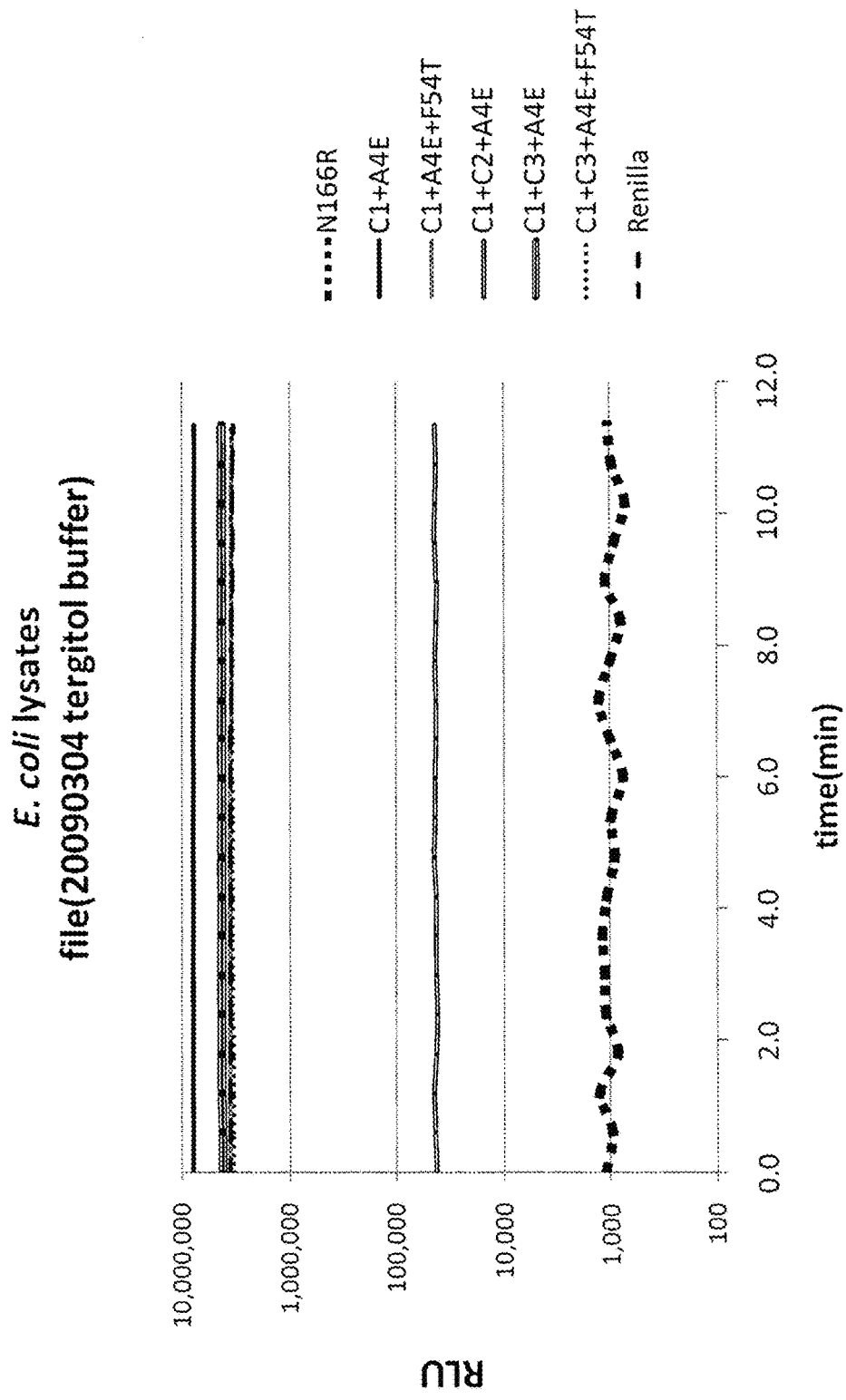
Figure 19:
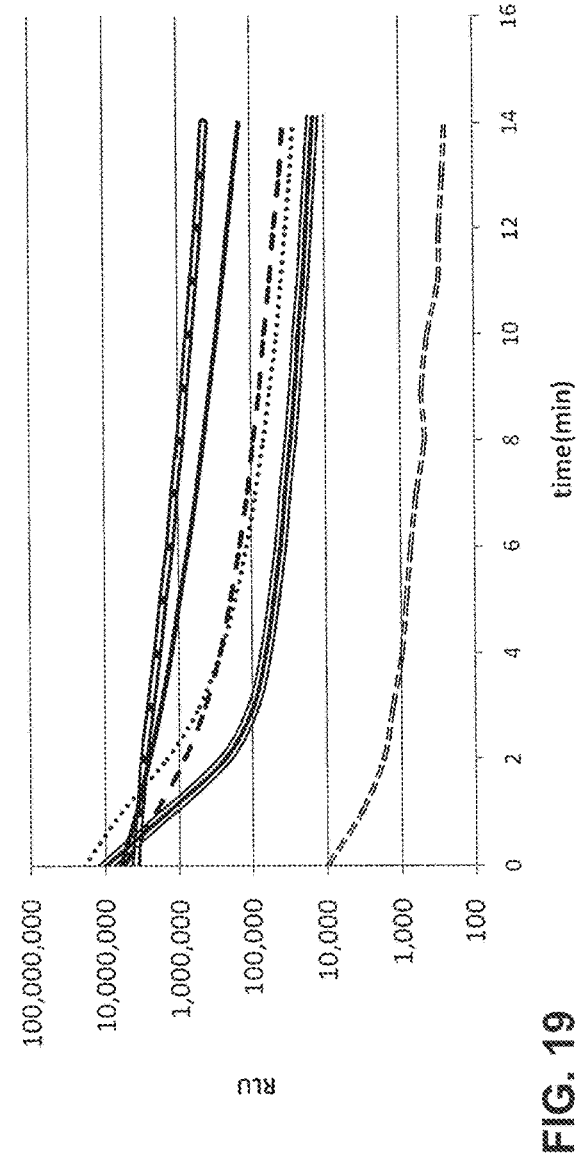
FIG. 19 shows the light output time course (i.e. signal stability) of the Core Combination OgLuc variants compared to the N166R OgLuc variant and *Renilla* luciferase, using RLAB, with luminescence measured in RLU over time in minutes.

An additional substitution was introduced into C1+A4E and C1+C3+A4E. Specifically, the A54F residue in these variants was changed to F54T. These variants, C1+A4E+ F54T and C1+C3+A4E+F54T, were compared to the corresponding starting C1+A4E and C1+C3+A4E, as well as *Renilla* and WT OgLuc luciferases using the method of Example 4. As seen in FIGS. 18A, 18B and 19, the variants with the F54T substitution had a 50-75% decrease with 0.5% tergitol and about 2-5 fold increase in luminescence with RLAB compared to WT (see T=0 measurement in FIGS. 18A and 19, respectfully). The addition of the F54T substitution showed increased total light output with RLAB, but showed a faster decay over time (FIG. 19). With 0.5% tergitol, the decay over time is similar to C1+A4E, but the RLU's are lower compared to C1+A4E (FIG. 18A-18B).

Figure 20A:
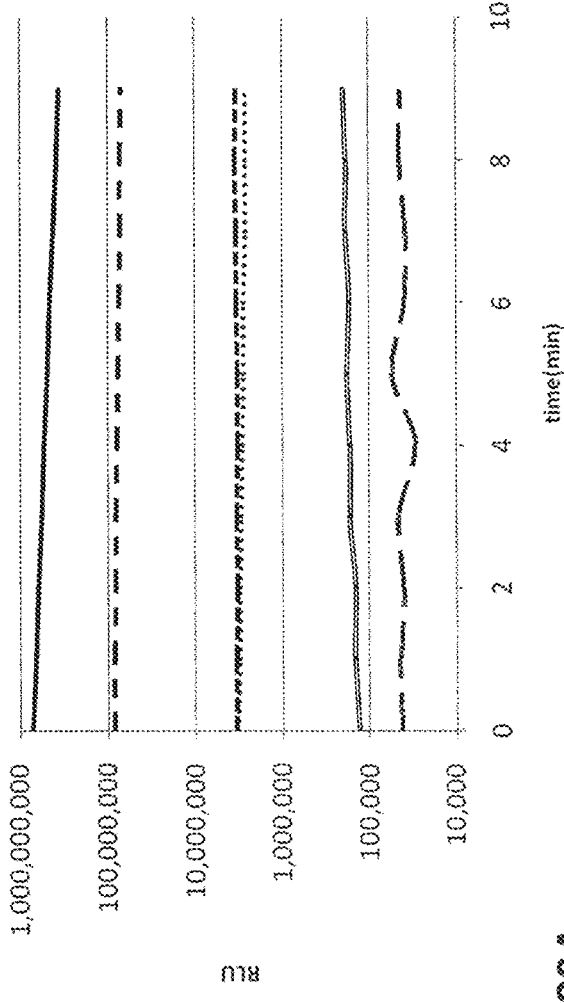
FIGS. 20A-B shows the light output time course (i.e. signal stability) of the C1+C2+A4E and C1+A4E OgLuc variants compared to WT OgLuc ("Og-Luc") and *Renilla* luciferase ("hRL"), and the T2T and A54F variants, using 0.5% tergitol assay buffer (20A) or RLAB (20B), with luminescence measured in RLU over time in minutes.
Figure 20B:
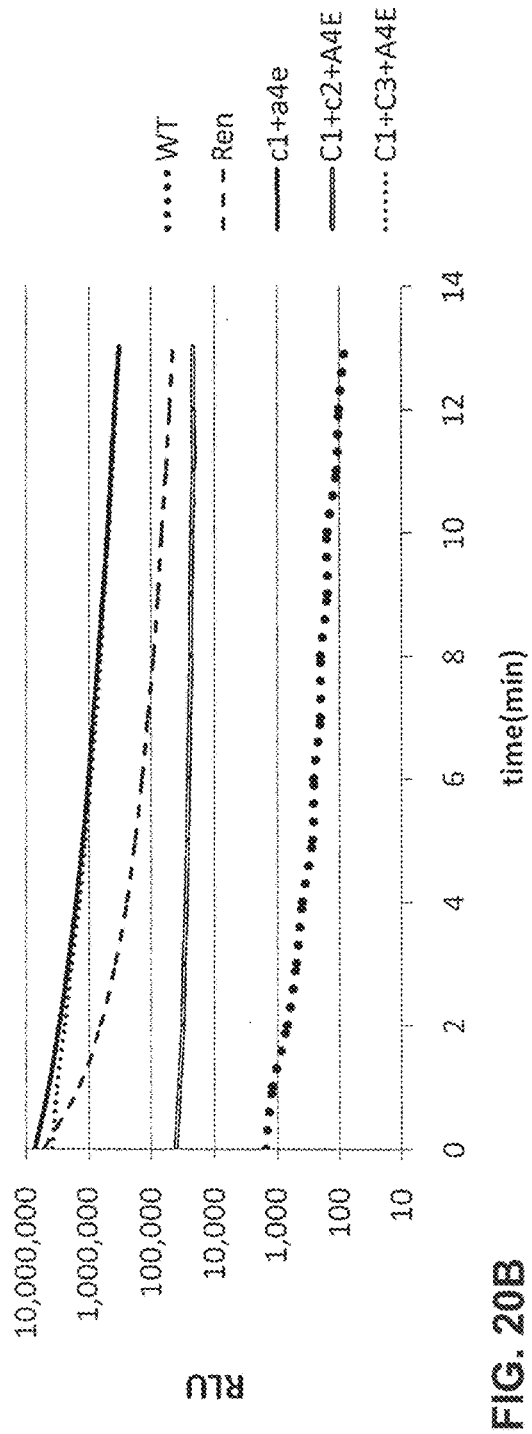
Figure 21:
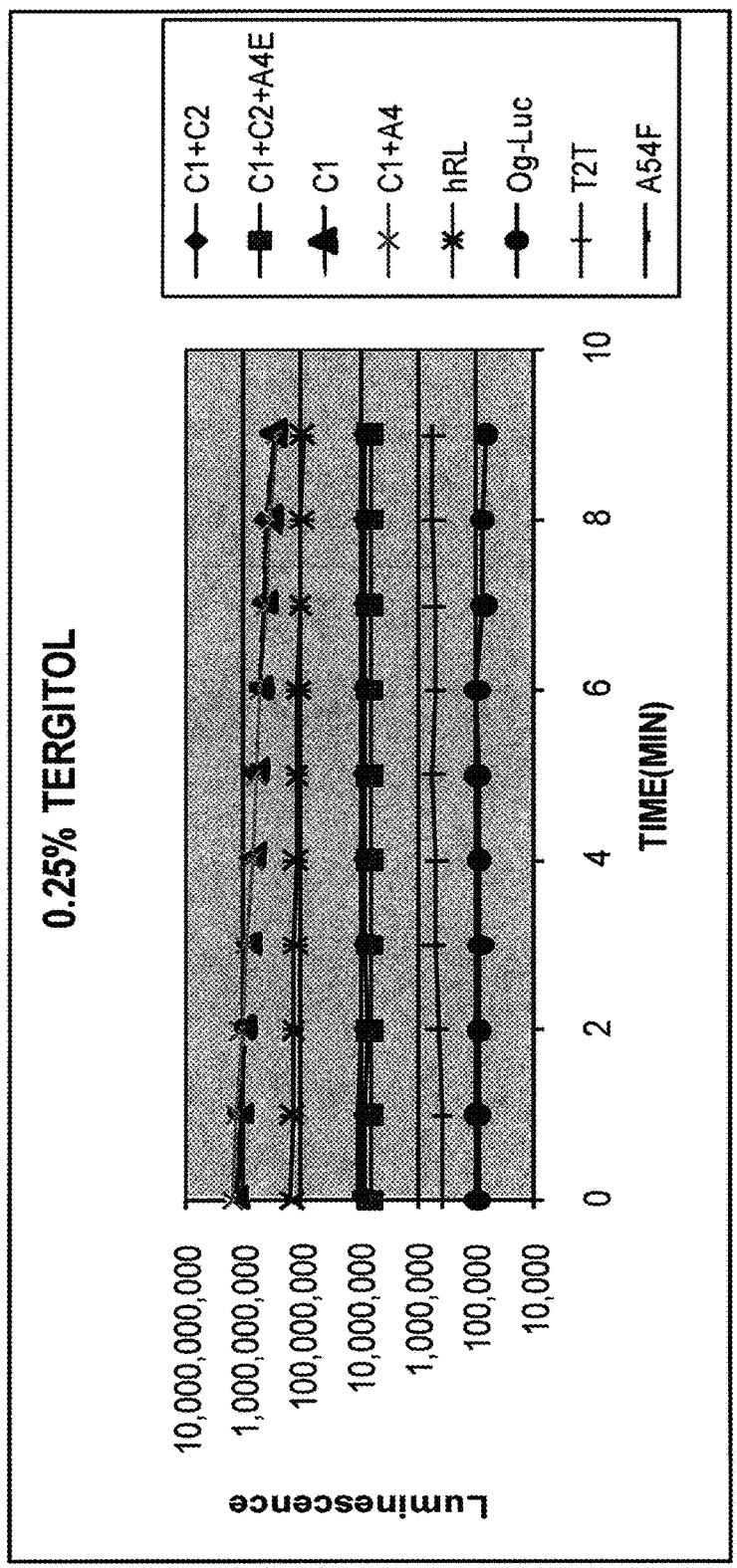
FIG. 21 shows the light output time course (i.e. signal stability) of the C1+C2+A4E and C1+A4E OgLuc variants compared to WT OgLuc ("Og-Luc") and *Renilla* luciferase ("hRL") and the T2T and A54F variants, using 0.25% tergitol assay buffer, with luminescence measured in RLU over time in minutes.

The luminescence of the C1, C1+A4E, C1+C2, and C1+C2+A4E variants, as compared with *Renilla* luciferase, WT OgLuc, T2T and the A54F variant, was measured using the method described in Example 4. (FIGS. 20A and 20B). The C1+A4E and C1+C2+A4E variants had 4 and 2-log increase, respectfully, over WT using 0.5% tergitol (FIG. 20A). The C1+A4E, C1+C2+A4E, and C1+C3+A4E variants had 3, 1.5, and 3-log increase, respectfully, over WT using RLAB (FIG. 20B). A 0.25% tergitol buffer was used instead of 0.5% tergitol to determine the stability of the signal, not reliant on tergitol. FIG. 21 shows the C1, C1+A4E, C1+C2, and C1+C2+A4E variants having 4, 4, 2, and 2-log increase, respectfully, over WT using 0.25% tergitol.

Figure 22:
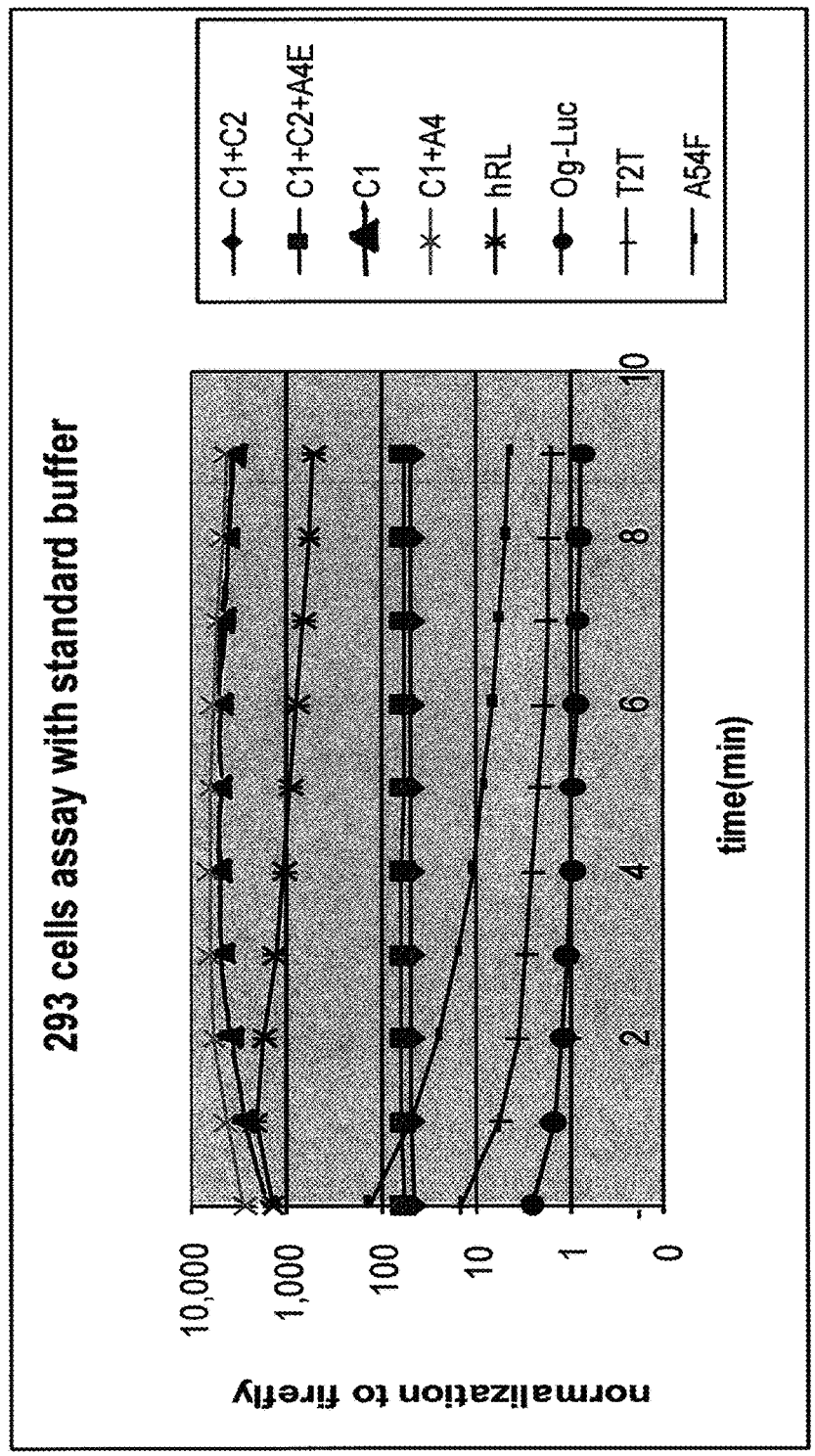
FIG. 22 shows the light output time course (i.e. signal stability) of the C1+C2+A4E and C1+A4E OgLuc variants compared to WT OgLuc ("Og-Luc") and *Renilla* luciferase ("hRL") and the T2T and A54F variants, in HEK 293 cells with RLAB buffer, normalized to firefly.
Figure 23:
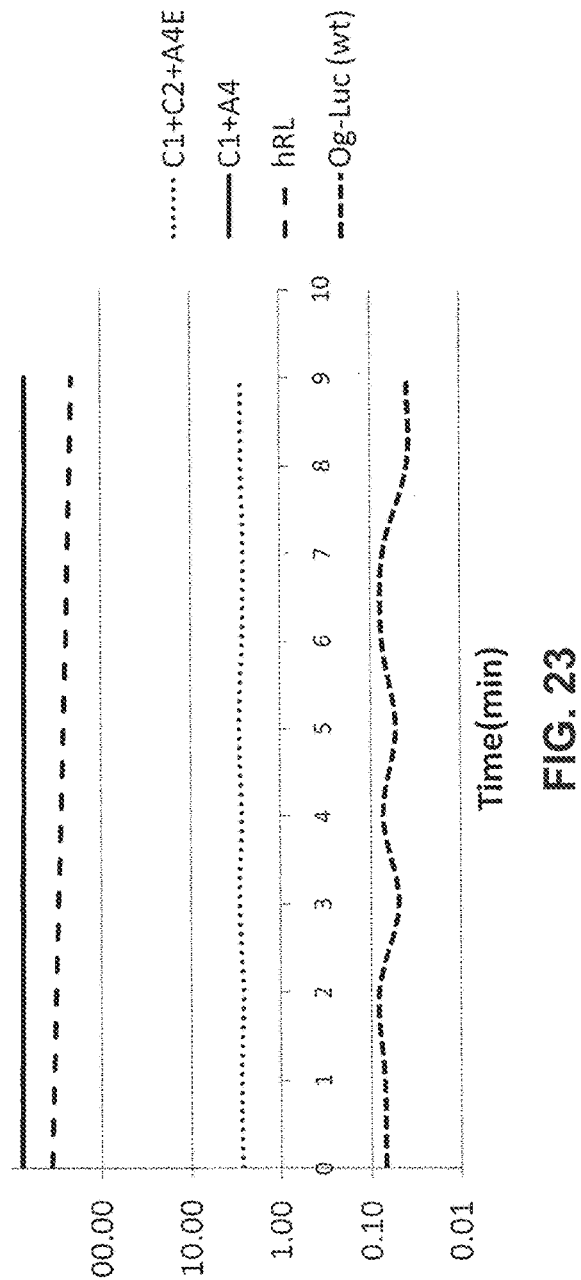
FIG. 23 shows the light output time course (i.e. signal stability) of the C1+C2+A4E and C1+A4E OgLuc variants compared to WT OgLuc ("Og-Luc") and *Renilla* luciferase ("hRL"), in HEK 293 cells, using 0.25% tergitol buffer, normalized to firefly.

The C1, C1+A4E, C1+C2, and C1+C2+A4E variants, as compared with *Renilla* luciferase, WT OgLuc, T2T and OgLuc+A54F variants, were also evaluated in HEK 293 cells. Briefly, HEK293 cells, plated at 15,000 cells/well in a 96-well plate, were transiently transfected using TransIT-LTI (minis Bio) with plasmid DNAs encoding the various variants and/or control sequences. The same plasmids also carried a gene for constitutive expression of firefly luciferase to act as a transfection control. Briefly, cells were grown, lysed and treated as described in Example 4. Cells were co-transfected with pGL4.13 for firefly transfection control (used 0.04 ug/tranfection or 10% of the total DNA transfected). Luminescence was measured as described in Example 4 using RLAB (FIG. 22) or 0.25% tergitol (FIG. 23). All modified luciferase data was then normalized for transfection efficiency using firefly luciferase luminescence (luciferin substrate) (FIGS. 22 and 23). The C1, C1+A4E, C1+C2, and C1+C2+A4E variants all had greater luminescence compared to OgLuc in 0.5% tergitol (FIG. 22). The C1+A4E and C1+C2+A4E variants also have greater luminescence compared to OgLuc in 0.25% tergitol (FIG. 23).

Example 10

Evaluation of Specific Combinations of Substitutions in Modified Luciferases—Protein Stability To determine if the amino acid substitutions in the different variants also had an effect on protein stability, the different variants were screened at different temperatures, and the effect on stability measured. As shown in FIG. 24, at room temperature (about 22° C.), the wild-type OgLuc showed a protein half-life of 1 hour while the C1 variant showed a protein half-life of 9.4 hours. As shown in FIG. 24, at 30° C., the OgLuc N166R variant had a protein half-life of 21 minutes while the C1+A4E variant showed now decay after 6 hours. At 30° C., the protein half-life for *Renilla* luciferase was 7.9 hours. The stability ranking at 30° C. is OgLuc C1+A4E>*Renilla* luciferase>OgLuc N166R. As shown in FIG. 24, at 37° C., the protein half-life of the OgLuc N166R variant was 2 minutes while no decay was seen in the C1+A4E variant. At 54° C., the protein half-lives of the different variants were as follows: C1: 7 minutes, C1+A4E: 8 minutes, C1+C2+A4E: 128 minutes, and C1+C3+A4E: 24 minutes. The half-lives of wild-type OgLuc and OgLuc N166R variant could not be determined at 54° C. because they were too unstable.

Example 11

Figure 25:
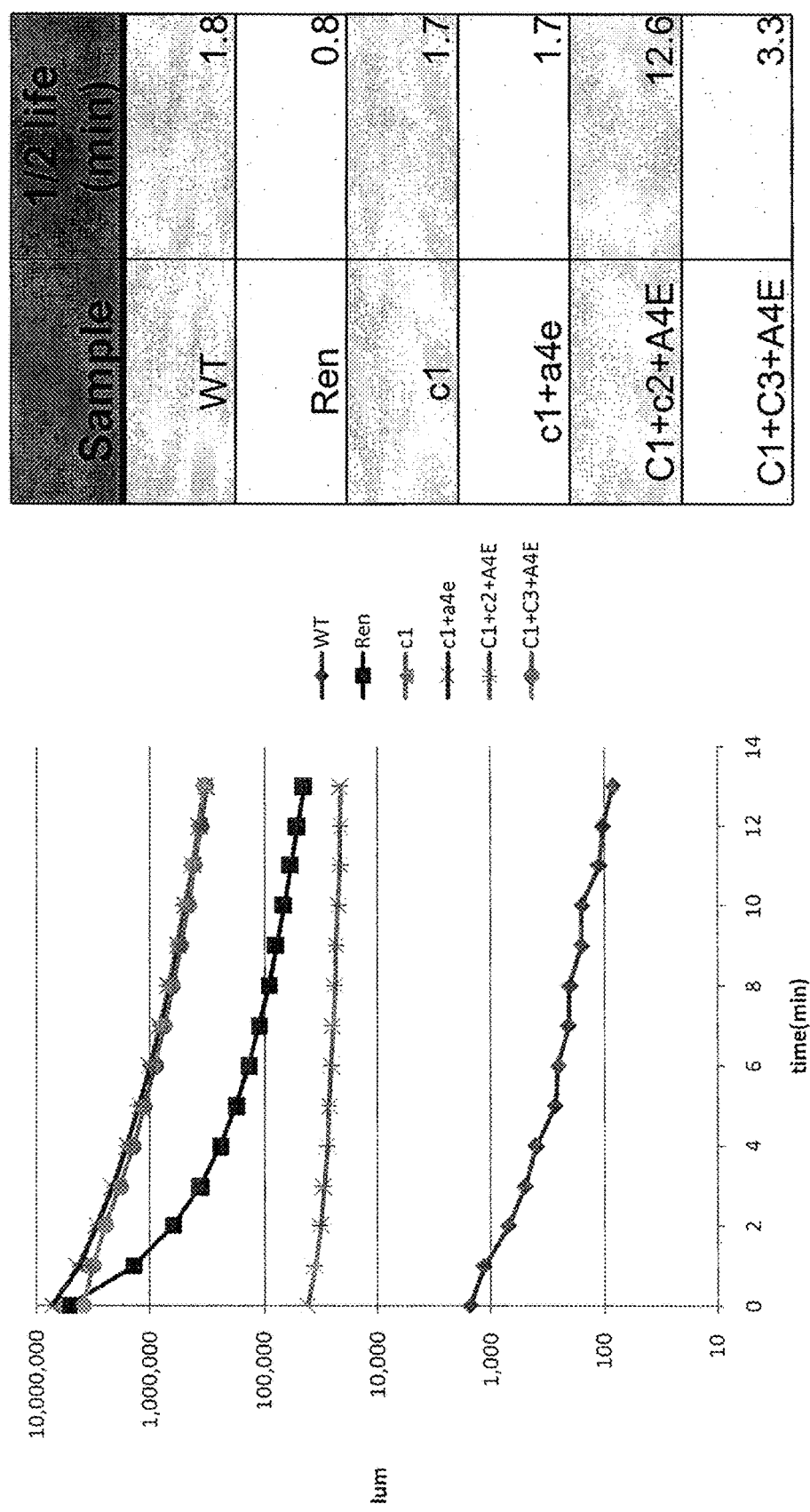
FIG. 25 shows the light output time course (i.e. signal stability) of the C1, C1+A4E, C1+C2+A4E, and C1+C3+A4E OgLuc variants compared to WT OgLuc ("Og-Luc") and *Renilla* luciferase ("hRL"), using RLAB with luminescence measured in RLU ("lum") over time in minutes, and the half-life in minutes determined from the time course data.

Evaluation of Specific Combinations of Substitutions in Modified Luciferases—Signal Stability To determine if the amino acid substitutions in the different variants also had an effect on signal stability, the different variants were screened for signal stability. Signal stability was measured as described in Example 4 using RLAB. The following signal half-lives were determined for the different variants: wild-type OgLuc:1.8 minutes, *Renilla* luciferase: 0.8 minutes, C1: 1.7 minutes, C1+A4E: 1.7 minutes, C1+C2+A4E: 12.6 minutes, and C1+C3+A4E: 3.3 minutes (FIG. 25).

Example 12

Figure 26:
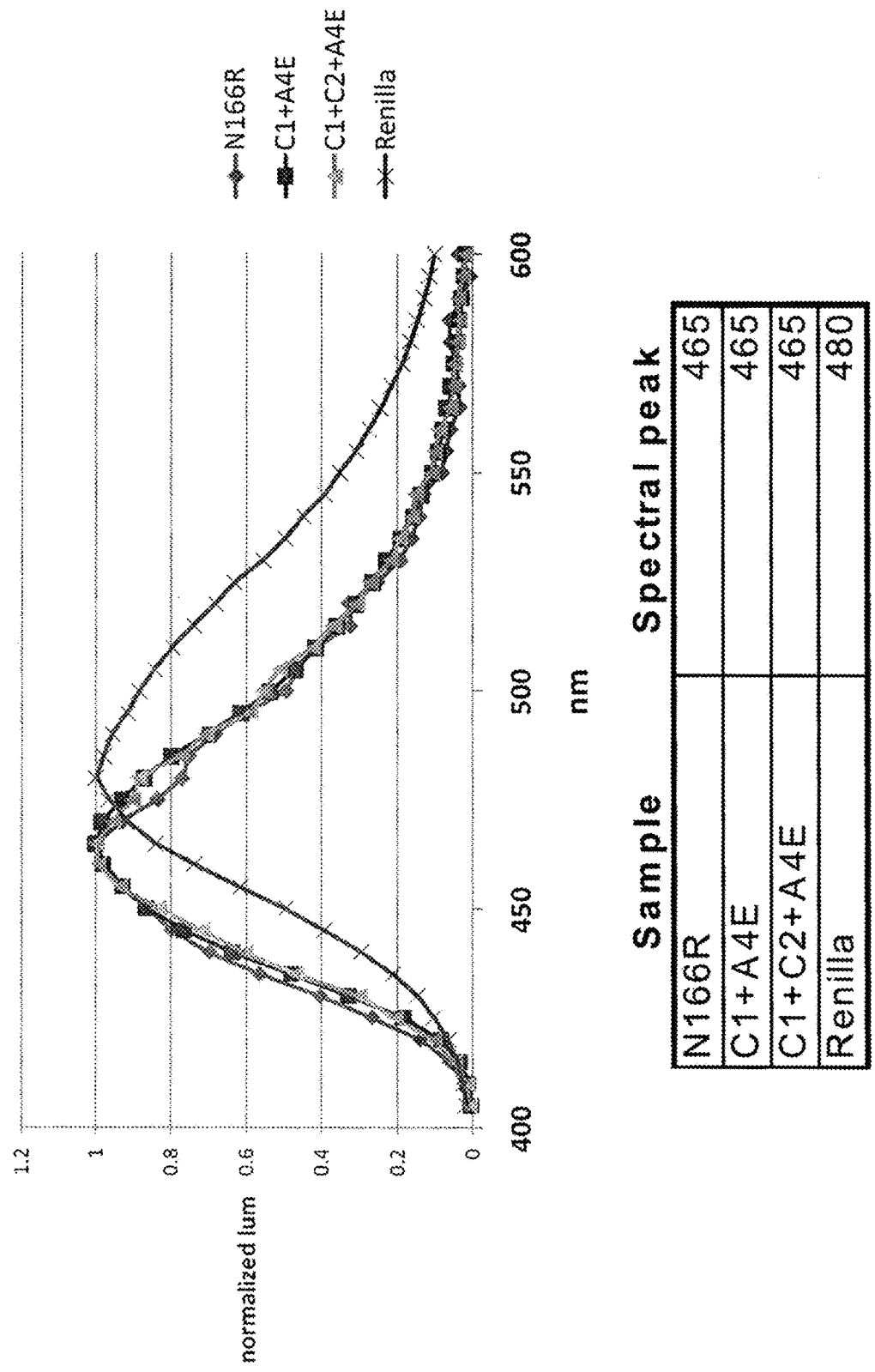
FIG. 26 shows the optimal wavelength in nm with the greatest luminescence, using coelenterazine as substrate for N166R, C1+A4E and C1+C2+A4E variants compared to *Renilla* luciferase, normalized by the highest RLU value in the spectrum.

Evaluation of Specific Combinations of Substitutions in Modified Luciferases—Luminescence Color The optimal wavelength with the greatest luminescence using coelenterzaine (Promega Corp.) as substrate was determined for the OgLuc+N166R, C1+A4E and C1+C2+A4E variants, compared with *Renilla* luciferase. Samples were prepared as described in Example 4. The spectral peak was determined by measuring the luminescence at 5 nm increments in wavelength using a Varioskan luminometer and 0.5% tergitol. The data was normalized by the highest RLU value in the spectrum. As shown in FIG. 26, *Renilla* has a spectral peak of 480 nm, while OgLuc+N166R, C1+A4E and C1+C2+A4E have a spectral peak at 465 nm, which is a shift from native OgLuc, which was previously reported to be 455 nm (Inouye, FEBS Letters, 481(1):19-25 (2000)).

Example 13

Generation of a Modified Luciferase with Increased Luminescence

Additional variants were generated by random mutagenesis as described in Example 3 of the C1+A4E variant. The total light output was measured as described in Example 4. Exemplary C1+A4E variants (i.e. those that are at least 1.2 times brighter than C1+A4E), but are not limited to, are listed in FIGS. 27A and 27B by Sample ID and the amino acid substitution. C1+A4E variants with an amino acid substitutions at positions 20, 54, 72, 77, 79, 89, 90, or 164 relative to SEQ ID NO: 1, showed at least 1.9 fold increase in luminescence over the corresponding starting C1+A4E variant.

Figure 30:
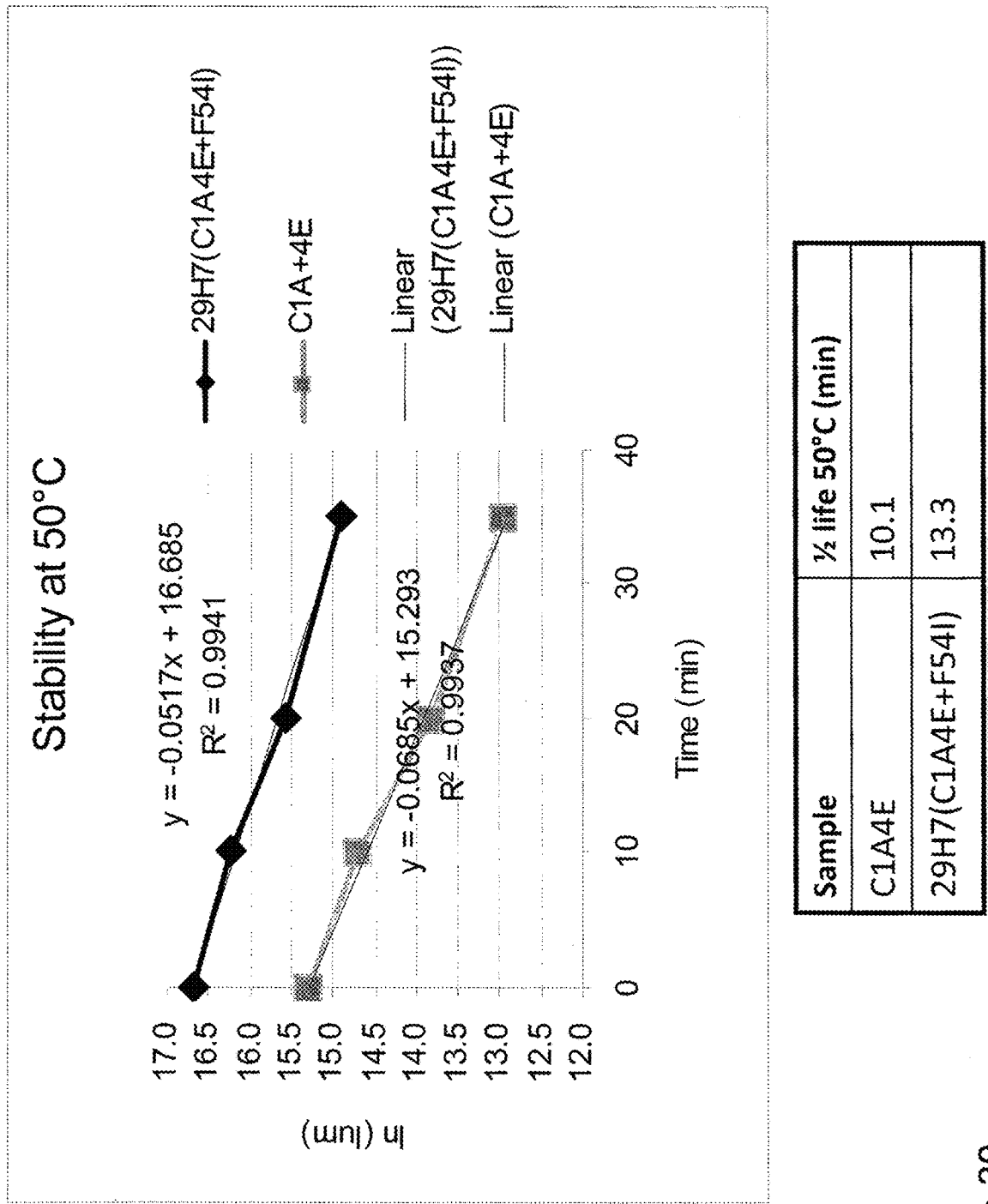
FIG. 30 shows the light output time course of the natural logarithm (1n) value of luminescence measured in RLU over time in minutes and the half-life in minutes of the variant C1+A4E+F54I, compared to corresponding starting C1+A4E OgLuc at 50° C.

Clone 29H7, which contained the C1+A4E+F54I variant was further tested for protein stability at 50° C. using the method described in Example 5. Clone 29H7 had a longer half-life than the corresponding starting C1+A4E variant (FIG. 30).

Various C1+A4E variants with an amino acid substitution at position 92 were analyzed for brightness, e.g., screened for variants that were at least 1.2 times brighter than C1+A4E variant. The following substitutions yielded a variant that was at least 1.2 times brighter than C1+A4E: L92G; L92Q; L92S; and L92A, and had 2.2, 2, 2.9 and 2.5 fold increase over C1+A4E respectively (see FIG. 28).

Additional variants were generated by site-directed mutagenesis, described in Example 3, of the C1+A4E variant, to have specific combinations of the substitutions F54I, F68S, M75K and I90V. As shown in FIG. 29, which lists the variants ("Sample ID") and the amino acid substitutions found in each variant, these combinations of substitutions show significant increase in luminescence of at least 17.5-19.3 fold over the corresponding starting C1+A4E variant.

Figure 34A:
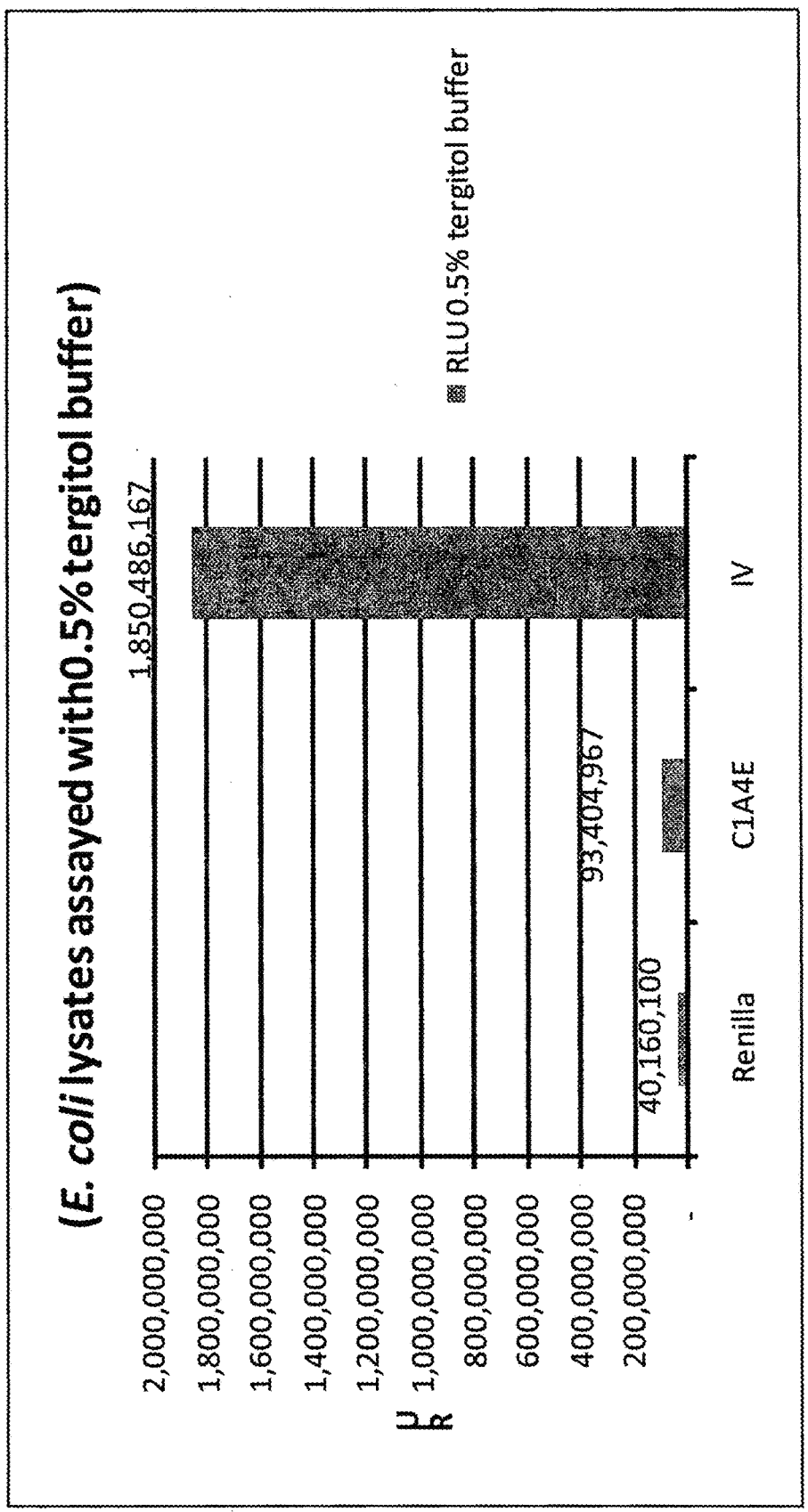
FIG. 34A shows the luminescence results of *E. coli* lysates containing the IV variant ("IV"), *Renilla* luciferase ("*Renilla*") and C1+A4E ("C1A4E") assayed with 0.5% tergitol.
Figure 34B:
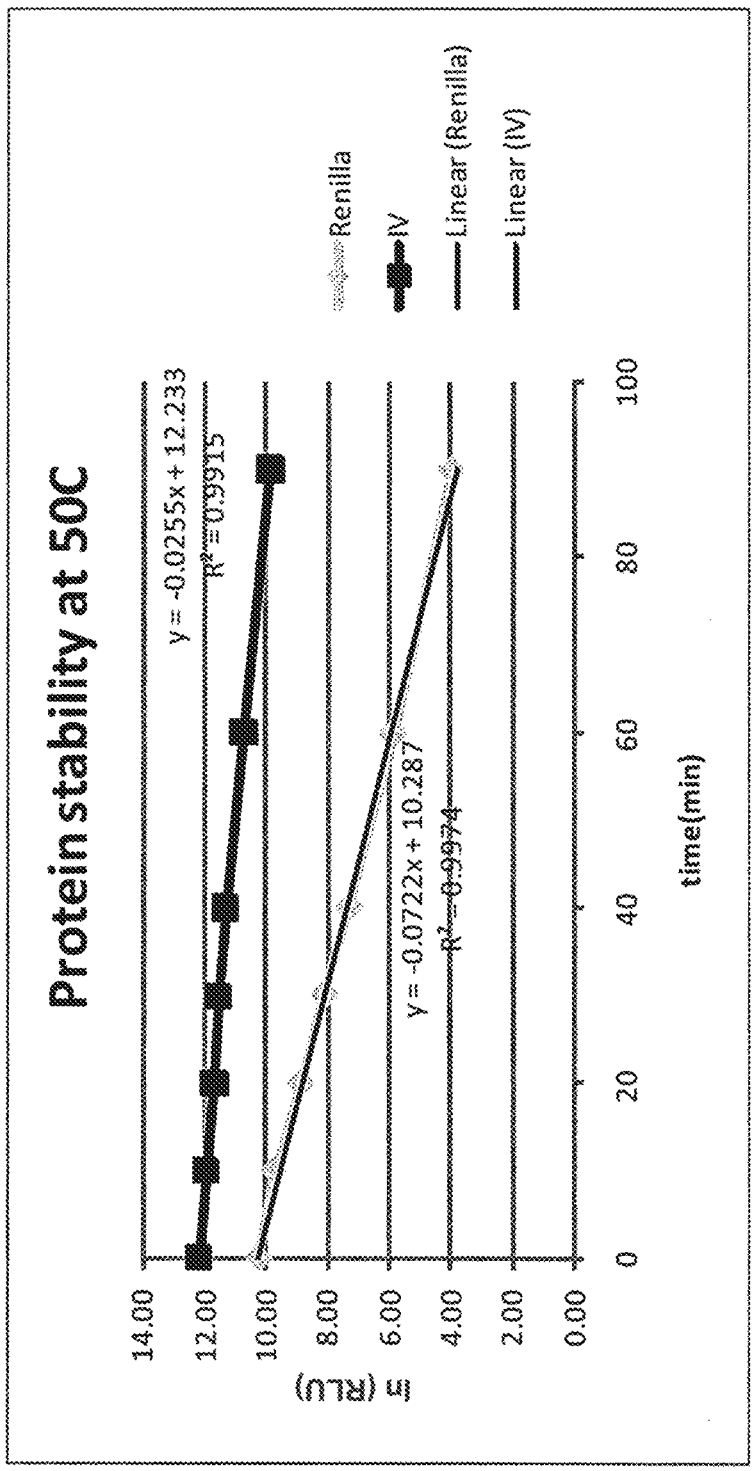
FIG. 34B shows the protein stability at 50° C. as the half-life in minutes of the VI variant ("VI") and *Renilla* luciferase ("*Renilla*").

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention. An additional specific combination variant of C1+A4E, was generated to include 190V and F54I ("IV"). As shown in FIG. 34A, IV had about 20 fold increase in luminescence compared to the corresponding starting C1+A4E variant as measured using the method of Example 4. As shown in FIG. 34B, the IV protein was more stable than *Renilla* luciferase at 50° C. as the half-life for IV was 27.2 minutes compared to *Renilla* which was 9.6 minutes using the method of Example 5.

Various features and advantages of the invention are set forth in the following claims.

What is claimed is:

1. A polynucleotide encoding a modified luciferase polypeptide comprising an amino acid sequence that is at least 70% identical to the amino acid sequence set forth in SEQ ID NO:1 and comprising at least one amino acid substitution at a position corresponding to position 2, 4, 11, 20, 23, 28, 33, 34, 44, 45, 51, 54, 68, 72, 75, 76, 77, 89, 90, 92, 99, 104, 115, 124, 135, 138, 139, 143, 144,166, 167, or 169 of SEQ ID NO:1, wherein the modified luciferase polypeptide has at least one of enhanced luminescence, enhanced signal stability, and enhanced protein stability relative to a wild-type Oplophorus luciferase, wherein the modified luciferase polypeptide has luciferase activity and utilizes a coelenterazine as a substrate to generate luminescence.

2. The polynucleotide of claim 1, wherein the modified luciferase polypeptide has enhanced signal stability relative to that of a wild-type Oplophorus luciferase, and has at least one amino acid substitution at a position corresponding to at least one of positions 4, 11, 20, 28, 33, 54, 68, 75, 115, 124, 138, 143, or 166 of SEQ ID NO:1.

3. The polynucleotide of claim 1, wherein the encoded modified luciferase polypeptide has enhanced protein stability relative to that of a wild-type Oplophorus luciferase, and at least one amino acid substitution at a position corresponding to at least one of positions 11, 20, 28, 33, 34, 44, 45, 51, 54, 68, 72, 75, 77, 89, 90, 92, 99, 104, 115, 124, 135, 138, 139, 143, 144, 166, 167, or 169 of SEQ ID NO:1.

4. The polynucleotide of claim 1, wherein the encoded modified luciferase polypeptide further comprises a deletion of as many as 27 amino acid residues corresponding to the N-terminus of the wild-type Oplophorus luciferase of SEQ ID NO:10.

5. The polynucleotide of claim 4, wherein the deletion constitutes a deletion of the 27 amino acid residues corresponding to the N-terminus of SEQ ID NO:10.

6. The polynucleotide of claim 1, wherein the wild-type Oplophorus luciferase is from Oplophorus gracilirostris, Oplophorus grimaldii, Oplophorus spinicauda, Oplophorus fofiaceus, Oplophorus novaezelandiae, Oplophorus typus, or Oplophorus spinous.

7. The polynucleotide of claim 1, wherein the encoded modified luciferase polypeptide comprises a substitution corresponding to at least one of T2S, A4E/S/R/G/D/T/L, Q11R/V/I/L/K/T, Q20R, E23V, S28P, A33K, V44I/L, V45E, G51V, A54F/T/V/G/S/W/L/I, F68S/YN, L72Q, M75R/K/Q/G/T/A, I76V, F77W, V79I, K89E, I90T/V, L92S/A/G/Q, I99V, P104L, P115E/I/Q/L/V/G/H/R/S/C/A/T, Q124K, N135K, Y138V/I/N/T/L/C/R/M/K, D139E, I143L, N144K, N166R/K/A/L/P/Q/S, I167V, or A169L where the positions are numbered by correspondence with positions in the amino acid sequence of SEQ ID NO:1.

8. The polynucleotide of claim 1, wherein the encoded modified luciferase polypeptide comprises amino acid substitutions at positions corresponding to positions 11, 33, 44, 54, 115, 124, 138, and 166 in the amino acid sequence of SEQ ID NO:1.

9. The polynucleotide of claim 8, wherein the amino acid substitutions comprise Q11R, A33K, V44I, A54F, P115E, Q124K, Y138I, and N166R.

10. The polynucleotide of claim 8, wherein the encoded modified luciferase further comprises an amino acid substitution at a position corresponding to position 4 in the amino acid sequence of SEQ ID NO:1.

11. The polynucleotide of claim 10, wherein the amino acid substitution made at position 4 is glutamic acid.

12. The polynucleotide of claim 8, wherein the encoded modified luciferase further comprises amino acid substitutions at positions corresponding to positions 45, 104, 135, 139, and 167 in the amino acid sequence of SEQ ID NO:1.

13. The polynucleotide of claim 12, wherein the amino acid substitution made at position 45 is glutamic acid, the amino acid substitution made position 104 is leucine, the amino acid substitution made at position 135 is lysine, the amino acid substitution made at position 139 is glutamic acid, and the amino acid substitution made at position 167 is valine.

14. The polynucleotide of claim 10, wherein the encoded modified luciferase further comprises amino acid substitutions at positions corresponding to positions 28, 34, 51, 99 and 143 in the amino acid sequence of SEQ ID NO:1.

15. The polynucleotide of claim 14, wherein the amino acid substitution made at position 28 is proline, the amino acid substitution made at position 34 is methionine, the amino acid substitution made at position 51 is valine, the amino acid substitution made at position 99 is valine, and the amino acid substitution made at position 143 is leucine.

16. The polynucleotide of claim 10, wherein the encoded modified luciferase further comprises an amino acid substitution at one or more positions corresponding to positions 20, 54, 68, 72, 75, 77, 79, 89, 90, 92, and 164 in the amino acid sequence of SEQ ID NO:1.

17. The polynucleotide of claim 16, wherein an amino acid substitution made at position 20 is arginine, an amino acid substitution made at position 54 is isoleucine, an amino acid substitution made at position 68 is serine, an amino acid substitution made at position 72 is glutamine, the amino acid substitution made at position 75 is lysine, an amino acid substitution made at position 77 is tryptophan, an amino acid substitution made at position 79 is isoleucine, an amino acid substitution made at position 89 is glutamic acid, an amino acid substitution made at position 90 is either threonine or valine, an amino acid substitution made at position 92 is selected from the group consisting of glycine, glutamine, serine and alanine, and an amino acid substitution made at position 164 is serine.

18. The polynucleotide of claim 10, wherein the encoded modified luciferase polypeptide further comprises amino acid substitutions at positions corresponding to positions 23, 28, 143, and 166 in the amino acid sequence of SEQ ID NO:1.

19. The polynucleotide of claim 18, wherein the amino acid substitutions comprise E23V, S28P, I143V, and N166R.

20. The polynucleotide of claim 1, wherein the encoded modified luciferase polypeptide further comprises amino acid substitutions at positions corresponding to positions 4, 34, 76, and 166 in the amino acid sequence of SEQ ID NO:1.

21. The polynucleotide of claim 20, wherein the amino acid substitutions comprise A4S, L34M, I76V, and N166R.

22. The polynucleotide of claim 1, wherein the encoded modified luciferase polypeptide further comprises amino acid substitutions at positions corresponding to positions 51, 99, and 166 in the amino acid sequence of SEQ ID NO:1.

23. The polynucleotide of claim 22, wherein the amino acid substitutions comprise G51V, I99V, and N166R.

24. The polynucleotide of claim 1, wherein the polynucleotide further encodes a polypeptide of interest linked to the modified luciferase polypeptide and the polypeptide of interest and the modified luciferase polypeptide are capable of being expressed as a fusion protein.

25. A vector comprising the polynucleotide of claim 1.

26. The vector of claim 25, wherein the polynucleotide is operably linked to a promoter.

27. An isolated cell comprising the polynucleotide of claim 1.

28. A kit comprising the polynucleotide of claim 1.

29. An isolated cell comprising the vector of claim 25.

30. A kit comprising the vector of claim 25.

\* \* \* \* \*